(12) United States Patent
Huang et al.

(10) Patent No.: US 11,399,747 B2
(45) Date of Patent: Aug. 2, 2022

(54) PHYSIOLOGICAL SIGNAL MONITORING DEVICE

(71) Applicant: BIONIME CORPORATION, Taichung (TW)

(72) Inventors: Chun-Mu Huang, Taichung (TW); Chieh-Hsing Chen, Taichung (TW); Chen-Hao Lee, Taichung (TW)

(73) Assignee: BIONIME CORPORATION, Taichung (TW)

( * ) Notice: Subject to any disclaimer, the term of this patent is extended or adjusted under 35 U.S.C. 154(b) by 0 days.

(21) Appl. No.: 16/944,540

(22) Filed: Jul. 31, 2020

(65) Prior Publication Data
US 2021/0030325 A1 Feb. 4, 2021

Related U.S. Application Data

(60) Provisional application No. 62/882,140, filed on Aug. 2, 2019.

(30) Foreign Application Priority Data

Jan. 10, 2020 (TW) .................................. 109100961

(51) Int. Cl.
*A61B 5/145* (2006.01)
*A61B 5/00* (2006.01)
*A61B 5/1486* (2006.01)

(52) U.S. Cl.
CPC ........ *A61B 5/14532* (2013.01); *A61B 5/0004* (2013.01); *A61B 5/6832* (2013.01);
(Continued)

(58) Field of Classification Search
CPC .. A61B 5/14532; A61B 5/1473–14735; A61B 5/1486–14865; A61B 5/6833;
(Continued)

(56) References Cited

U.S. PATENT DOCUMENTS 5,879,373 A * 3/1999 Roper ................ A61B 5/14552
600/340
7,899,511 B2 3/2011 Brauker et al.
(Continued)

FOREIGN PATENT DOCUMENTS

CN 103750819 A 4/2014
CN 203644304 U 6/2014
(Continued)

OTHER PUBLICATIONS

A Search Report, which was issued to European counterpart application No. 20188915.1 by the EPO dated Dec. 16, 2020.
(Continued)

*Primary Examiner* — Eric F Winakur
*Assistant Examiner* — Alice Ling Zou
(74) *Attorney, Agent, or Firm* — Perkins Coie LLP; Yang Tang

(57) ABSTRACT

A physiological signal monitoring device includes a base, a biosensor mounted to the base and adapted to measure an analytical substance, and a transmitter. The base includes a flexible base body and a first coupling structure. The first coupling structure is disposed on the bottom plate. The transmitter is removably mounted to the base body, and includes a bottom casing and a second coupling structure. The first and second coupling structures are coupled to each other when the transmitter is mounted to the base body, and are uncoupled from each other by the flexibility of the base body when an external force is applied on a periphery of the base body. The first and second coupling structures are disposed to be distal from a periphery cooperatively defined by the base and the transmitter when the first and second coupling structures are coupled to each other.

17 Claims, 45 Drawing Sheets

(52) U.S. Cl.
CPC ..... *A61B 5/14865* (2013.01); *A61B 2562/166* (2013.01); *A61B 2562/227* (2013.01)

(58) Field of Classification Search
CPC ...... A61B 5/14546; A61B 5/683–6835; A61B 2560/0412; A61B 2560/0443; A61B 5/1451; A61B 5/1468–1477; A61B 5/68–6801; A61B 5/681; A61B 5/6831–6833
See application file for complete search history.

(56) References Cited

U.S. PATENT DOCUMENTS

| | | | |
|---|---|---|---|
| 8,792,955 | B2 | 7/2014 | Brauker et al. |
| 8,886,272 | B2 | 11/2014 | Brister et al. |
| 9,931,065 | B2 | 4/2018 | Pryor et al. |
| 10,251,286 | B2 | 4/2019 | Rickert et al. |
| 10,327,638 | B2 | 6/2019 | Brister et al. |
| 2006/0020186 | A1 | 1/2006 | Brister et al. |
| 2006/0195029 | A1 | 8/2006 | Shults et al. |
| 2007/0073129 | A1 | 3/2007 | Shah et al. |
| 2009/0076360 | A1* | 3/2009 | Brister ............... A61B 5/6833 600/365 |
| 2009/0085768 | A1 | 4/2009 | Patel et al. |
| 2010/0049025 | A1 | 2/2010 | Taub |
| 2010/0222703 | A1 | 9/2010 | Takashima et al. |
| 2012/0010642 | A1 | 1/2012 | Lee et al. |
| 2012/0088999 | A1 | 4/2012 | Bardy et al. |
| 2012/0172691 | A1 | 7/2012 | Goode et al. |
| 2013/0267811 | A1 | 10/2013 | Pryor et al. |
| 2013/0267813 | A1* | 10/2013 | Pryor ............... A61B 5/6849 600/365 |
| 2014/0142405 | A1 | 5/2014 | Brister et al. |
| 2015/0173215 | A1* | 6/2015 | Rickert ............... H04Q 9/14 340/870.28 |
| 2016/0058380 | A1* | 3/2016 | Lee ............... A61B 5/68335 600/365 |
| 2016/0058474 | A1* | 3/2016 | Peterson ............... A61B 5/686 600/347 |
| 2016/0256095 | A1 | 9/2016 | Krasnow et al. |
| 2017/0011210 | A1 | 1/2017 | Cheong et al. |
| 2017/0112534 | A1* | 4/2017 | Schoonmaker ...... A61B 5/0004 |
| 2017/0188912 | A1* | 7/2017 | Halac ............... A61B 5/14865 |
| 2017/0290534 | A1 | 10/2017 | Antonio et al. |
| 2017/0319119 | A1 | 11/2017 | Krasnow et al. |
| 2018/0116570 | A1 | 5/2018 | Simpson et al. |
| 2018/0317820 | A1 | 11/2018 | Pace et al. |
| 2019/0320956 | A1 | 10/2019 | Pryor et al. |
| 2019/0336055 | A1* | 11/2019 | Shah ............... A61B 5/0004 |
| 2020/0178899 | A1 | 6/2020 | Chae et al. |

FOREIGN PATENT DOCUMENTS

| | | | | |
|---|---|---|---|---|
| CN | 106137214 | A | 11/2016 | |
| CN | 206092596 | U | 4/2017 | |
| CN | 107015000 | A | 8/2017 | |
| CN | 208143260 | U | 11/2018 | |
| CN | 109998560 | A | 7/2019 | |
| EP | 3195795 | A1 * | 7/2017 | .......... A61B 5/1473 |
| JP | 2017202235 | A | 11/2017 | |
| JP | 2018000313 | A | 1/2018 | |
| WO | 2010099507 | A1 | 9/2010 | |
| WO | 2014045447 | A1 | 3/2014 | |
| WO | 2016036924 | A2 | 3/2016 | |
| WO | 2017070360 | A1 | 4/2017 | |
| WO | 2018057643 | A1 | 3/2018 | |

OTHER PUBLICATIONS

An International Search Repod, which was issued to PCT application No. PCT/IB2020/057247 by the WIPO dated Dec. 9, 2020.

An Office Action, which was issued to European counterpart application No. 20188915.1 by the EPO dated Oct. 22, 2021. 7 pages.

* cited by examiner

PHYSIOLOGICAL SIGNAL MONITORING DEVICE

CROSS-REFERENCE TO RELATED APPLICATION

This application claims priority of U.S. Provisional Patent Application No. 62/882,140, filed on Aug. 2, 2019, and Taiwanese Patent Application No. 109100961, filed on Jan. 10, 2020.

FIELD

The disclosure relates to a monitoring device, and more particularly to a physiological signal monitoring device.

BACKGROUND

Continuous glucose monitoring (CGM) is a popular method for tracking changes in glucose levels by taking glucose measurements of an individual at regular intervals. In order to utilize a CGM system, the individual wears a form of compact, miniature sensing device.

Referring to FIG. 45, a conventional sensing device 900 disclosed in U.S. Pat. No. 7,899,511 includes a mounting unit 92, an adhesive base 91 that is adapted for adhering the mounting unit 92 onto a host's skin (not shown), a biosensor 93 that is mounted in the mounting unit 92, and a transmitter 94 that is mounted to the mounting unit 92 and that is connected to the biosensor 93. The biosensor 93 is inserted beneath the host's skin for measuring a physiological signal corresponding to the glucose concentration level, and the transmitter 94 receives the physiological signal from the biosensor 93 and forwards the physiological signal to an external device (not shown).

Due to the intrusive nature of the sensing device 900, the host's body may become hypersensitive to the biosensor 93, and in turn develops a severe allergic reaction. As such, the biosensor 93 has to be replaced on a weekly or bi-weekly basis. In comparison, as the transmitter 94 is relatively expensive, when the biosensor 93 is to be replaced, the transmitter 94 is usually disengaged from the mounting unit 92 for next uses. However, in order to implement a coupling mechanism, such as the coupling lock 921 shown in FIG. 45, that cannot easily disengage the transmitter 94 from the mounting unit 92, the sensing device 900 is required to have a relatively high thickness, thereby making the sensing device 900 rather bulky. While another type of coupling mechanism disengages the transmitter from the mounting unit via rotation without requiring a high minimum thickness, the structure of such coupling mechanism is too complicated to manufacture, and is more difficult to operate.

SUMMARY

Therefore, an object of the disclosure is to provide a physiological signal monitoring device that can alleviate the drawbacks of the prior arts.

According to one aspect of the disclosure, the physiological signal monitoring device includes a base, a biosensor and a transmitter. The base includes a base body and at least one first coupling structure. The base body is flexible and has a bottom plate adapted to be mounted to a skin surface of a host. The first coupling structure is disposed on a top surface of the bottom plate. The biosensor is mounted to the base and is adapted to measure at least one analytical substance of the host and to send a physiological signal corresponding to the analytical substance. The transmitter is removably mounted to the base body, is connected to the biosensor, and is for receiving and transmitting the physiological signal. The transmitter includes a bottom casing (31) facing the top surface of the bottom plate of the base body, and at least one second coupling structure disposed on the bottom casing and corresponding in position to the at least one first coupling structure of the base. The first and second coupling structures are coupled to each other when the transmitter is mounted to the base body of the base, and are uncoupled from each other when an external force is applied on a periphery of the base body to bend the bottom plate by the flexibility of the base body. The first and second coupling structures are disposed to be distal from a periphery cooperatively defined by the base and the transmitter when the first and second coupling structures are coupled to each other.

According to another aspect of the disclosure, the physiological signal monitoring device includes a base, a biosensor and a transmitter. The base includes a base body and at least one first coupling structure. The base body has a bottom plate that is adapted to be mounted to a skin surface of a host, and a surrounding wall that extends upwardly from a periphery of the bottom plate. The height of the surrounding wall of the base body measured from a top surface of the bottom plate is not uniform so that the base body is flexible. The first coupling structure is disposed on the top surface of the bottom plate. The biosensor is mounted to the base, and is adapted to measure at least one analytical substance of the host and to send a physiological signal corresponding to the analytical substance. The transmitter is removably mounted to the base body, is coupled to the biosensor, and is for receiving and transmitting the physiological signal. The transmitter includes a bottom casing facing the top surface of the bottom plate of the base body, and at least one second coupling structure disposed on the bottom casing and corresponding in position to the at least one first coupling structure of the base. The first and second coupling structures are coupled to each other when the transmitter is mounted to the base body of the base, and are uncoupled from each other when an external force is applied on a periphery of the base body to bend the bottom plate by the flexibility of the surrounding wall. The first and second coupling structures are disposed to be distal from a periphery cooperatively defined by the base and the transmitter when the first and second coupling structures are coupled to each other.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
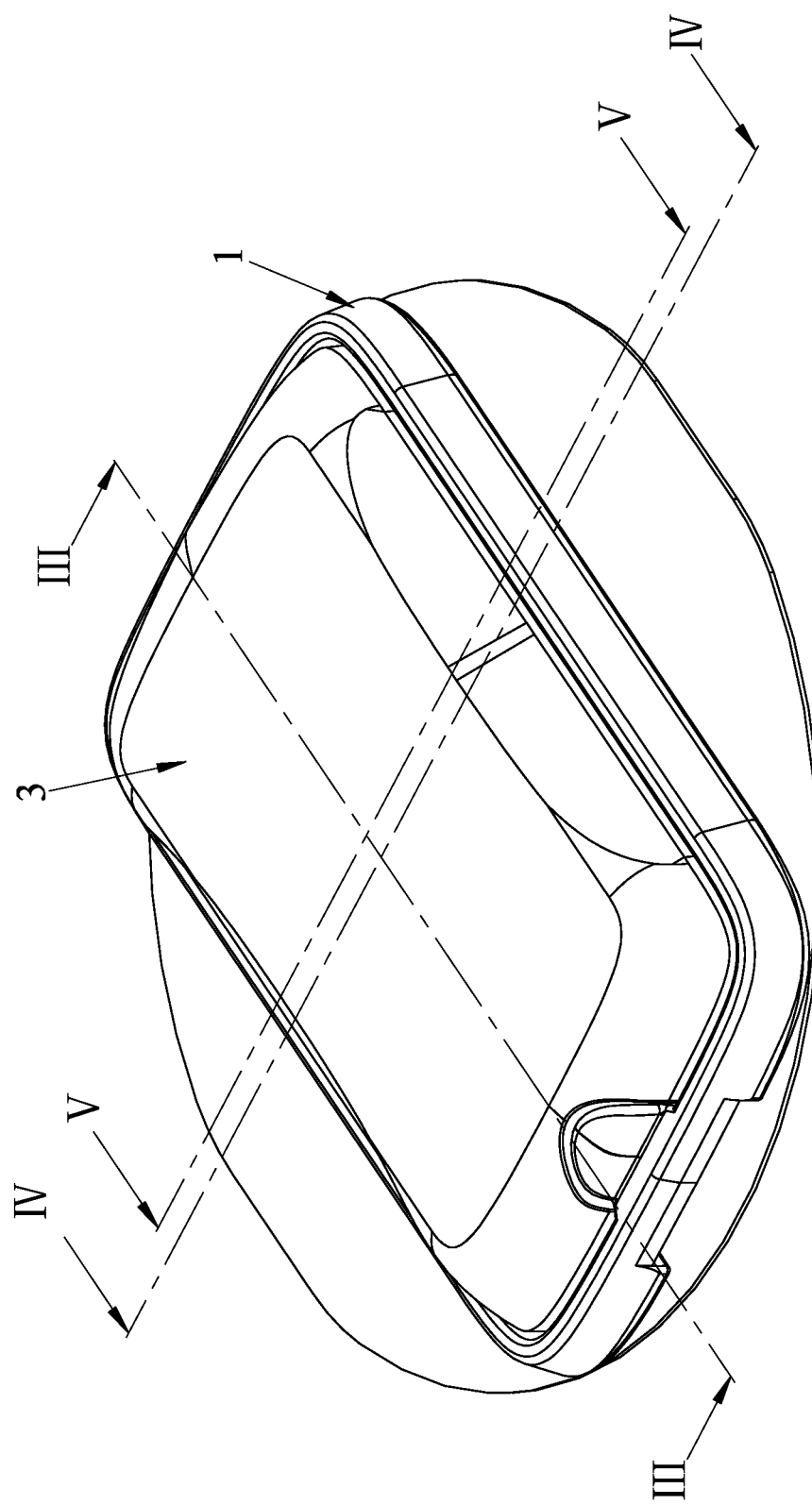
FIG. 1 is a perspective view of a first embodiment of a physiological signal monitoring device according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

In addition, in the description of the disclosure, the terms "up", "down", "top", "bottom" are meant to indicate relative position between the elements of the disclosure, and are not meant to indicate the actual position of each of the elements in actual implementations. Similarly, various axes to be disclosed herein, while defined to be perpendicular to one another in the disclosure, may not be necessarily perpendicular in actual implementation.

Figure 2:
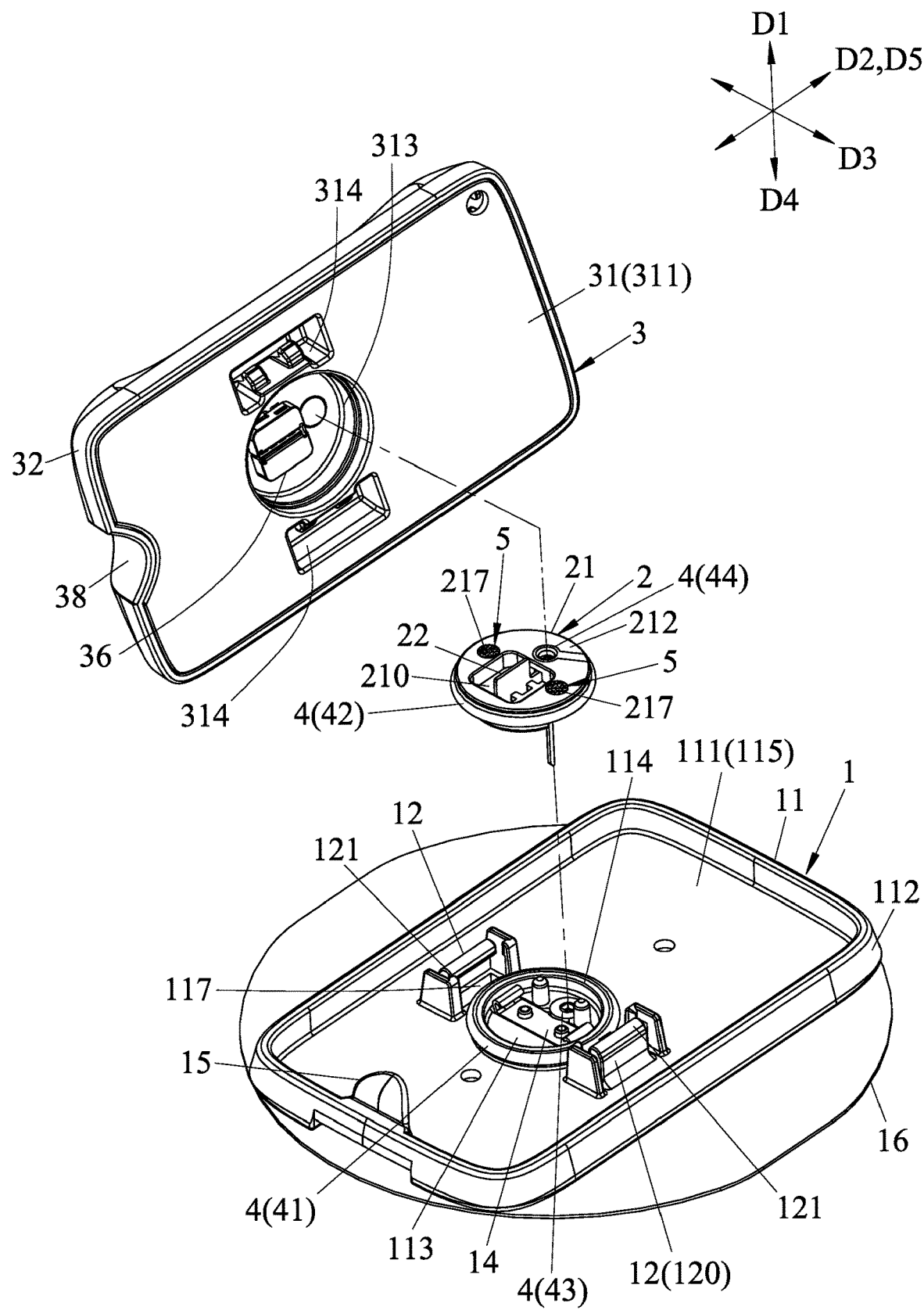
FIG. 2 is an exploded perspective view of the first embodiment.
Figure 12:
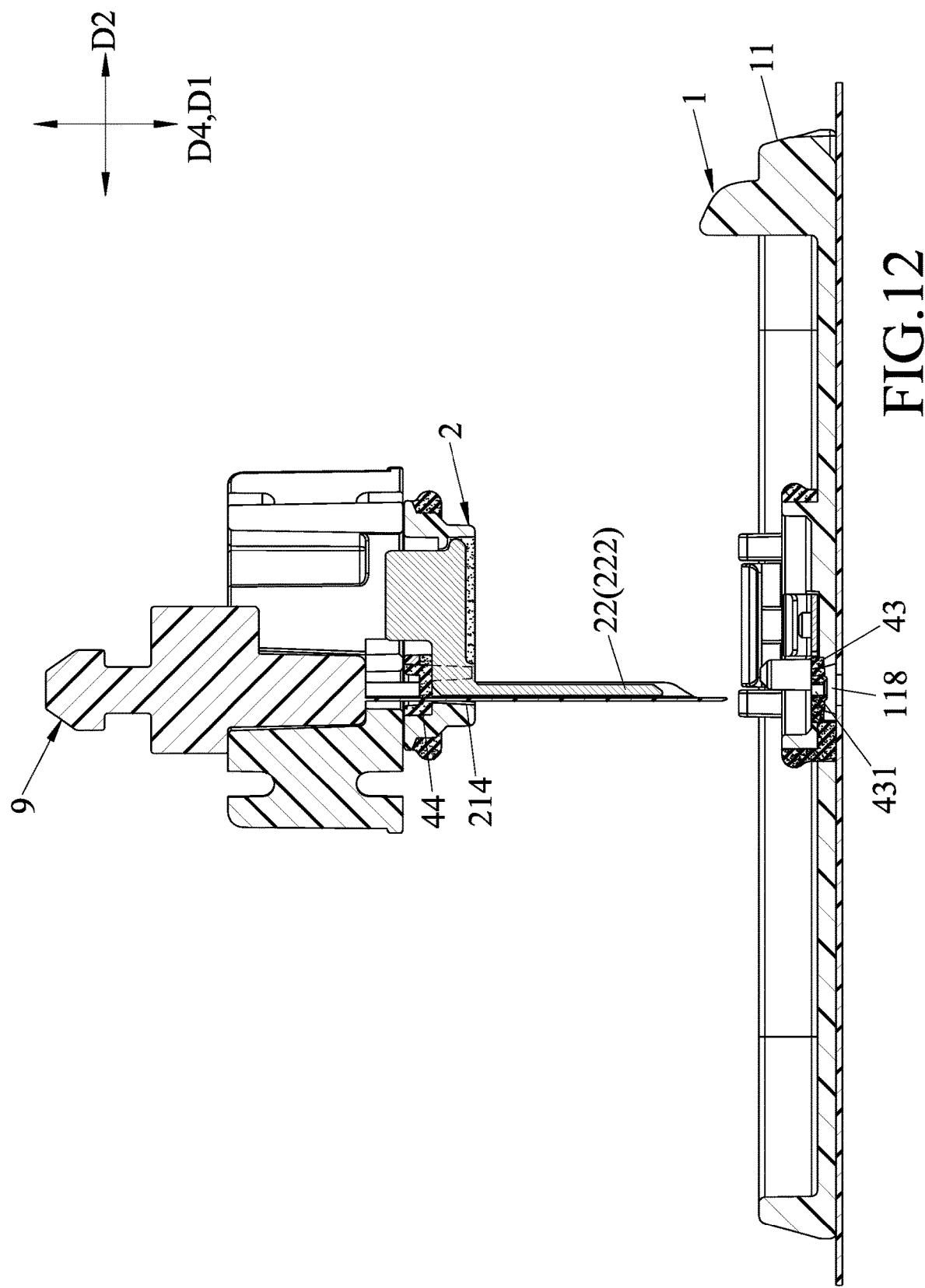
FIGS. 12 and 13 are sectional views of a base and the biosensor of the first embodiment, illustrating the biosensor before and after being coupled to the base via an insertion tool.
Figure 13:
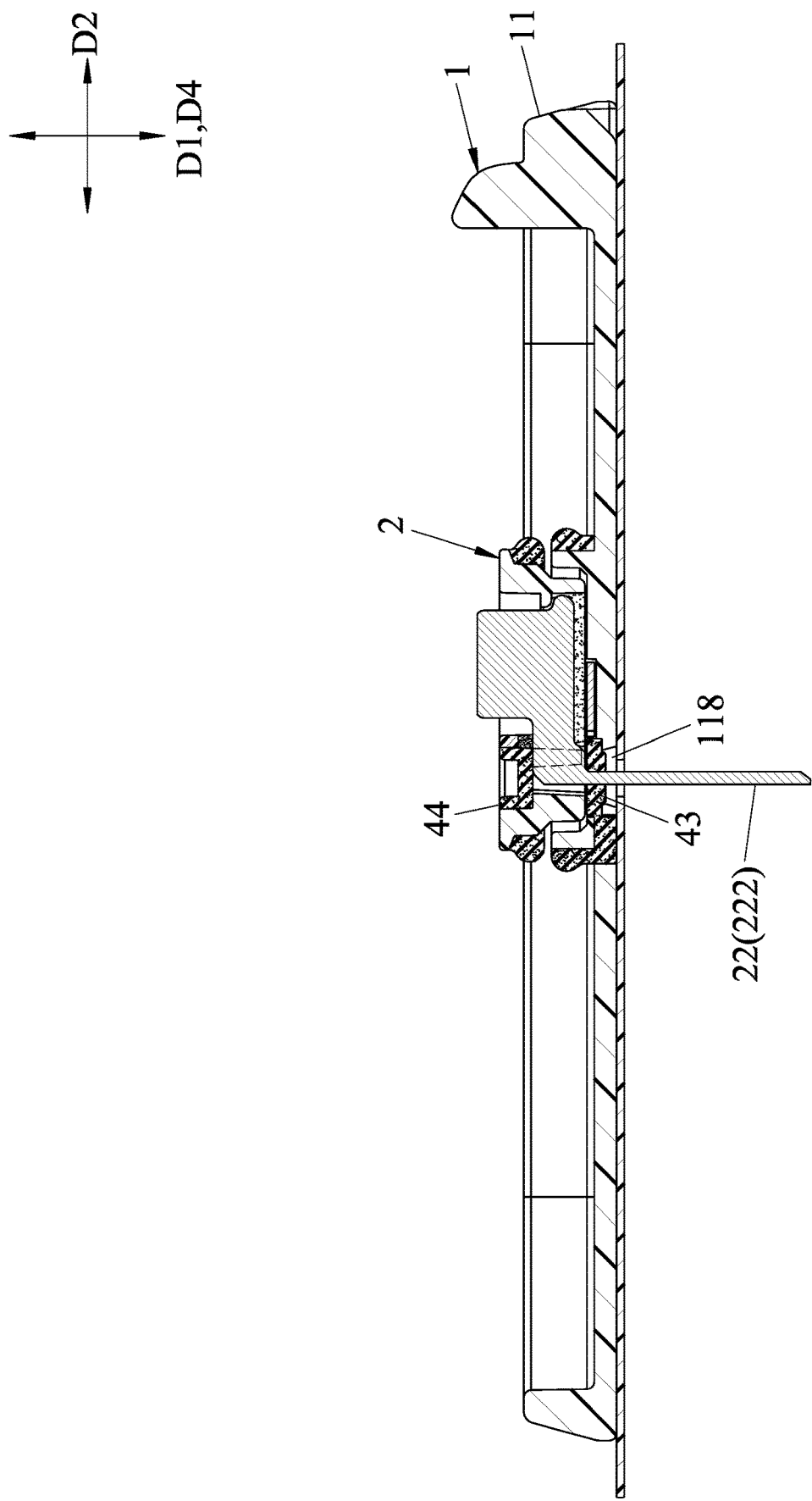

Referring to FIGS. 1 and 2, a first embodiment of a physiological signal monitoring device according to the disclosure is adapted to be mounted to a skin surface of a host (not shown) via an insertion tool 9 (see FIG. 12) of an insertion device (not shown), and is adapted for measuring at least one analytical substance of the host and for transmitting a corresponding physiological signal. In this embodiment, the physiological signal monitoring device is for measuring the glucose concentration in the interstitial fluid (ISF) of the host, and is meant to be mounted to the skin surface, but is not restricted to such. The physiological signal monitoring device includes a base 1, a biosensor 2, and a transmitter 3.

Figure 3:
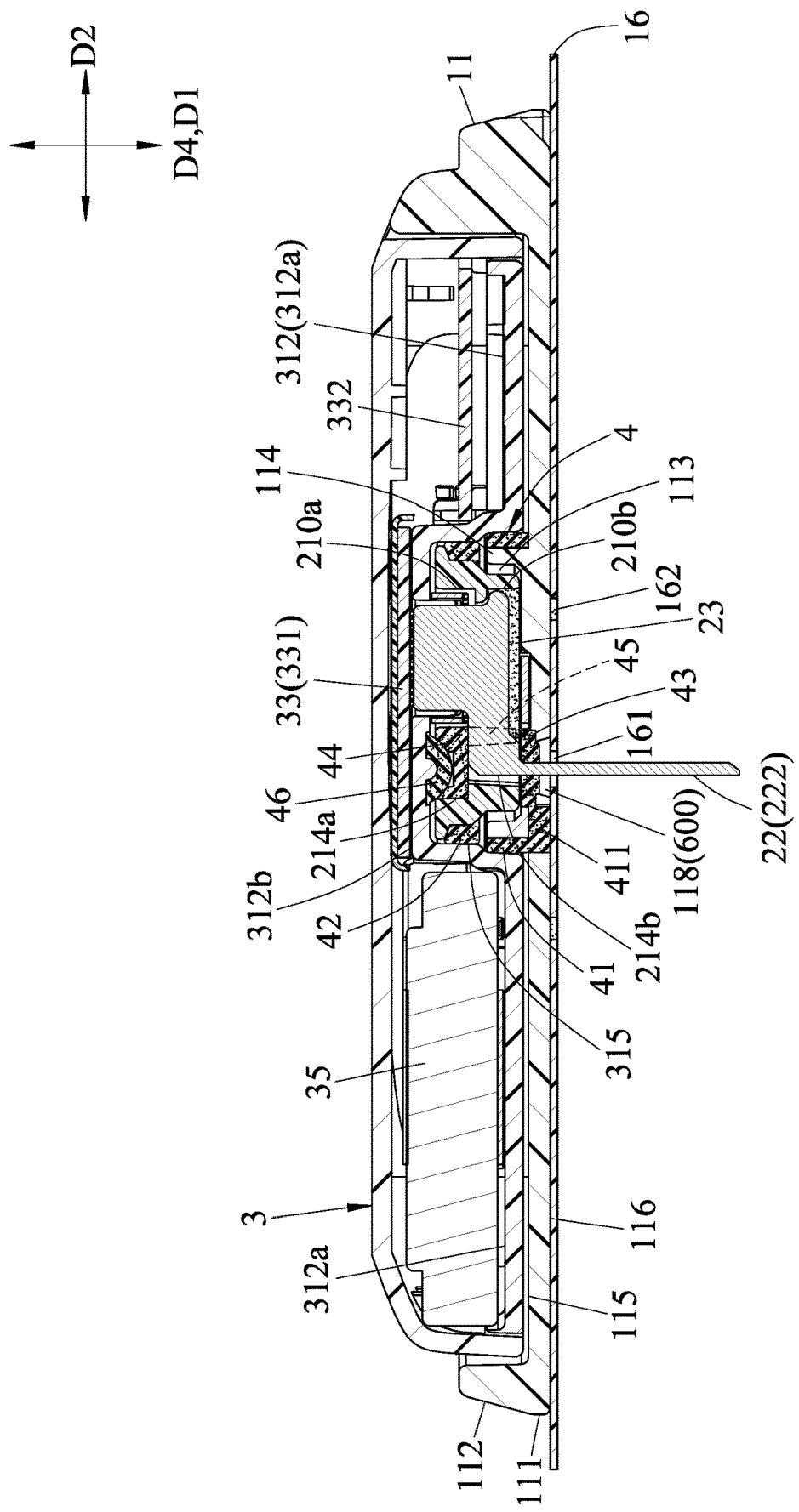
FIG. 3 is a sectional view taken along line III-III in FIG. 1.
Figure 4:
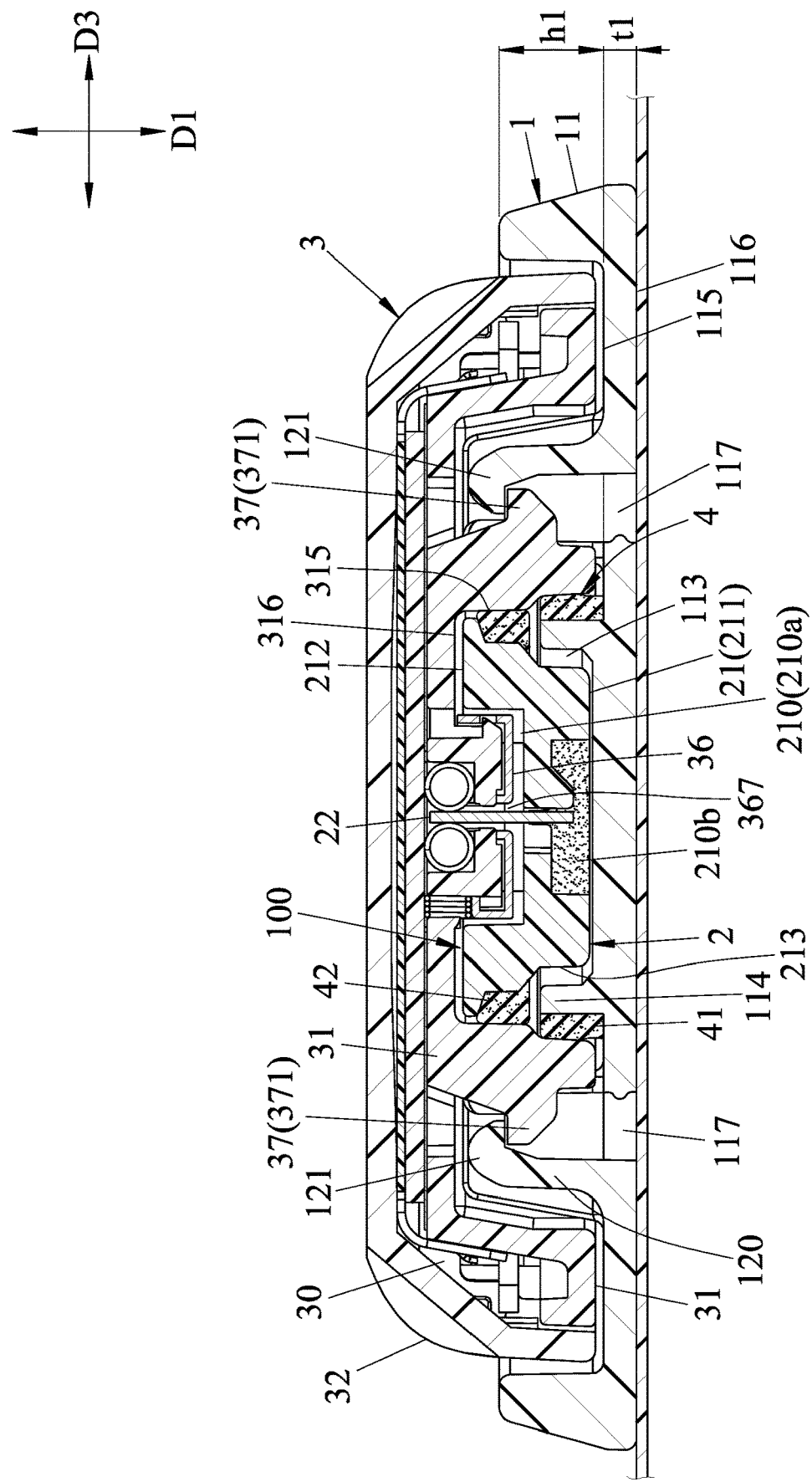
FIG. 4 is a sectional view taken along line IV-IV in FIG. 1.

Referring further to FIGS. 2, 3 and 4, the base 1 includes a base body 11 that has a bottom plate 111 adapted to be mounted to the skin surface of the host and perpendicular to a direction of a first axis (D1), and at least one first coupling structure 12 that is disposed on a top surface 115 of the bottom plate 111. The base body 11 further includes a surrounding wall 112 that extends upwardly in the direction of the first axis (D1) from a periphery of the bottom plate 111, an inner groove wall 114 that protrudes from the top surface 115 of the bottom plate 111 and that cooperates with the bottom plate 111 to define a mounting groove 113, and at least one opening 117 that extends through the bottom plate 111. The bottom plate 111 has the top surface 115, a bottom surface 116 opposite to the top surface 115 in the direction of the first axis (D1), and a through hole 118 (see FIG. 3) extending through top and bottom surfaces 115, 116 of the bottom plate 111 and communicated to the mounting groove 113. In this embodiment, the number of the openings 117 is two, and the openings 117 are spaced apart from the mounting groove 113 in a direction of a third axis (D3), which is perpendicular to the first axis (D1). A second axis (D2), which will be referenced herein, is perpendicular to both the first and third axes (D1, D3). In some embodiments, an angle between every two axes of the first, second and third axes (D1, D2, and D3) is not limited to 90 degrees.

In this embodiment, the base 1 has two of the first coupling structures 12. The first coupling structures 12 protrude from the top surface 115 of the bottom plate 111 of the base body 11, are disposed to be distal from a periphery of the base body 11, are spaced apart from the mounting groove 113 in the direction of the third axis (D3), and are respectively disposed in proximity to the openings 117. Each of the first coupling structures 12 has a base portion 120 that is connected to the top surface 115, and a first coupling portion 121 that is substantially hook-shaped, that is connected to an end of the base portion 120 distal from the top surface 115, that corresponds in position to a respective one of the openings 117, and that extends toward the respective one of the openings 117 and away from the periphery of the base body 11.

Referring to FIG. 3, the base 1 is permitted to be attached to the skin surface of the host via an adhesive pad 16. The adhesive pad 16 is mounted to the bottom surface 116 of the bottom plate 111 and has a pad hole 161 that corresponds in position to the through hole 118 of the base body 11, and a waterproof portion 162 that surrounds the pad hole 161. The waterproof portion 162 prevents contaminated liquid, which penetrates into the adhesive pad 16, from moving toward the pad hole 161 and further contaminating a wound on the skin surface and other components of the physiological signal monitoring device. In this embodiment, the adhesive pad 16 is made of nonwoven fabrics and is applied with adhesives on both sides thereof, one side being attached to the bottom surface 116 of the bottom plate 111 and the other side being attached to the skin surface of the host. In other embodiments, the adhesive pad 16 may be omitted, and the bottom plate 111 is directly adhered to the skin surface of the host. In this embodiment, the waterproof portion 162 is formed by infiltrating gum into the nonwoven fabrics.

Referring back to FIG. 2, the biosensor 2 includes amounting seat 21 that is mounted to the mounting groove 113 of the base body 11, and a sensing member 22 that is carried and limited by the mounting seat 21 and that is adapted for measuring the at least one analytical substance of the host and for sending the corresponding physiological signal to the transmitter 3. Referring to FIGS. 5 to 8, the mounting seat 21 has a bottom surface 211, a top surface 212, and an outer surrounding surface 213 that interconnects the top and bottom surfaces 212, 211, and is formed with a fitting hole 214 that extends through top and bottom surfaces 212, 211 in an inserting direction (D4). The mounting seat 21 defines amounting space 210 that is disposed between the top and bottom surfaces 212, 211 for receiving and mounting the sensing member 22 therein. The mounting space 210 and the fitting hole 214 are spaced apart from each other and fluidly communicated with each other in an extending direction (D5). An angle (θ) (see FIG. 8) is defined between the inserting direction (D4) and the extending direction (D5). In this embodiment, the inserting direction (D4) extends in the direction of the first axis (D1), and the extending direction (D5) extends in the direction of the second axis (D2), which is previously disclosed to be perpendicular to both the first and third axes (D1, D3). However, the extending and inserting directions (D5, D4) may be different in other embodiments.

Referring back to FIGS. 2 and 5, to improve stability of the biosensor 2 when it is mounted to the base body 11, the base 1 further has a hooking member 14 that is mounted to the top surface 115 of the bottom plate 111 of the base body 11, and that is disposed in the mounting groove 113. The hooking member 14 is a plate made of an elastic material, which can also be metallic, and is formed with two opposite hooked ends that are spaced apart in the direction of the third axis (D3). When the biosensor 2 is pressed toward the base 1 via an external force, the two hooked ends of the hooking member 14 initially and respectively abut against the mounting seat 21 so as to be deformed and to generate restoring force. Through the configuration between the hooking member 14 and the mounting seat 21 and the restoring force, the biosensor 2 can be easily mounted into the mounting groove 113 of the base body 11. In particular, the mounting seat 21 may be formed with two hooks 216 that are disposed between the outer surrounding surface 213 and the bottom surface 211, and that respectively correspond in position to the hooked ends of the hooking member 14. Then, once the hooked ends of the hooking member 14 are pressed toward even further to be respectively coupled to the hooks 216, the restoring force in turn act as a gripping force to fixedly mount the biosensor 2 to the base 1.

Figure 33:
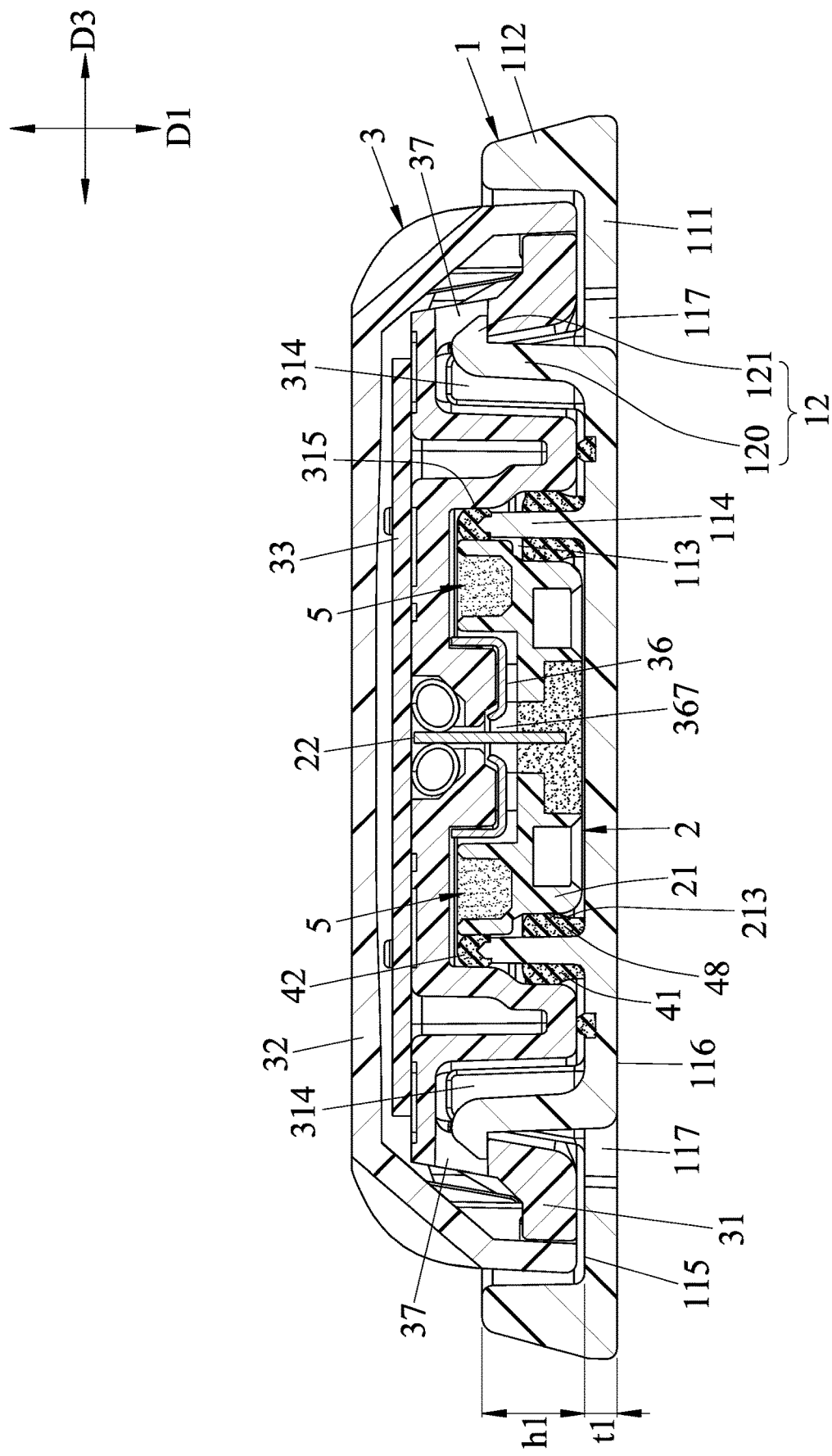
FIG. 33 is a sectional view of the fourth embodiment that is similar to FIG. 4.
Figure 34:
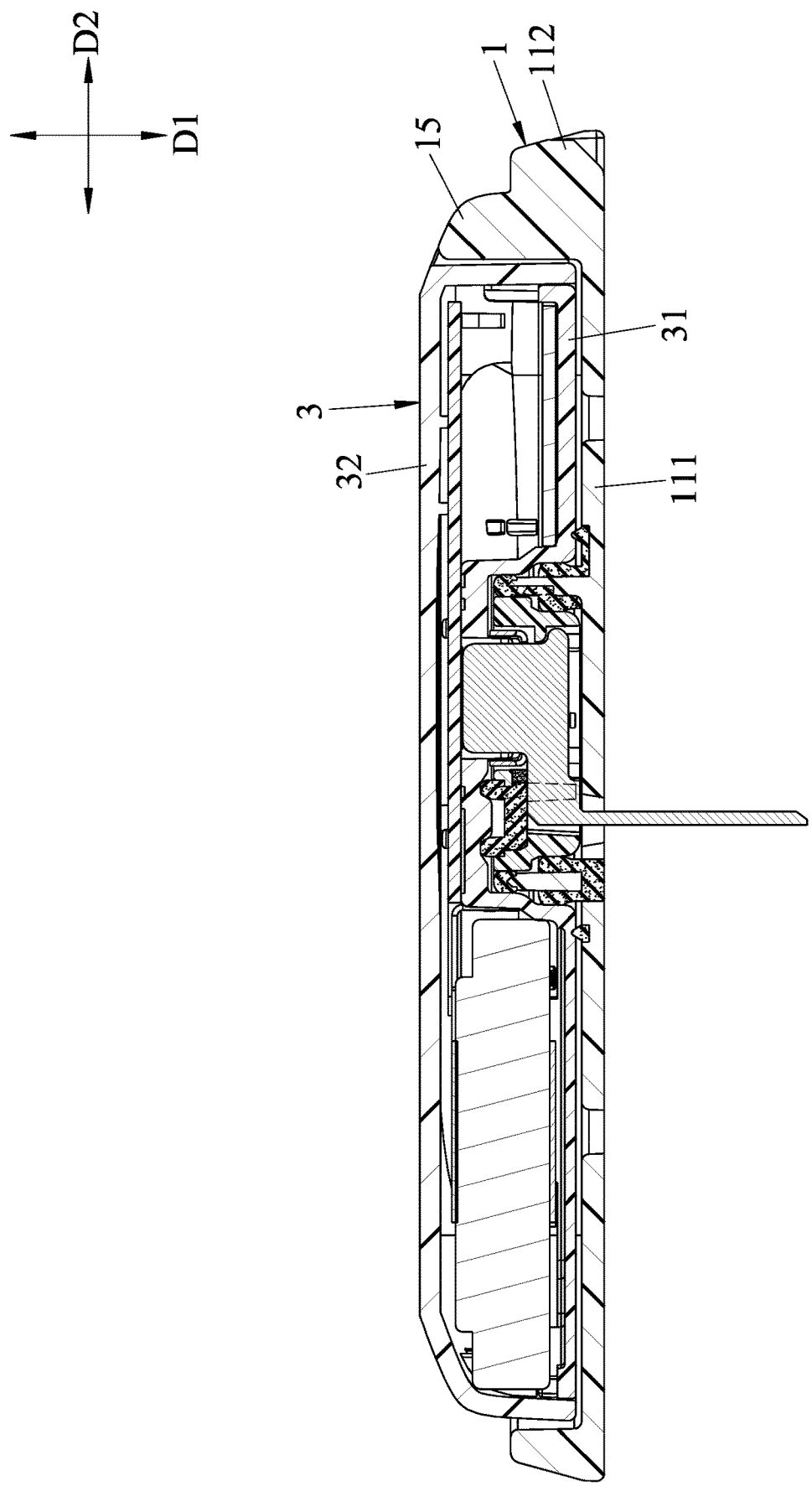
FIG. 34 is a sectional view of the fourth embodiment that is similar to FIG. 3.

However, there are other ways for the mounting seat 21 of the biosensor 2 to be fixedly mounted to the base 1 as well, and the hooking member 14 may be omitted. For example, the mounting seat 21 may be directly adhered to the base body 11 via an adhesive applied to a bottom surface of the mounting groove 113, or/and implementation of a resilient member 48 (see FIGS. 33 and 36), which is preferably made of a rubber material. Specifically, when the mounting seat 21 is mounted to the mounting groove 113, the resilient member 48 is clamped between an inner peripheral surface of the inner groove wall 114 of the base 1 and the outer surrounding surface 213 of the mounting seat 21, such that the outer surrounding surface 213 abuts against the resilient member 48 for the mounting seat 21 to be fixedly mounted to the mounting groove 113.

Figure 9:
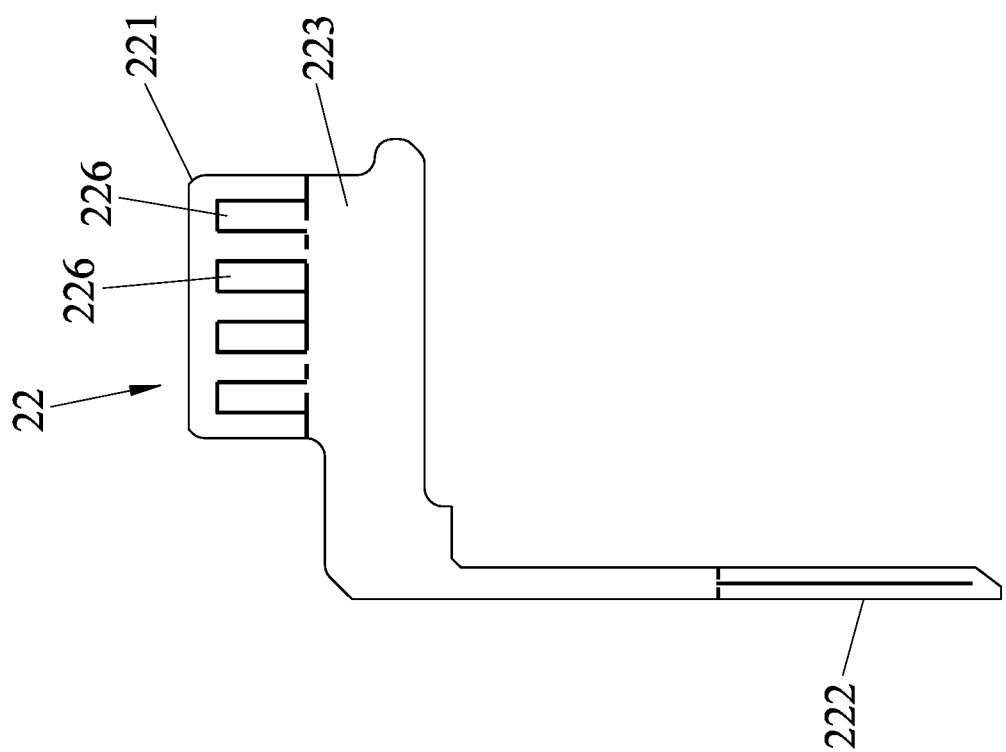
FIG. 9 is a side view of a sensing member of the biosensor of the first embodiment.

Referring further to FIG. 9, the sensing member 22 has a sensing section 222, a signal output section 221 and an extended section 223 that is adapted to interconnect the sensing section 222 and the signal output section 221. The sensing section 222 is adapted to be inserted underneath the skin surface of the host for measuring the physiological signal corresponding to the physiological parameter of the at least one analytical substance of the host, and the signal output section 221 is electrically connected to the transmitter 3 for transmitting the corresponding physiological signal to the transmitter 3 after receiving information from the sensing section 222 via the extended section 223. The extended section 223 is covered with an insulating material. In addition, numbers and types of electrodes disposed on the sensing member 22 is primarily designed to account for the type of analytical substances measured, and is not restricted to the one shown in the disclosure. For the sake for clarity, detailed structures of the sensing member 22 is only showcased in FIG. 9.

Figure 8:
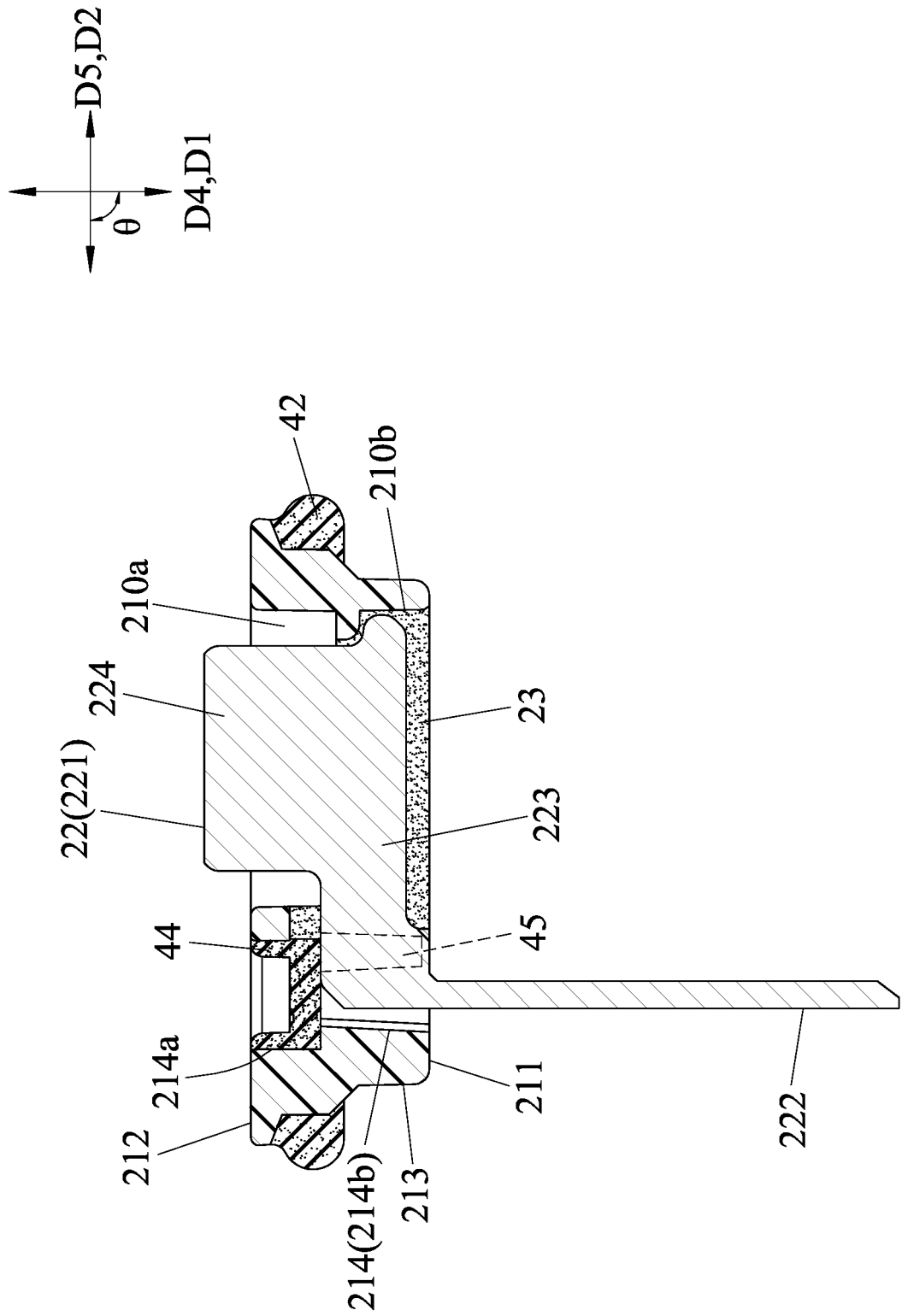
FIG. 8 is a sectional view of the biosensor of the first embodiment.

Referring to FIGS. 3, 8 and 9, the mounting space 210 of the mounting seat 21 has a cavity portion 210a that is open to the top surface 212, and a crevice portion 210b that is communicated to the cavity portion 210a in the direction of the first axis (D1). When the sensing member 22 is mounted to the mounting seat 21, the signal output section 221 of the sensing member 22 is disposed in the cavity portion 210a and extends through the top surface 212 of the mounting seat 21 in the direction of the first axis (D1). The extended section 223 of the sensing member 22 extends through the crevice portion 210b in the extending direction (D5), and then extends downwardly through the fitting hole 214 in the inserting direction (D4) to be connected to the sensing section 222. In order for the sensing member 22 to measure the analytical substance, either the sensing section 222 or the sensing section 222 and a portion of the extending section 223 of the sensing member 22 extend through the bottom surface 116 of the base body 11 via the through hole 118 to be inserted underneath the skin surface of the host.

The fitting hole 214 of the mounting seat 21 and the through hole 118 of the base body 11 cooperatively define an implantation path 600 (see FIG. 3) that extends in the inserting direction (D4) and that is for the insertion tool 9 (see FIG. 12) to extend therethrough, so as to insert the sensing section 222 and a portion of the extending section 223 of the sensing member 22 underneath the skin surface of the host.

Referring back to FIGS. 2 to 5, the transmitter 3 is removably mounted (e.g., removably covered) to the base body 11 of the base 1 and connected to the biosensor 2 for receiving and sending the physiological signal. The transmitter 3 includes a bottom casing 31 facing the top surface 115 of the bottom plate 111 of the base body 11, a top casing 32 that cooperates with the bottom casing 31 to define an inner space 30, a circuit board 33 that is disposed in the inner space 30, a battery 35 that is disposed in the inner space 30 and that is electrically connected to the circuit board 33, a connection port 36 that is connected to a bottom surface of the circuit board 33 and that extends outwardly from the inner space 30 toward the base body 11, and at least one second coupling structure 37 that is disposed on the bottom casing 31 and that corresponds in position to the at least one first coupling structure 12 of the base 1.

Figure 5:
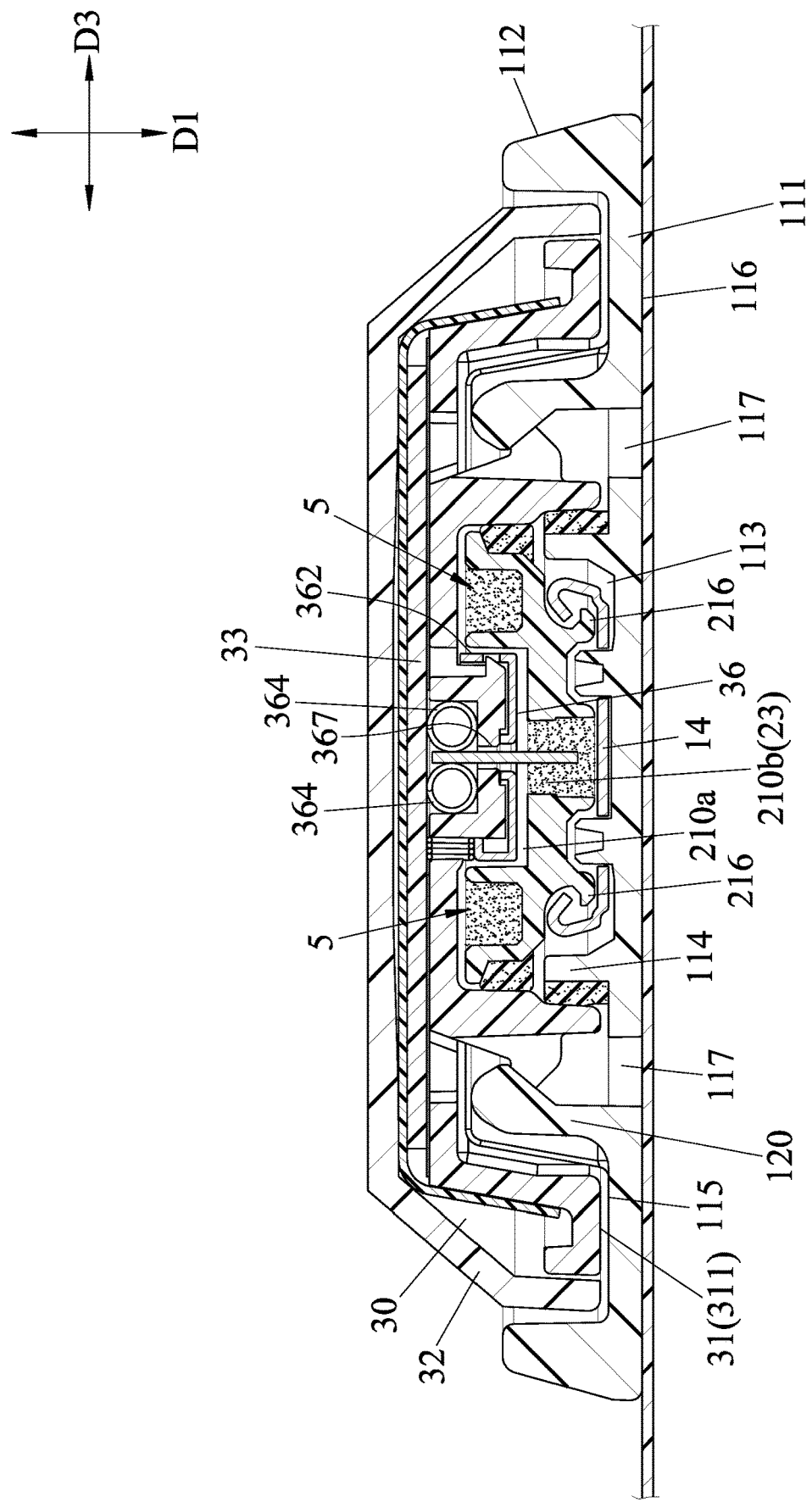
FIG. 5 is a sectional view taken along line V-V in FIG. 1.
Figure 10:
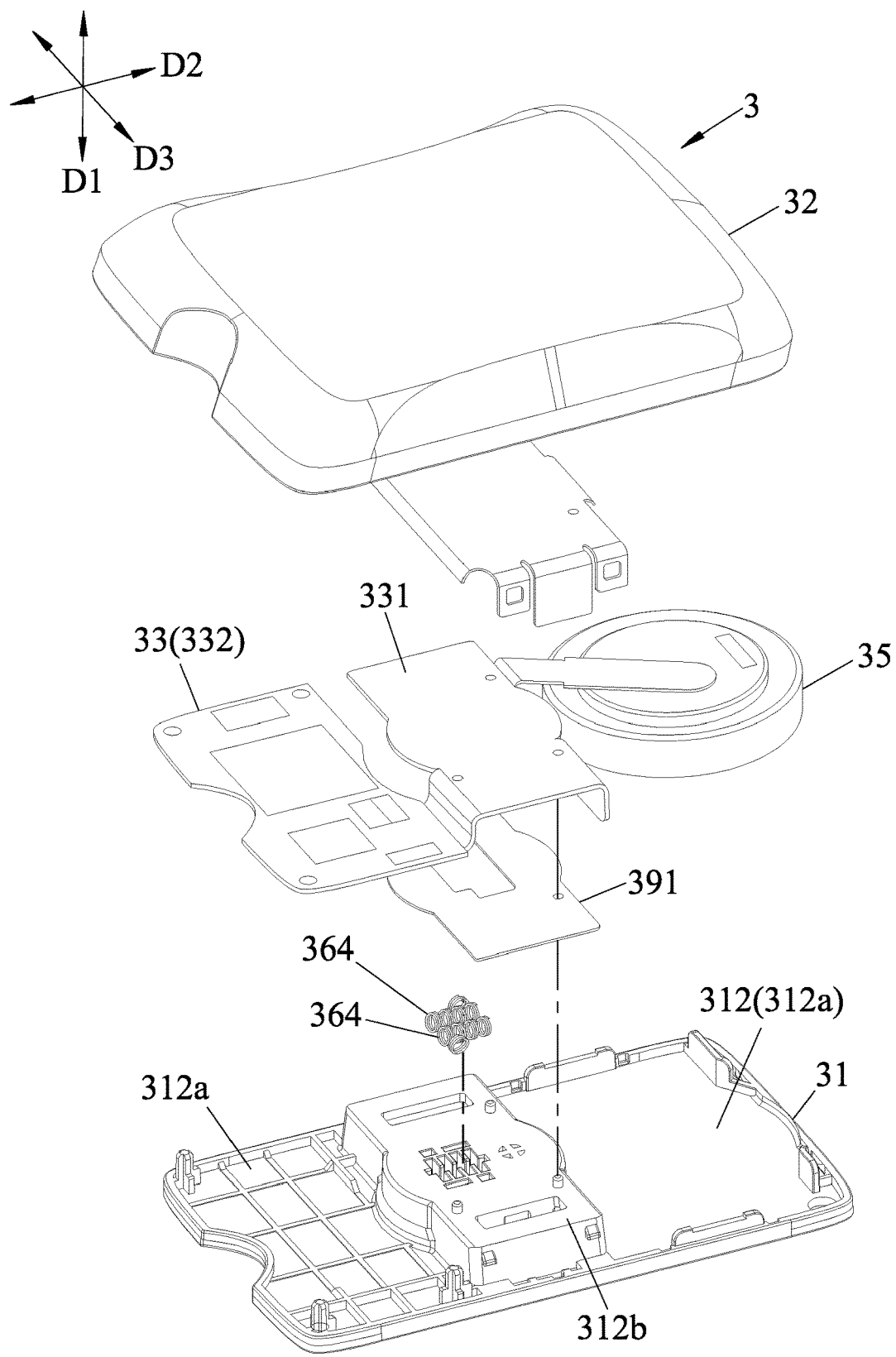
FIG. 10 is an exploded perspective view of a transmitter of the first embodiment.
Figure 11:
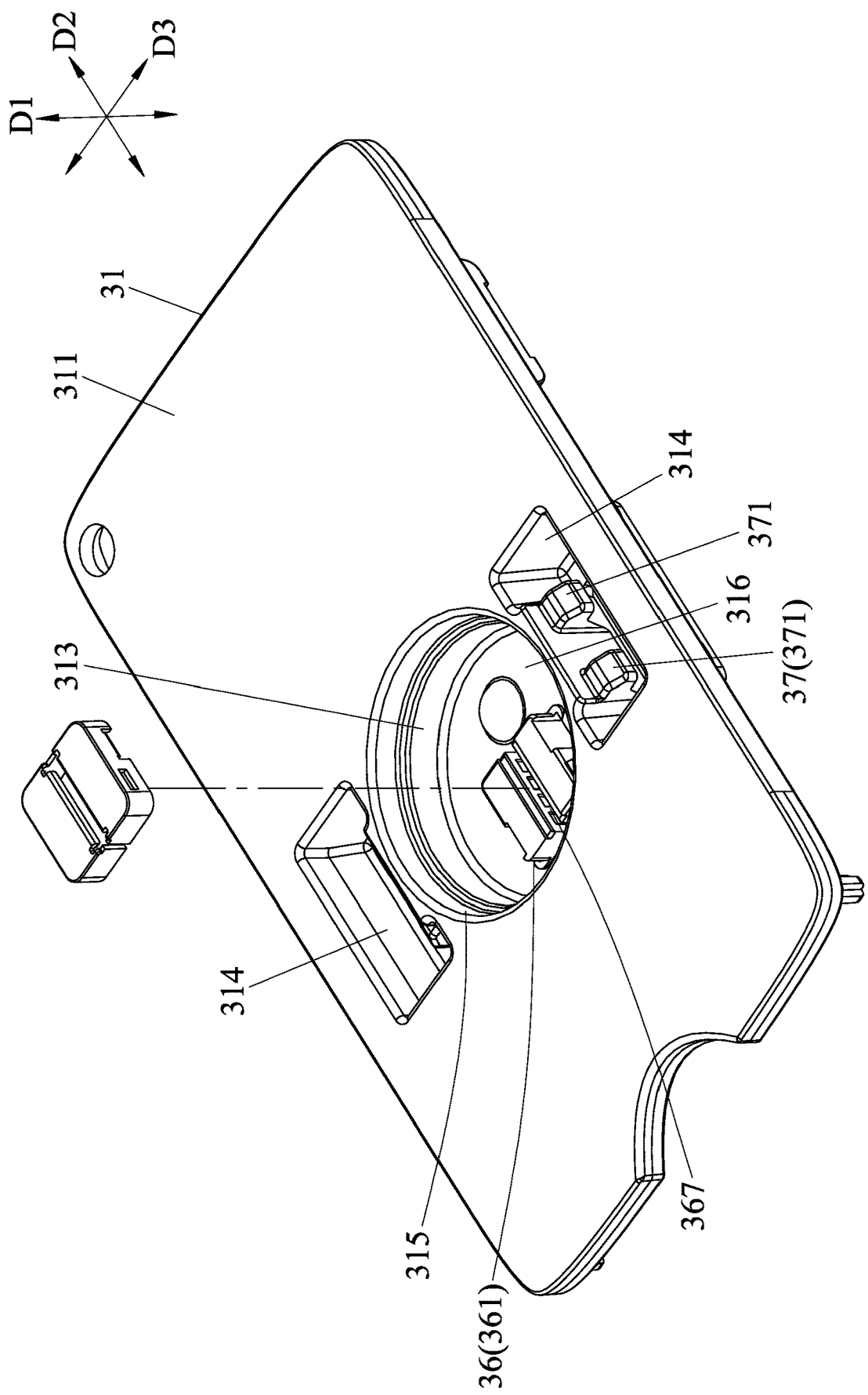
FIG. 11 is an exploded perspective view of a bottom casing and a connection port of the first embodiment.

Referring to FIGS. 5, 10 and 11, the bottom casing 31 includes a bottom surface 311, a top surface 312, a first groove 313 that indents from the bottom surface 311, and at least one second groove 314 that indents from the bottom surface 311 and that corresponds in position to the at least one first coupling structure 12. The first groove 313 is defined by a groove surrounding surface 315 that is connected to the bottom surface 311 and a groove bottom surface 316 that is connected to the groove surrounding surface 315. In this embodiment, the number of the second coupling structures 37 is two, and the number of the second groove 314 is two as well. When the transmitter 3 covers to the base 1, the bottom surface 311 abuts against the bottom plate 111 of the base body 11, the first groove 313 receives the inner groove wall 114 of the base body 11 and the biosensor 2 therein, and each of the second grooves 314 receives a respective pair of the first and second coupling structures 12, 37 therein, thereby reducing the overall thickness of the disclosure.

The circuit board 33 includes a signal transmission module (not shown) for receiving and sending the physiological signal measured by the sensing member 22. As the signal transmission module is well known in the art and may be internally rearranged to fit different needs, details thereof are omitted for the sake of brevity. Nevertheless, the signal transmission module may include a combination of a signal amplifier, an analog-digital signal converter, a processor, and a transmitter.

Specifically, referring back to FIGS. 3 and 10, the top surface 312 of the bottom casing 31 has two first stepped portions 312*a* that face the top casing 32 and that are spaced apart in the direction of the second axis (D2), and a second stepped portion 312*b* that faces the top casing 32 and that is disposed between the first stepped portions 312*a*. The second stepped portion 312*b* corresponds in position to the first and second grooves 313, 314 (see FIG. 11) in the direction of the first axis (D1), and is more proximate to the top casing 32 relative to the first stepped portions 312*a* in the direction of the first axis (D1). The circuit board 33 is designed to be in conformity with the shape of the bottom casing 31, and includes a connecting section 331 that corresponds in position to the second stepped portion 312*b* and that is electrically connected to the sensing member 22, and an electronic section 332 that is disposed between one of the first stepped portions 312*a* and the top casing 32 and that is for mounting components of the signal transmission module thereon. The battery 35 is disposed between the other one of the first stepped portions 312*a* and the top casing 32, and is connected to the connecting section 331 of the circuit board 33. By distributing the abovementioned components evenly within the inner space 30, the transmitter 3 may be designed to be more compact with smaller thickness in the direction of the first axis (D1).

Figure 6:
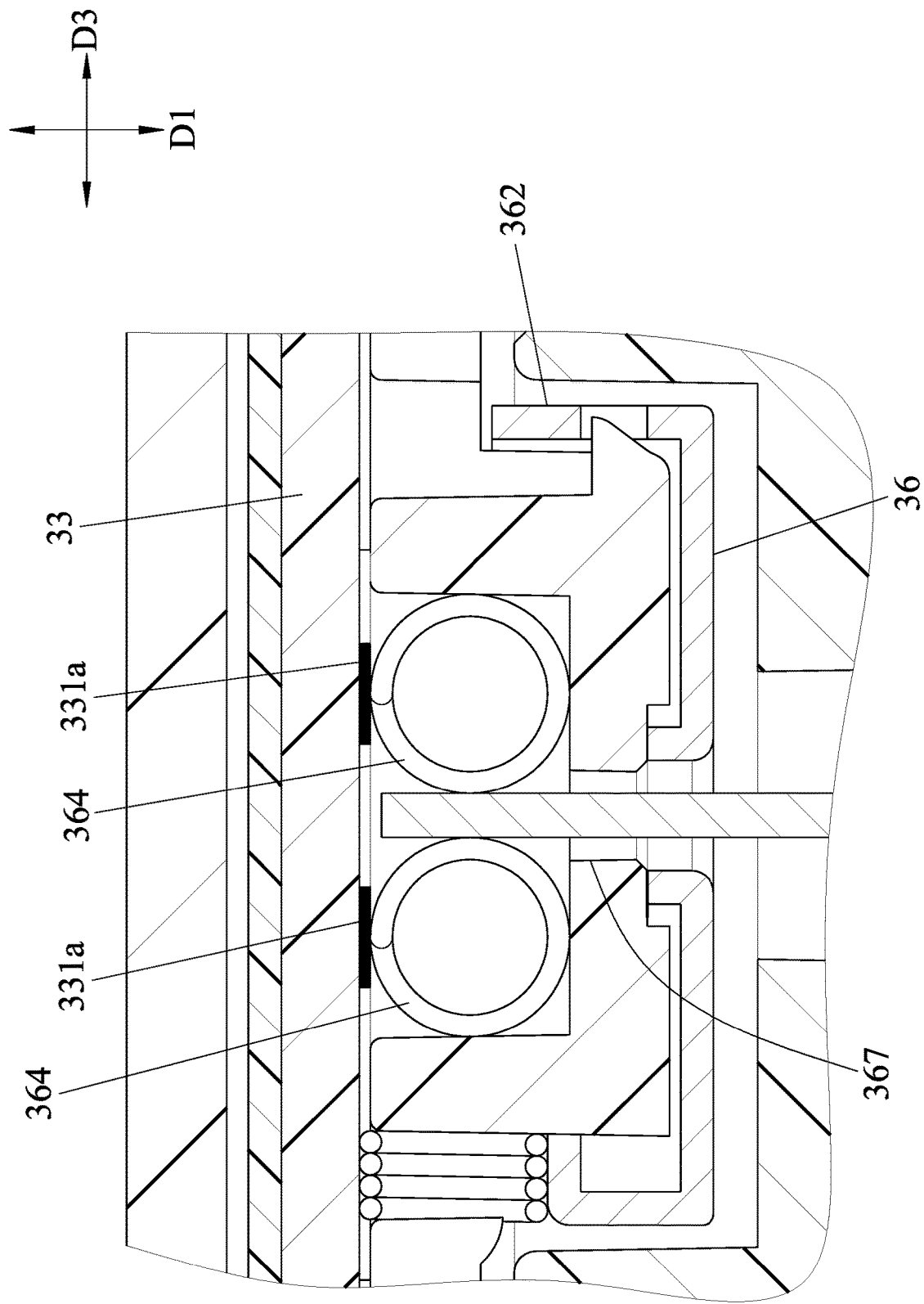
FIG. 6 is a fragmentary and enlarged sectional view of a connection port in FIG. 5.
Figure 7:
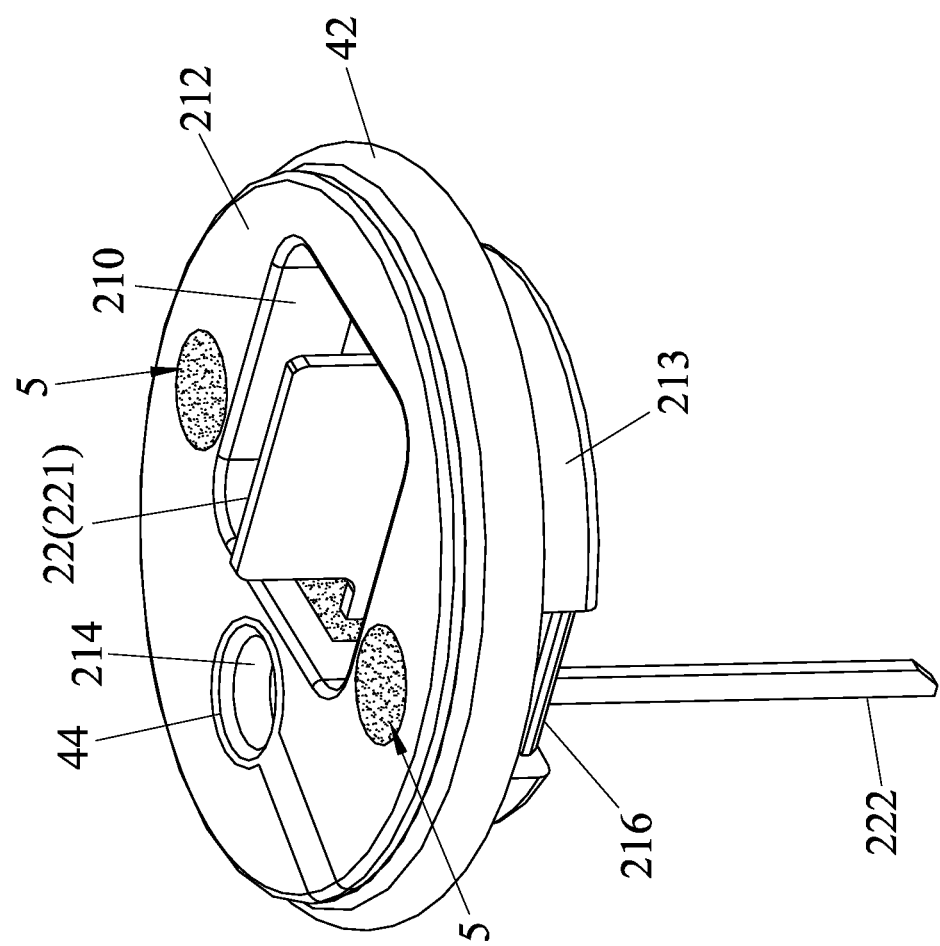
FIG. 7 is a perspective view of a biosensor of the first embodiment.

Referring back to FIGS. 2 and 5, the connection port 36 is connected to a bottom surface of the circuit board 33, protrudes downwardly in the direction of the first axis (D1) into the first groove 313 of the bottom casing 31, and includes a socket 367 that is for the signal output section 221 of the sensing member 22 to be inserted thereinto to permit electric connection between the sensing member 22 and the circuit board 33. In this embodiment, the sensing member 22 is electrically connected to the circuit board 33 via a plurality of conducting members 364 disposed in the connection port 36. Referring specifically to FIG. 6, the conducting members 364 are helical springs, respectively abut along a radial direction thereof against a plurality of electrical contacts 331*a* of the circuit board 33, and abut along the radial direction thereof against several outputs of electrodes 226 (see FIG. 9) on the signal output section 221 of the sensing member 22.

Figure 14:
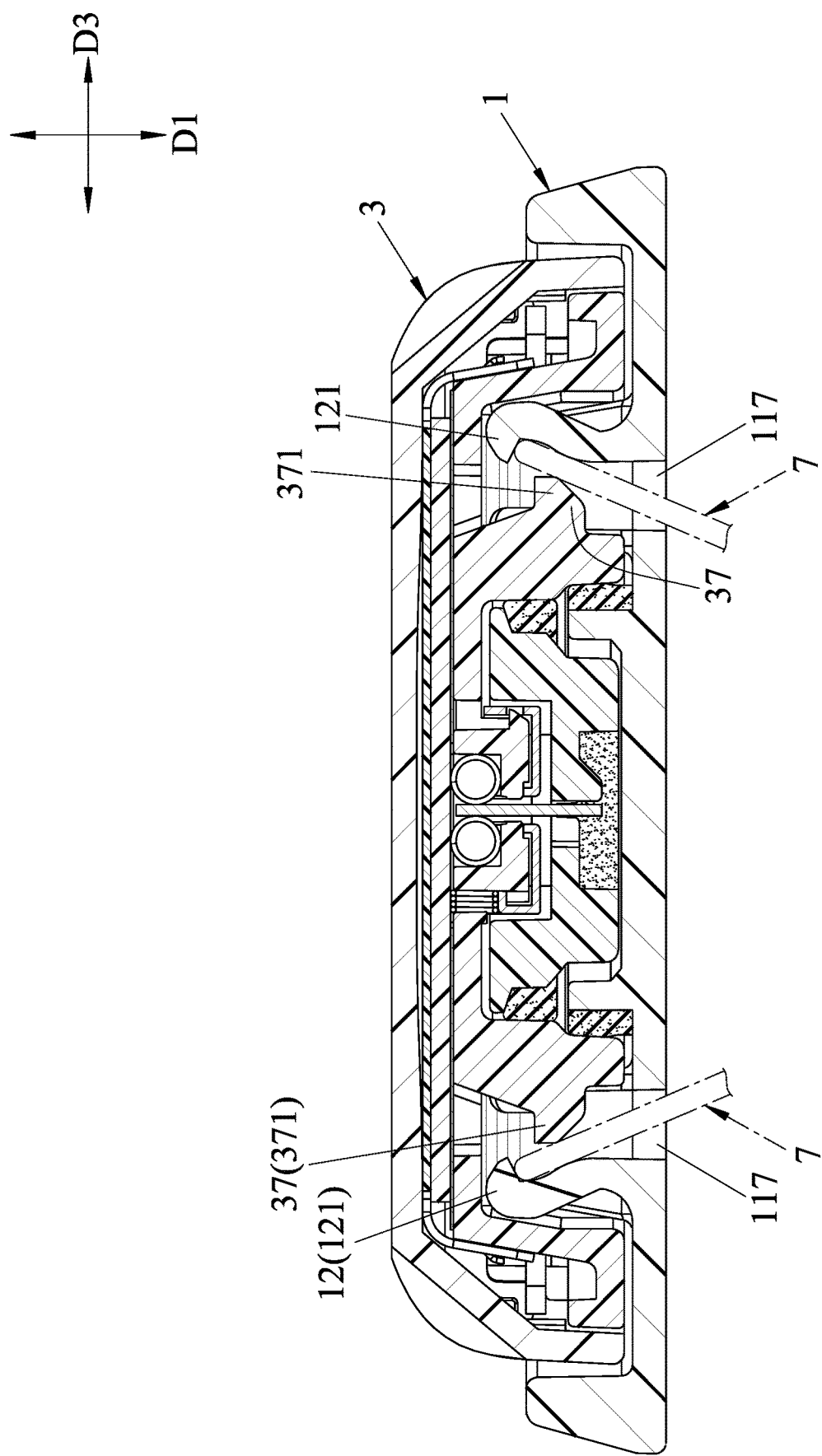
FIG. 14 is a view similar to FIG. 4, illustrating first coupling structures of the base and second coupling structures of the transmitter being uncoupled from each other.

Referring back to FIG. 11, each of the second coupling structures 37 has at least one second coupling portion 371 that is substantially hook-shaped. In this embodiment, each of the second coupling structures 37 has two of the second coupling portions 371 spaced apart from each other in the direction of the second axis (D2). Referring back to FIG. 4 in conjunction with FIG. 11, the second coupling portions 371 of the second coupling structures 37 correspond in position and in shape to the first coupling portions 121 of the first coupling structures 12 and are permitted to be removably coupled thereto. When the transmitter 3 is mounted to the base body 11 of the base 1 while the bottom casing 31 of the transmitter 3 faces the top surface 115 of the bottom plate 111 of the base body 11, the first and second coupling structures 12, 37 are coupled to each other. Specifically, each of the first coupling portions 121 is coupled with the second coupling portions 371 of a respective one of the second coupling structures 37 in a direction toward a corresponding one of the openings 117. As the first and second coupling structures 12, 37 respectively protrude from the top surface 115 of the base body 11 and the bottom casing 31 of the transmitter 3, components disposed in the inner space 30 of the transmitter 3 are distal therefrom and are not damaged when the transmitter 3 is mounted to the base 1. Referring to FIG. 14, the first and second coupling structures 12, 37 are uncoupled from each other when an external force is applied through the openings 117 to thereby separate the transmitter 3 from the base 1.

Referring back to FIGS. 2 and 10, to ensure that a user is able to mount the transmitter 3 to the base 1 properly, the base 1 further includes a first aligning structure 15 that is disposed at a side of the base body 11, and the transmitter 3 further includes a second aligning structure 38 that is disposed at a side thereof and that fits with (i.e., fittingly and separably engages with) the first aligning structure 15. In this embodiment, the first aligning structure 15 protrudes from the surrounding wall 112, and the second aligning structure 38 indents from a periphery of the transmitter 3 (i.e., including a periphery of the top casing 32 and a periphery of the bottom casing 31). When the transmitter 3 is mounted to the base 1, the first and second aligning structures 15, 38 fittingly engage with one another. In other embodiments, the second aligning structure 38 protrudes from the periphery of the top casing 32 or the periphery of the bottom casing 31, and the first aligning structure 15 indents from the surrounding wall 112 to fittingly engage the second aligning structure 38. Since the first and second aligning structures 15, 38 are directly formed on the periphery of the base 1 and the periphery of the transmitter 3 so as to be externally visible, when the user attempts to couple the transmitter 3 to the base 1, the user is less likely to install the device incorrectly.

Since the base 1, the biosensor 2, and the transmitter 3 are all detachable to each other, in addition to the implantation path 600, internal components of the physiological signal monitoring device, such as the sensing member 22 of the biosensor 2 and the components disposed in the inner space 30 of the transmitter 3, are susceptible to leakage of external liquid thereinto, which can easily tamper with the measuring capability of the sensing member 22 and transmitting capability of the signal transmission module. The body and external liquids may flow toward the sensing member 22 and the inner space 30 of the transmitter 3 via a plurality of fluid pathways (a, b, c, d, e) as indicated by arrows in FIGS. 15 and 16, where the fluid pathways (a, b, c) are proximate to the implantation path 600 and the wound on the skin surface, where the fluid pathway (d) is proximate to a gap between the transmitter 3 and the surrounding wall 112 of the base body 11, and where the fluid pathways (e) are respectively proximate to the openings 117 (see FIG. 4) of the base body 11. Furthermore, the external liquid may flow from the fluid pathways (d, e) toward the implantation path 600 through the remaining fluid pathways (a, b, c) to contaminate the wound on the skin surface as well. To prevent liquid leakage within the physiological signal monitoring device, the physiological signal monitoring device further includes a sealing unit 4 that is for sealing the abovementioned fluid pathways (a, b, c, d, e).

Referring back to FIGS. 3 and 4, the sealing unit includes a first sealing member 41 that is peripherally clamped between the inner groove wall 114 of the base body 11 and the groove surrounding surface 315 of the transmitter 3, a second sealing member 42 that is peripherally clamped between outer surrounding surface 213 of the mounting seat 21 and the groove surrounding surface 315, a third sealing member 43 that is mounted to the through hole 118 of the base body 11, a fourth sealing member 44 that is mounted to a top portion 214a of the fitting hole 214 of the mounting seat 21 and that seals the fitting hole 214, a blocking member 45 that is disposed for blocking the communication between the fitting hole 214 and the mounting space 210 in the extending direction (D5), and a urging member 46 that is disposed at the bottom casing 31 of the transmitter 3 and that is tightly coupled to the fourth sealing member 44. In this embodiment, all components of the sealing unit 4 are made of rubber materials, but may be made of other elastic materials capable of preventing fluid leakage in other embodiments.

Figure 15:
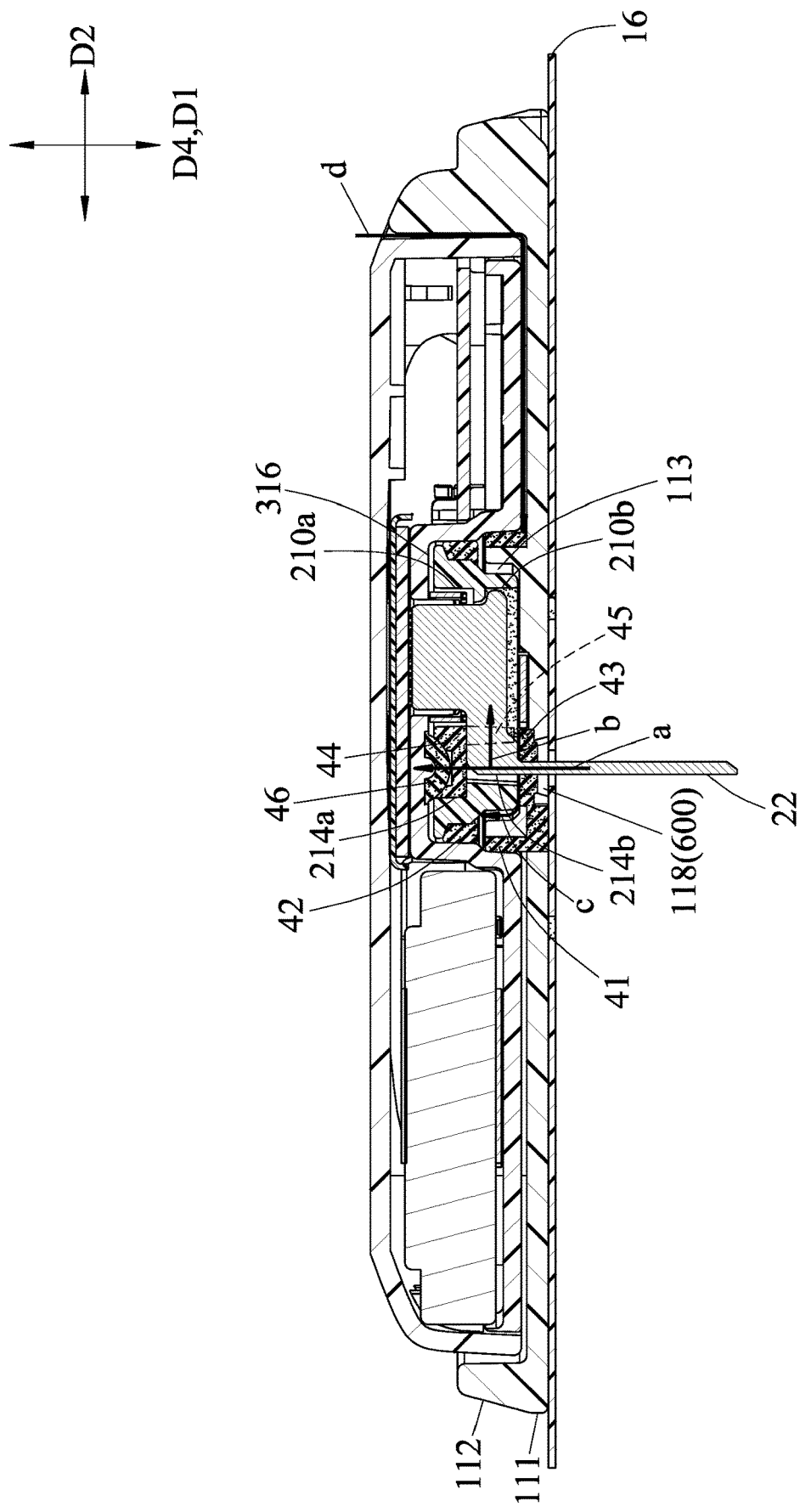
FIG. 15 is a view similar to FIG. 3, illustrating a plurality of fluid pathways prone to external liquid leakage.
Figure 16:
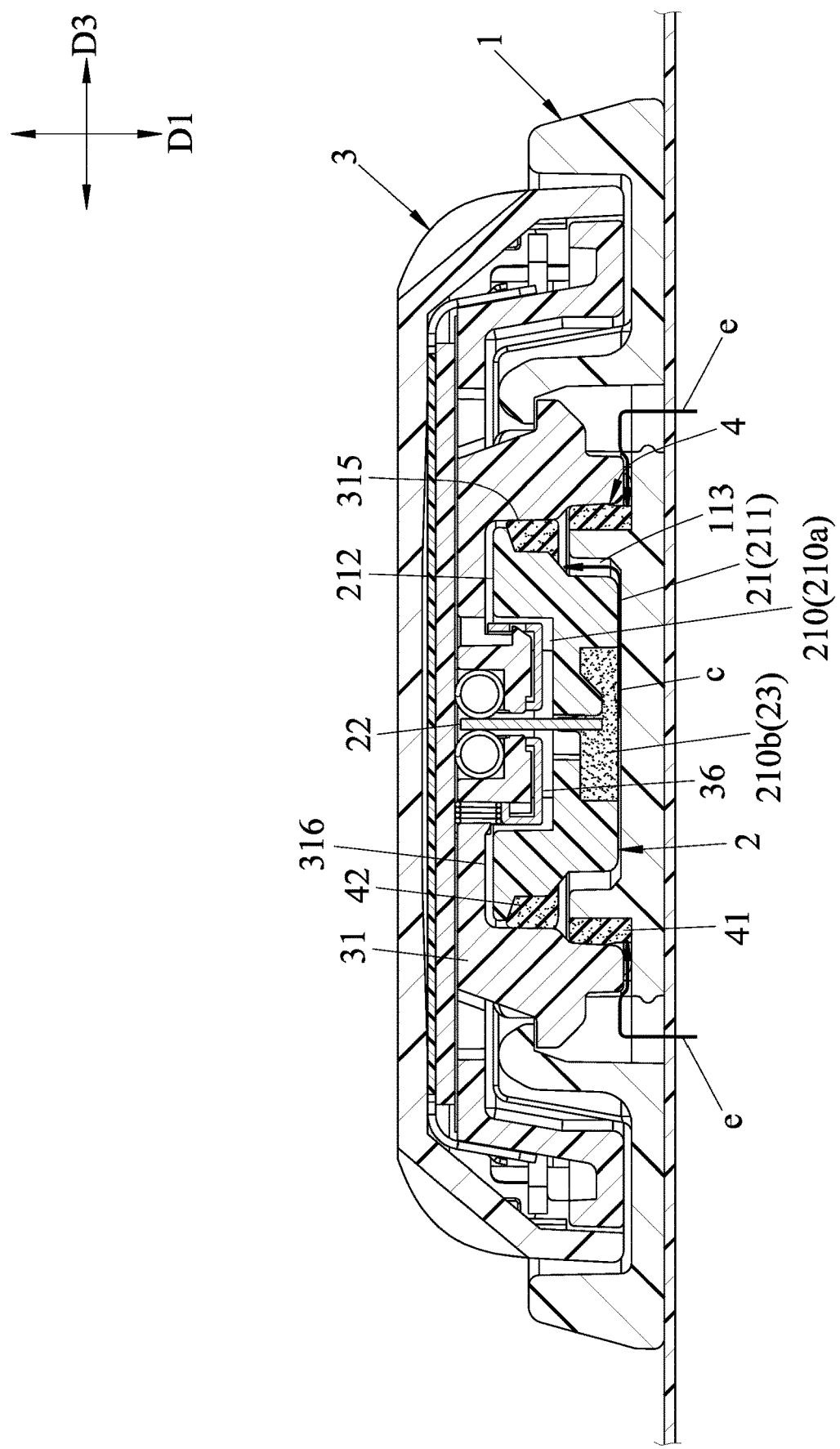
FIG. 16 is a view similar to FIG. 4, illustrating a plurality of fluid pathways prone to external liquid leakage.

Referring to FIGS. 15 and 16 in conjunction with FIGS. 3 and 5, the first sealing member 41 seals a gap between the inner groove wall 114 of the base body 11 and the groove surrounding surface 315 of the transmitter 3 to prevent leakage of the external liquid (especially contaminated liquid) into the inner space 30 of the transmitter 3 from the fluid pathways (d, e) (i.e., from the gap between the transmitter 3 and the surrounding wall 112 of the base body 11 or from the openings 117 of the base body 11) through a gap between the groove bottom surface 316 of the transmitter 3 and the top surface 212 of the mounting seat 21 and subsequently through the socket 367 of the connection port 36, and to prevent leakage of the external liquid into the wound on the skin surface from the fluid pathways (d, e) through the remaining fluid pathways (a, b, c) as well. On the other hands, body liquid coming out of the wound, such as blood, will scare the user before the assembling of the transmitter 3 and can be prevented from leaking out of the physiological signal monitoring device through the through hole 118 of the base 1 toward a gap between the mounting seat 21 and the base body 11 (also noted as the fluid pathway (c) in FIG. 15) and subsequently through the fluid pathway (d).

The second sealing member 42 seals a gap between the transmitter 3 and the mounting seat 21 of the biosensor 2 to prevent leakage of the external liquid (especially contaminated liquid) into the inner space 30 of the transmitter 3 from the fluid pathways (d, e) through the gap between the groove bottom surface 316 of the transmitter 3 and the top surface 212 of the mounting seat 21 and subsequently through the socket 367 of the connection port 36. On the other hands, the body liquid coming out of the wound (especially blood) is prevented from leaking into the gap between the groove bottom surface 316 of the transmitter 3 and the top surface 212 of the mounting seat 21 from the through hole 118 of the base 1 through the fluid pathways (a, c) via the gap between the mounting seat 21 and the base body 11 (the fluid pathway (c) in FIG. 15). Specifically, in this embodiment, the second sealing member 42 acts as a backup member against leakage of the contaminated liquid from the fluid pathways (d, e) in a case where the first sealing member 41 fails to prevent the external liquid from passing therethrough.

Referring to FIGS. 3, 12, 13, 15 and 16, the third sealing member 43 seals an end of the through hole 118 of the base body 11 distal from the host and is formed with a premade hole 431 for the insertion tool 9 to pass therethrough so as to reduce the resistance of the implantation. In other embodiments, the third sealing member 43 can be directly punctured therethrough by the insertion tool 9 and guide the sensing member 22 so that the premade hole 431 can be omitted. In such embodiments, the third sealing member 43 is made of an elastic material such as rubber, and abuts against the sensing member 22 to fluid-tightly seals the internal components of the physiological signal monitoring device after the insertion tool 9 is drawn out from the host. In addition, referring specifically to FIGS. 3 and 4, the mounting seat 21 is permitted to be further sealed at its bottom with a glue 23 to block the body liquid coming out of the would from leaking into the internal components of the physiological signal monitoring device through the fluid pathway (a). In other embodiments, implementation of the glue 23 may be sufficient enough for sealing, such that the third sealing member 43 may be omitted.

In this embodiment, the fourth sealing member 44 is indented with a groove on a top surface thereof for the urging member 46 to be tightly coupled thereto.

When the insertion tool 9 is pierced through the skin surface of the host, blood from the host instantaneously expel out of the wound and into the physiological signal monitoring device through the implantation path 600 (also noted as the fluid pathway (a) in FIG. 15). Since the sensing section 222 of the sensing member 22 remains beneath the skin surface of the host during the use of the physiological signal monitoring device, the blood will keep flowing out from the wound, albeit at a slower rate. With that in mind, by sealing the through hole 118 of the base body 11 and the fitting hole 214 of the mounting seat 21 via the third and fourth sealing members 43, 44 respectively, and by tightly coupling the fourth sealing member 44 with the urging member 46, three layers of defensive measures against leakage of the body fluid are formed along the implantation path 600 to prevent the blood flowing out from the wound from leaking into the transmitter 3 through the implantation path 600. In other embodiments, the fourth sealing member 44 may be omitted, and the urging member 46 is tightly coupled to the top portion 214a of the fitting hole 214 directly to seal the fitting hole 214 instead (see FIG. 18).

In addition, as the third sealing member 43 seals an end of the through hole 118 of the base body 11 distal from the host, the other end of the through hole 118 is permitted for containing the blood released from the host, such that the blood is given enough open space to relieve pressure, so that the blood would not be able to flow through any potential gap between the third sealing member 43 and the sensing member 22 due to high pressure.

Figure 17:
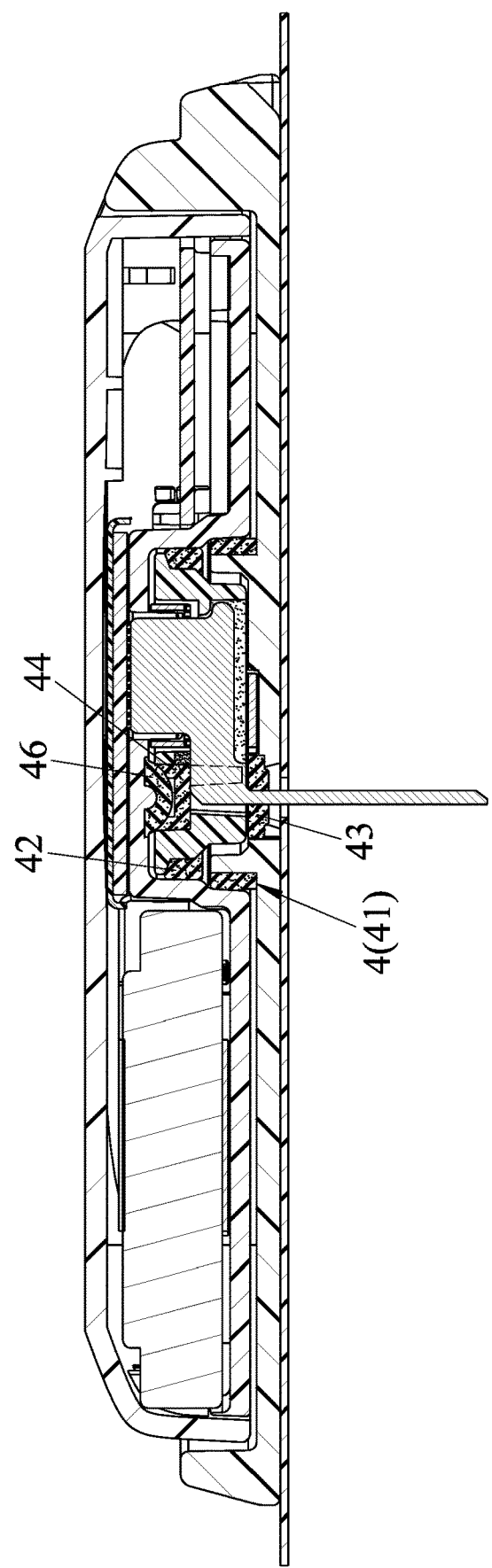
FIGS. 17 to 22 are views similar to FIG. 3, illustrating various modifications of the first embodiment.

Furthermore, referring back to FIGS. 2 and 3, the first and third sealing members 41, 43 of this embodiment are injection molded to be formed as a single piece coupled to the base body 11. To be specific, in this embodiment, an elastic material is injected to surround the inner groove wall 114 of the base body 11 so as to form the first sealing member 41. The elastic material further flows downwardly so as to form a connecting portion 411 that extends downwardly from the first sealing member 41. The elastic material further flows upwardly to surround the through hole 118 so as to form the third sealing member 43. In this embodiment, the connecting portion 411 is engaged with the bottom plate 111, and extends through the bottom plate 111 to abut against the adhesive pad 16 or the skin surface of the host. The connecting portion 411 may be flush with or protrude from the bottom surface 116 of the bottom plate 111. Similar to the waterproof portion 162 of the adhesive pad 16, the connecting portion 411 prevents leakage of the external liquid toward the pad hole 161 from contaminating the wound on the skin surface. It should be noted that, it is possible to omit one of the waterproof portion 162 of the adhesive pad 16 and the connecting portion 411 of the sealing unit without reducing the effectiveness of leakage prevention. In other embodiments, the first and third sealing members 41, 43 may be separate pieces (as shown in FIG. 17), and the connecting portion 411 may extend downwardly from the third sealing member 43 only or may be omitted. In other embodiments, the connecting portion 411 extends downwardly from the third sealing member 43 along a surrounding surface of the through hole 118 of the base body 11 to surround the pad hole 161 of the adhesive pad 16, and abuts against the adhesive pad 16 for blocking the contaminated liquid absorbed in the adhesive pad 16 from moving toward the pad hole 161 and contacting the wound under the pad hole 161. As such, the waterproof portion 162 of the adhesive pad 16 may be omitted.

Lastly, referring back to FIGS. 8 and 9, the extended section 223 of the sensing member 22 extends through and tightly abuts against the blocking member 45, and the sensing section 222 of the sensing member 22 extends through and tightly abuts against the third sealing member 43, so that the sensing member 22 is stably positioned relative to the mounting seat 21. While the blocking member 45 permits the extended section 223 of the sensing member 22 to extend therethrough, the blocking member 45 fluid-tightly separates the fitting hole 214 and the mounting space 210 of the mounting seat 21, so that the body fluid does not flow from the fitting hole 214 toward the inner space 30 of the transmitter 3 through the mounting space 210 (also noted as the fluid pathway (b) in FIG. 15).

In this embodiment, the first sealing member 41 and the third sealing member 43 are formed as a single piece coupled to the base body 11. The second and fourth sealing members 42, 44 and the blocking member 45 are formed as a single piece coupled to the mounting seat 21. However, the abovementioned sealing members may be separate pieces in other embodiments.

Referring to FIG. 17, in a modification of the first embodiment, the first and third sealing members 41, 43 are separate pieces and are not connected to one another directly, and the first and second sealing members 41, 42 are O-rings, preferably the type of O-rings with triangular cross-section. However, the disclosure is not restricted as such.

Figure 18:
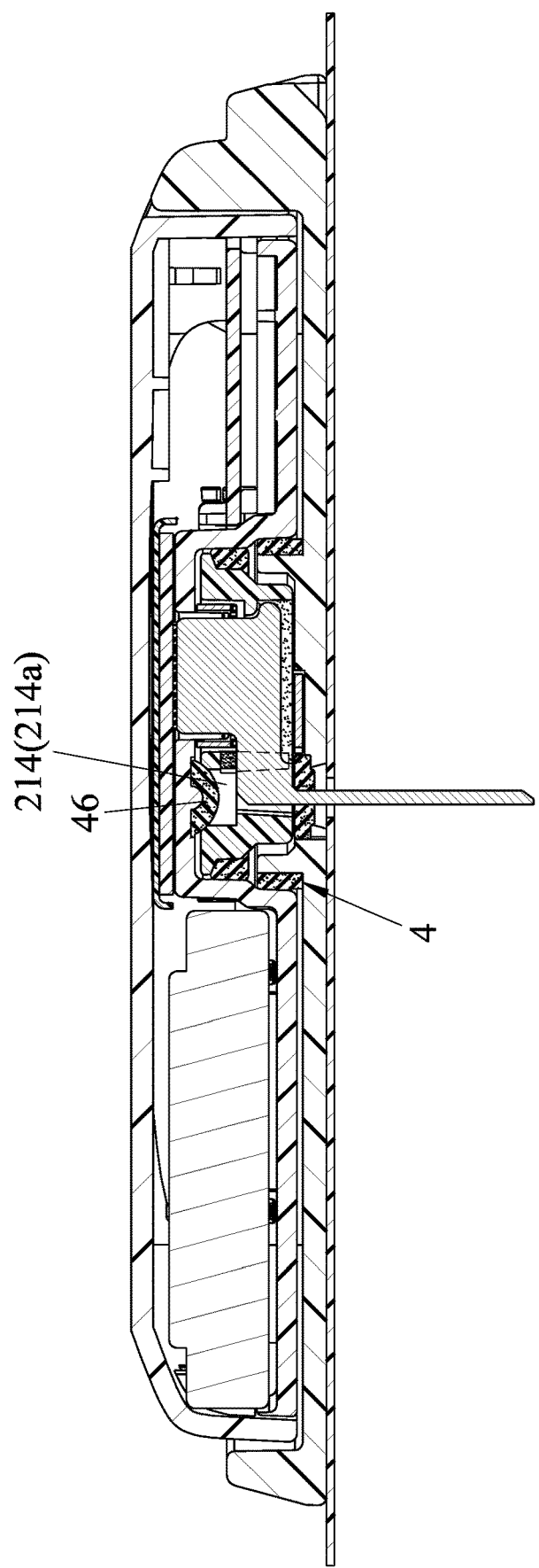

Referring to FIG. 18, in another modification of the first embodiment, the fourth sealing member 44 of the sealing unit 4 is omitted, and the urging member 46 is tightly coupled to the top portion 214a of the fitting hole 214 directly to seal the fitting hole 214. In addition, as the urging member 46 is made of a rubber material, it is easily deformable to fittingly engage the top portion 214a of the fitting hole 214, thereby securely sealing the implantation path 600.

Figure 19:
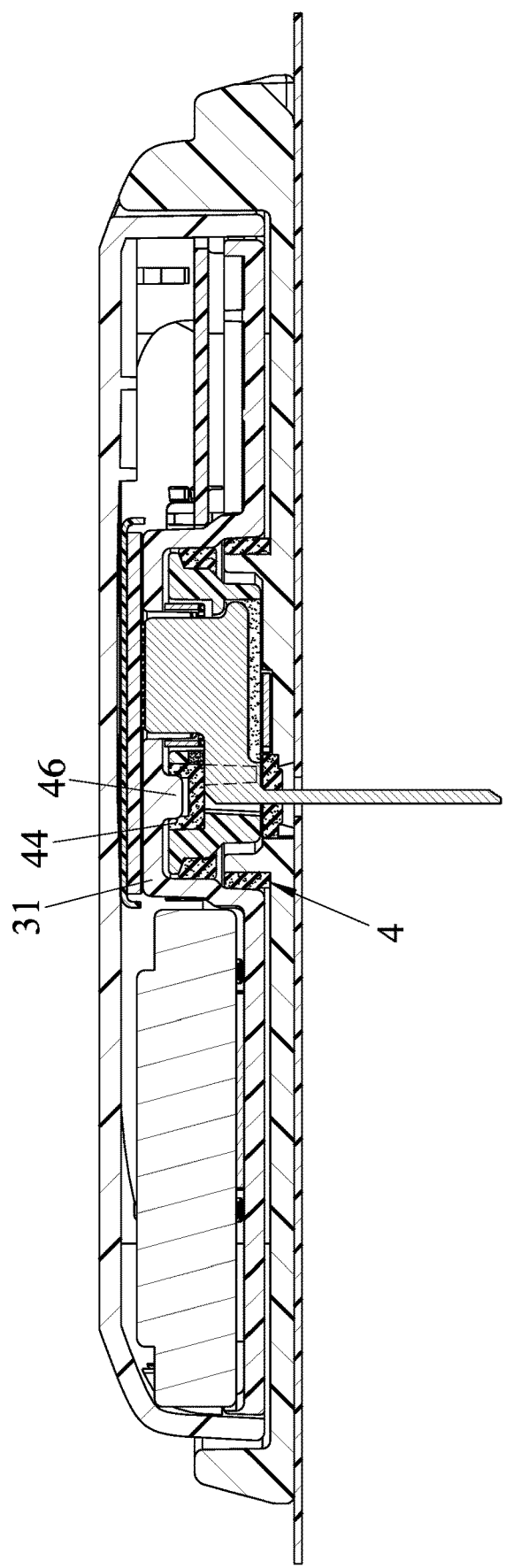

Referring to FIG. 19, in yet another modification of the first embodiment, the urging member 46 of the sealing unit 4 and the bottom casing 31 of the transmitter 3 are formed as a single piece of non-elastic material, and the urging member 46 is tightly coupled to the groove formed on top of the fourth sealing member 44.

Figure 20:
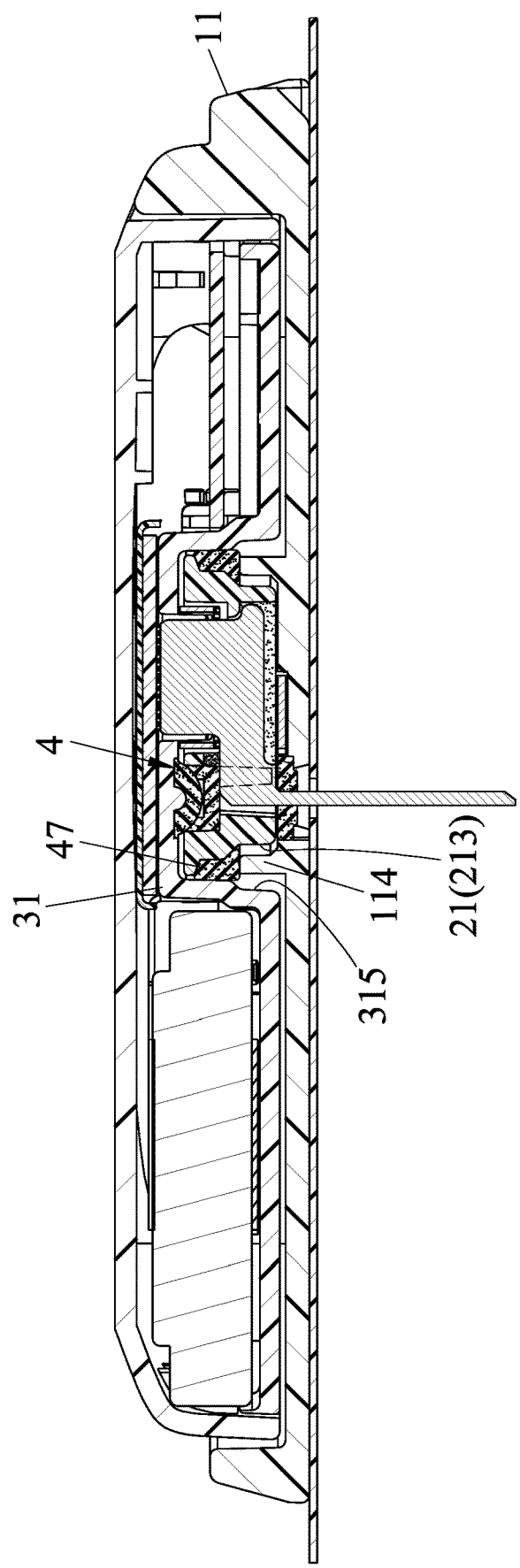

Referring to FIG. 20, in yet another modification of the first embodiment, the first and second sealing member 41, 42 are replaced with a main sealing member 47 that is clamped among the outer surrounding surface 213 of the mounting seat 21, a top edge of the inner groove wall 114 of the base body 11, and the groove surrounding surface 315 of the transmitter 3 for sealing the fluid pathways (c, d, e).

Figure 21:
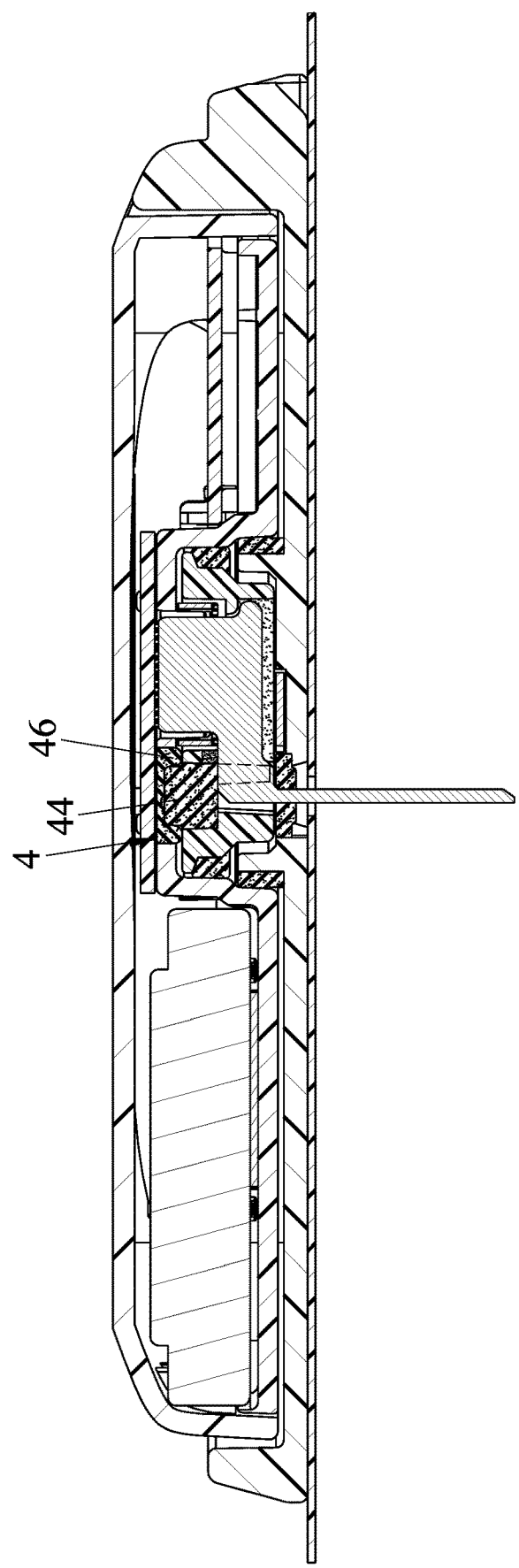

Referring to FIG. 21, in yet another modification of the first embodiment, the groove on the fourth sealing member 44 is omitted, and the urging member 46 is indented with a groove on a bottom surface thereof for the fourth sealing member 44 to be tightly coupled thereto instead. As both the fourth sealing member 44 and the urging member 46 are made of rubber materials, they are easily deformable to be tightly coupled with each other, thereby sealing the implantation path 600.

Figure 22:
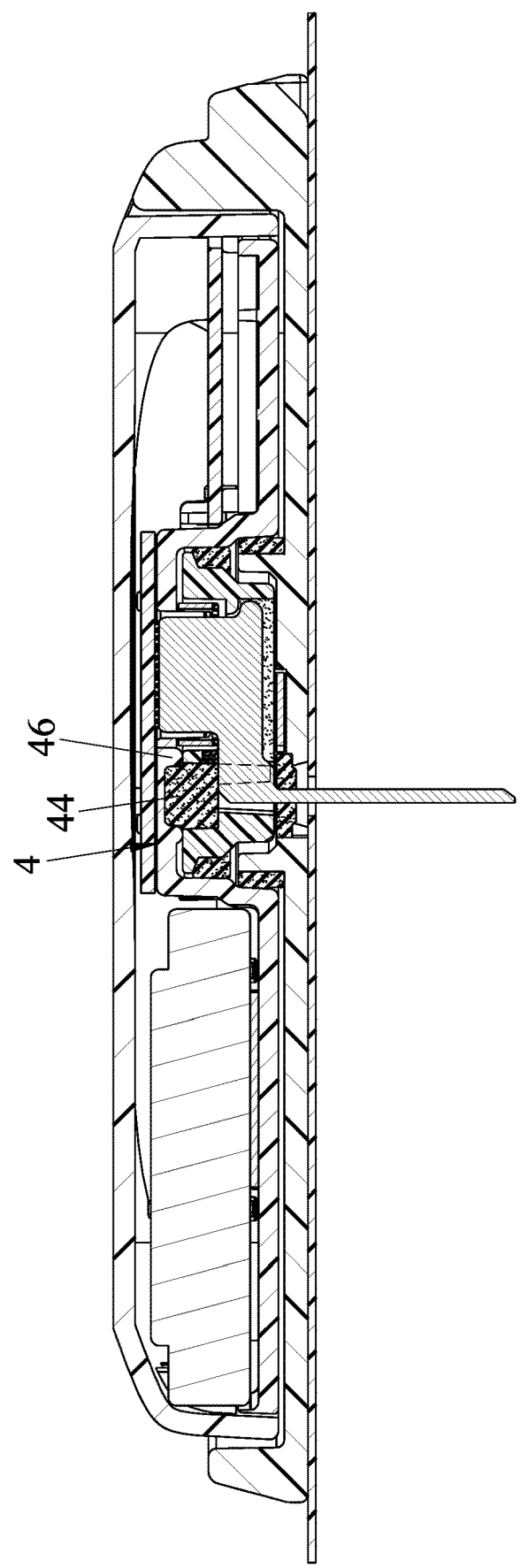

Referring to FIG. 22, in yet another modification of the first embodiment, the groove on the fourth sealing member 44 is omitted, and the urging member 46 is indented with a groove on a bottom surface thereof for the fourth sealing member 44 to be tightly coupled thereto instead. However, the urging member 46 of the sealing unit 4 and the bottom casing 31 of the transmitter 3 are formed as a single piece of hard material, while the fourth sealing member 44 is made of a rubber material. As such, the fourth sealing member 44 is easily deformable to be tightly coupled to the groove formed beneath the urging member 46, thereby sealing the implantation path 600.

Referring back to FIGS. 2 and 4, the physiological signal monitoring device of the present disclosure is meant to measure a tiny current on the scales of nanoampere (nA). In addition to maintaining the fluid-tightness, the physiological signal monitoring device further includes a desiccant 5 that is mounted anywhere in an airtight space 100 (see FIG. 4) cooperatively defined by the base 1 and the transmitter 3 when the base 1 and the transmitter 3 are coupled to each other, so that the biosensor 2 is remained to be in low humidity to ensure proper measurement. In this embodiment, the airtight space 100 is formed between the first groove 313 of the bottom casing 31 of the transmitter 3 and the bottom plate 111 of the base 1, the top surface 212 of the mounting seat 21 is formed with two humidity grooves 217 (see FIG. 2) for storing two of the desiccants 5 therein, and a junction between the sensing member 22 and the transmitter 3 is in the airtight space 100.

However, in a modification of the embodiment, the humidity grooves 217 are omitted, and the groove bottom surface 316 of the transmitter 3 is formed with two humidity grooves (not shown) for storing the desiccants 5 therein. In other embodiments, the mounting seat 21 itself may be partially made of the desiccants 5 during the injection molding process, such that the biosensor 2 as a whole remained to be in low humidity.

To provide a thorough understanding of the disclosure, coupling and disassembling operations of the physiological signal monitoring device are described as follows.

Referring back to FIG. 2, the base 1, the biosensor 2, and the transmitter 3 are separated from one another before use, and are coupled to one another to be mounted to the skin surface of the host. Referring back to FIG. 12, during the assembling, the base 1 and the biosensor 2 are coupled to the insertion device (not shown), the sensing section 222 of the sensing member 22 is carried by the insertion tool 9 of the insertion device to puncture the fourth sealing member 44 and extend through the fitting hole 214 of the mounting seat 21 in the inserting direction (D4), and the base body 11 is attached to the skin surface via the adhesive pad 16. Then, as the sensing section 222 of the sensing member 22 is carried by the insertion tool 9 to puncture the third sealing member 43 and extend through the through hole 118 of base body 11 and subsequently through the skin surface of the host, the mounting seat 21 of the biosensor 2 is mounted to the mounting groove 113 of the base body 11 and is coupled to the hooking member 14. Referring back to FIG. 13, after the sensing section 222 of the sensing member 22 is inserted underneath the skin surface of the host, the insertion tool 9 is drawn out from the host so that the insertion device is separated from the base 1 and the biosensor 2, while the base 1 and the biosensor 2 remain coupled to one another. The third and fourth sealing member 43, 44 of the sealing unit 4 (see FIG. 2) are made of elastic materials, such as rubbers, so that the slits of the third and fourth sealing member 43, 44 will automatically close to seal the implantation path 600 as the insertion tool 9 is drawn out from the host and is separated from the base 1 and the biosensor 2. Lastly, referring back to FIGS. 3 and 5, to finish the assembling process, the transmitter 3 covers the base body 11 so that the first and second coupling structures 12, 37 are driven by the external force to be coupled to each other, while the signal output section 221 of the sensing member 22 is inserted into the connection port 36 via the socket 367 in the direction of the first axis (D1). The physiological signal monitoring device is now permitted to measure analytical substance(s) of the host via the sensing member 22, and to send the physiological signal to a receiving device (not shown) via the transmitter 3.

Moreover, based on the aforesaid description, since the first coupling portion 121 and the second coupling portion 371 are respectively extended from the top surface 115 of the bottom plate 111 and the bottom casing 31 of the transmitter 3, the internal components of the physiological signal monitoring device are unlikely to be damaged during engagement of the first and second coupling portions 121, 371. Moreover, the arrangement of the first coupling portion 121 and the second coupling portion 371 makes the assembly of the base 1 and the transmitter 3 easy.

Designed with the environment in mind, the physiological signal monitoring device of the present disclosure is provided with reusable components. For example, the transmitter 3 of the present embodiment is reusable. When the service life of the biosensor 2 is reached, the user may separate the used biosensor 2 from the transmitter 3 and the base 1, and mount a new biosensor 2, along with the same transmitter 3 and the base 1, to the skin surface of the host using the aforesaid method. It should be noted that, once mounted to the skin surface of the host, the present embodiment can be used for approximately two weeks. However, the duration of use of the physiological signal monitoring device of this disclosure is not limited thereto and may vary depending on practical conditions, materials of the components, and types of the components.

Referring back to FIGS. 4 and 14, to uncouple the biosensor 2 from the base 1, the base 1 is detached from the skin surface initially. Then, the user may exert the external force manually, or via a disassembly member 7, through the openings 117 of the base body 11 onto one of the first coupling structures 12, the second coupling structures 37, and a location where the first and second coupling structures 12, 37 are coupled to each other to uncouple the two, so that the transmitter 3 is easily separated from the base 1 and the biosensor 2. While the base 1 and the biosensor 2 have relatively shorter service life due to safety reasons, the transmitter 3, which is not in direct contact with the host, can be repeatedly used over longer period of time with new sets of the base 1 and the biosensor 2.

It should be noted that, since the first and second coupling structures 12, 37 are disposed to be distal from a periphery cooperatively defined by the base 1 and the transmitter 3 when the first and second coupling structures 12, 37 are coupled to each other, the periphery of the whole device does not need to have any disassembly member meant for disassembling the transmitter 3 from the base 1, and thus looks more complete. Furthermore, in conjunction with the sealing unit 4, the first and second coupling structures 12, are simpler in shape, thereby permitting the physiological signal monitoring device to have a simpler and more compact, portable design.

More specifically, referring back to FIGS. 2, 5 and 9, many components of the base body 11, the biosensor 2, and the transmitter 3 fittingly engage with one another in the direction of the first axis (D1) to minimize the overall volume of the physiological signal monitoring device: the connection port 36 is retained in the mounting space 210 of the mounting seat 21 when the signal output section 221 of the sensing member 22 is inserted into the connection port 36; the mounting seat 21 is mounted in the inner groove wall 114 (i.e., in the mounting groove 113), both of which are mounted in the first groove 313 of the transmitter 3; the first and second coupling structures 12, 37 are disposed in the second grooves 314 to be coupled with each other. The overall thickness of the physiological signal monitoring device is permitted to be reduced to be smaller than 5 millimeters (mm), such that it does not stick out in the public eye as much, and becomes more difficult to be tampered with by accident. In this embodiment, the overall thickness of the physiological signal monitoring device is 4.9 mm, the overall width, length and thickness of the base body 11 are respectively 23.0 mm, 36.0 mm, and 3.5 mm, the overall width, length and thickness of the transmitter 3 are respectively 19.9 mm, 32.9 mm, and 4.15 mm, and the volume of the physiological signal monitoring device is 3358 cubic millimeters, but is not restricted as such.

In addition, in this embodiment, the bottom casing 31 of the transmitter 3 has a hardness higher than that of the base body 11 and the first coupling structures 12 of the base 1, so that the bottom casing 31 is not damaged during the disassembly process, thereby ensuring the durability of the transmitter 3. For example, the bottom casing 31 may be made of mixture of polycarbonate and fiberglass, the base body 11 and the first coupling structures 12 may be made of polycarbonate, but is not restricted to such.

Referring to FIGS. 23 to 28, a second embodiment of the physiological signal monitoring device is similar to that of the first embodiment, with differences as follows.

Figure 23:
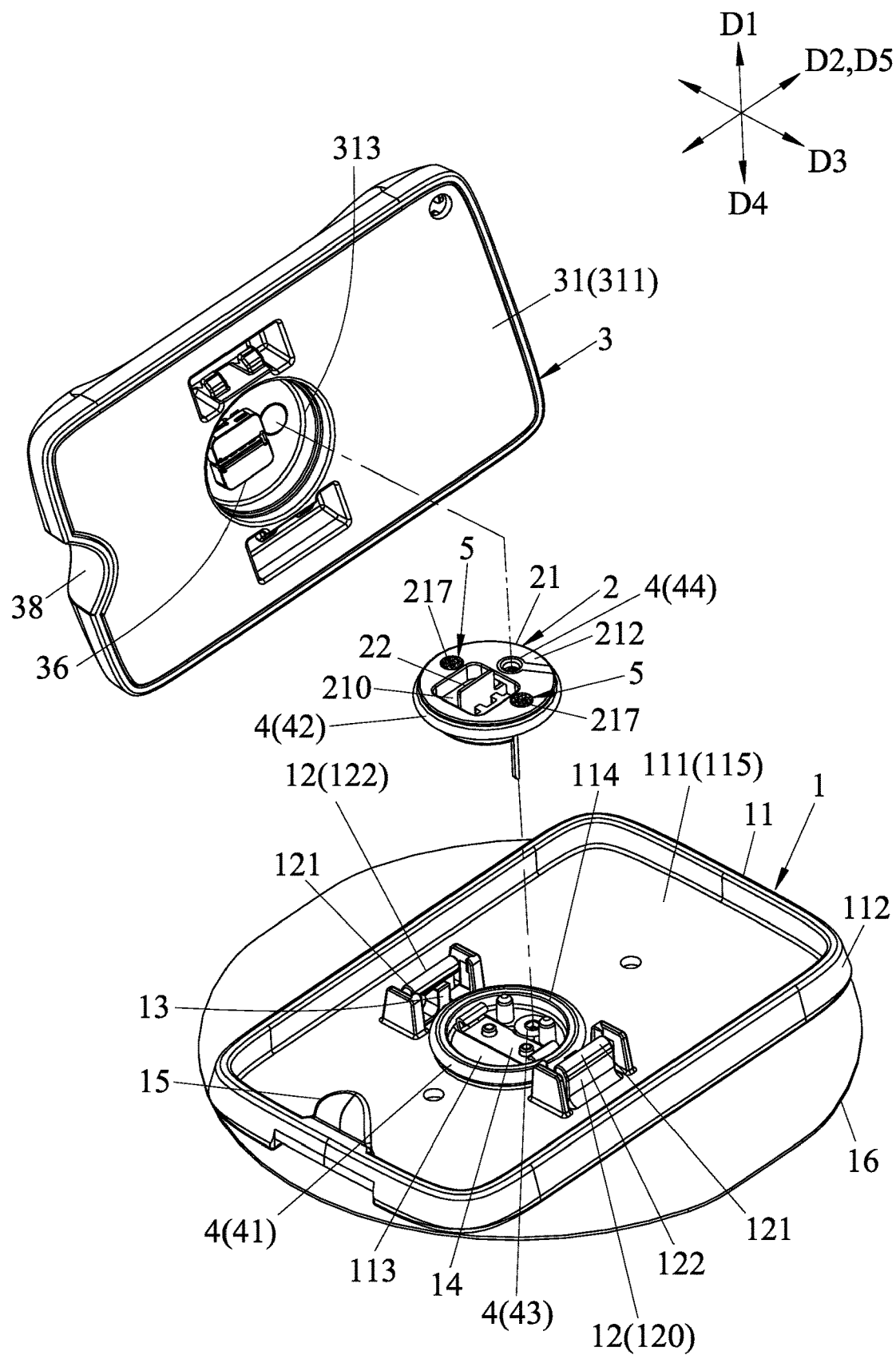
FIG. 23 is an exploded perspective view of a second embodiment of the physiological signal monitoring device.
Figure 24:
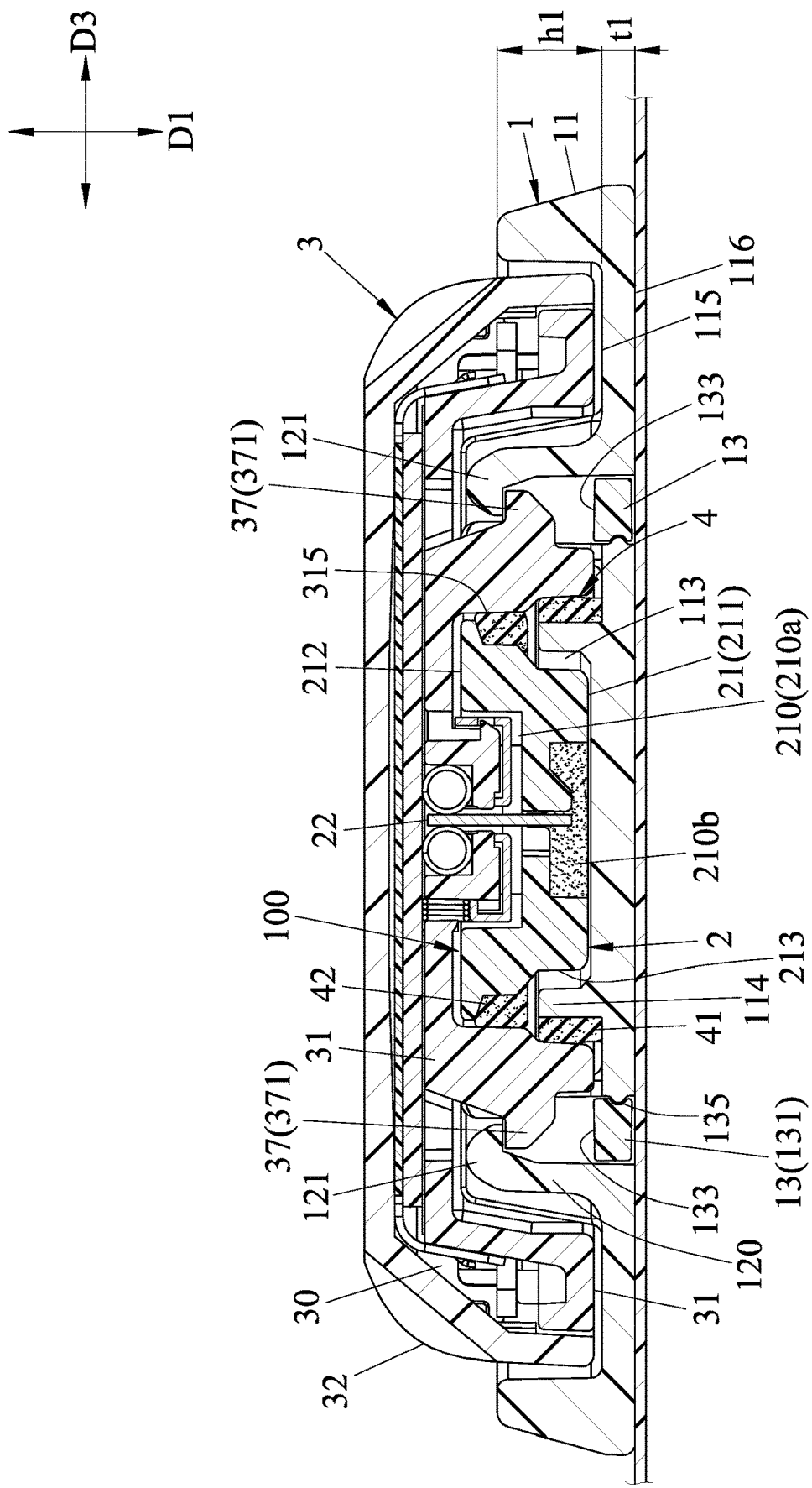
FIG. 24 is a sectional view of the second embodiment that is similar to FIG. 4.
Figure 25:
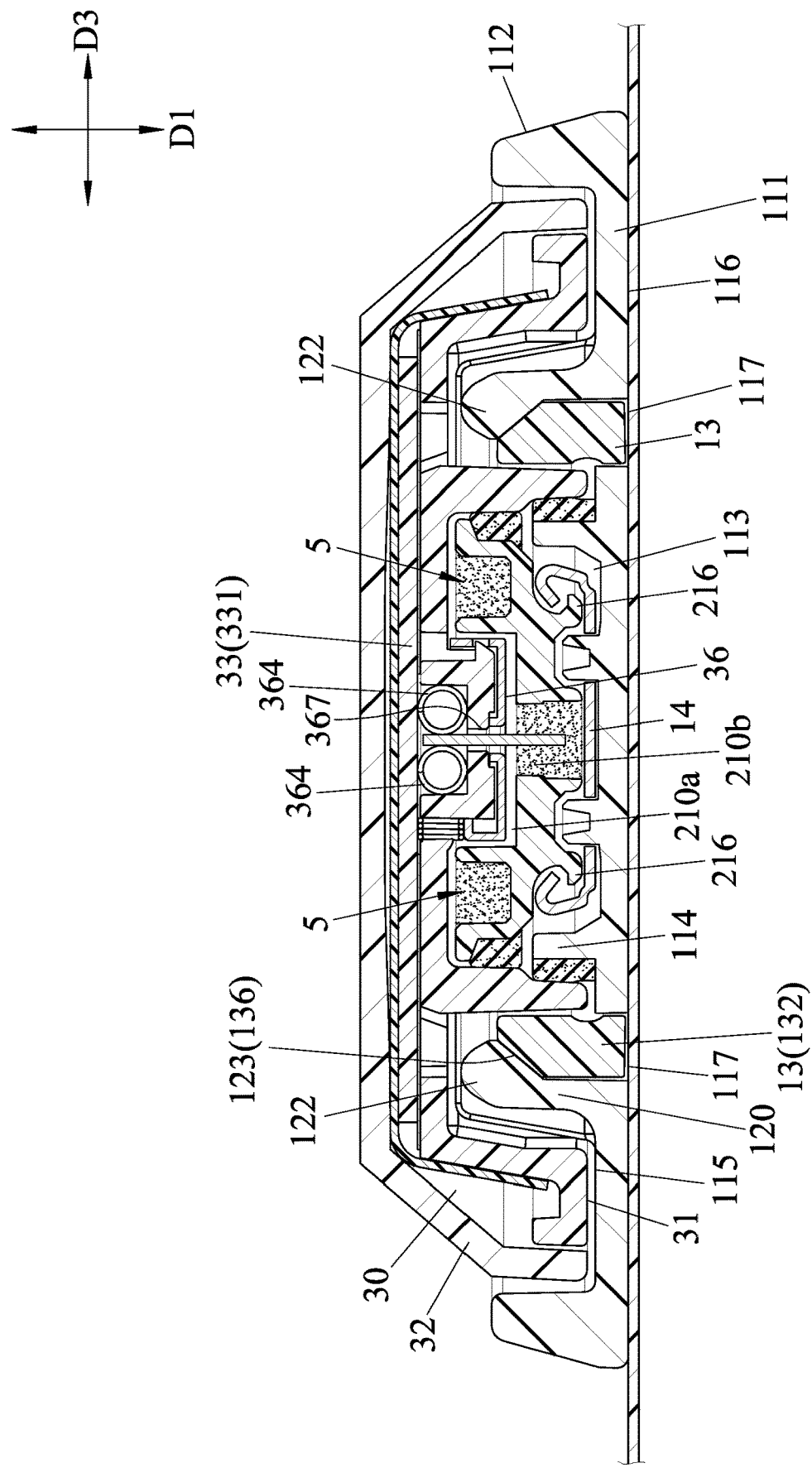
FIG. 25 is a sectional view of the second embodiment that is similar to FIG. 5.

Referring specifically to FIGS. 23 to 25, the first coupling portion 121 of each of the first coupling structures 12 has a toggling section 122 that is not coupled to a corresponding one of the second coupling structures 37 when the transmitter 3 is mounted to the base body 11, and that has a slanted surface 123. The slanted surface 123 extends upwardly and gradually in a direction toward the center of the opening 117 and creates a space within the location where a corresponding pair of the first and second coupling structures 12, 37 are coupled to each other.

Figure 26:
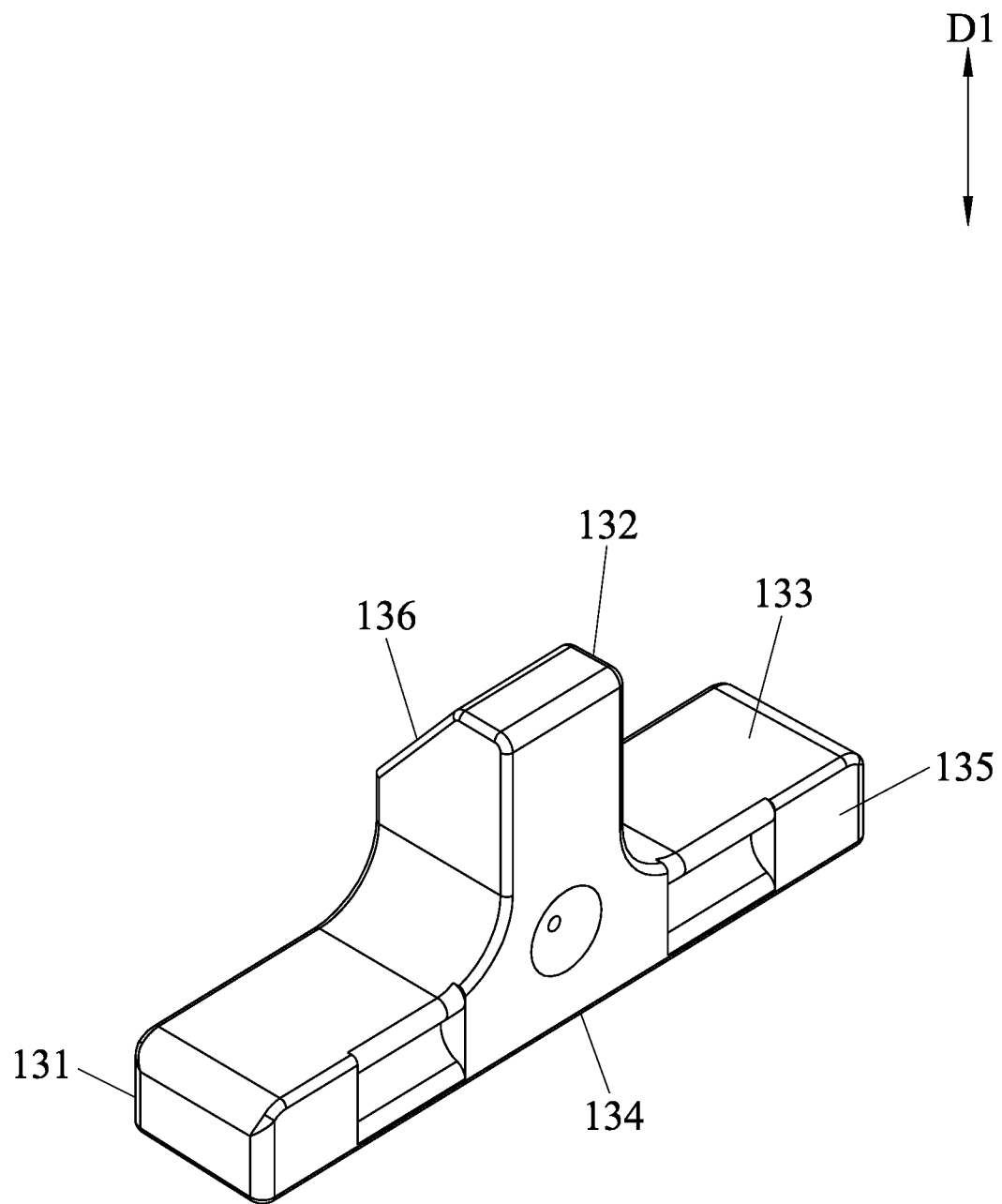
FIG. 26 is a perspective view of an ejection member of the second embodiment.

Referring back to FIG. 23, the base 1 further includes at least one ejection member 13 that is preassembled to the base body 11. Referring to FIGS. 24 to 26, in this embodiment, the base 1 includes two ejection members 13 that are respectively disposed at and extend through the openings 117, and that protrude from the top surface 115 of the base body 11. Each of the ejection members 13 is mounted between the slanted surface 123 of the toggling section 122 of a respective one of the first coupling structures 12 and a respective one of the openings 117, and is permitted to be pushed by the external force to move toward the slanted surface 123 of the toggling section 122.

Each of the ejection members 13 has a positioning portion 131 that is removably coupled to the bottom plate 111 of the base body 11, and a protruded portion 132 that extends upwardly from the positioning portion 131. The positioning portion 131 has a top surface 133 that is connected to the protruded portion 132, a bottom surface 134 that is opposite to the top surface 133 and that is substantially flush with the bottom surface 116 of the bottom plate 111, and a side surface 135 that interconnects the top and bottom surfaces 133, 134. The side surface 135 fittingly engages with a surface of the bottom plate 111 (shown in FIG. 23) via a groove-protrusion configuration (see FIG. 24), so that the ejection member 13 is positioned to the base body 11, but is not restricted to such. The top surface 133 corresponds in position to the second coupling portions 371 of a respective one of the second coupling structures 37 in the direction of the first axis (D1). The protruded portion 132 has an against surface 136 that is proximate to the slanted surface 123 of the respective one of the first coupling structures 12, and that is slanted in an angle to complement the slanted surface 123.

Figure 27:
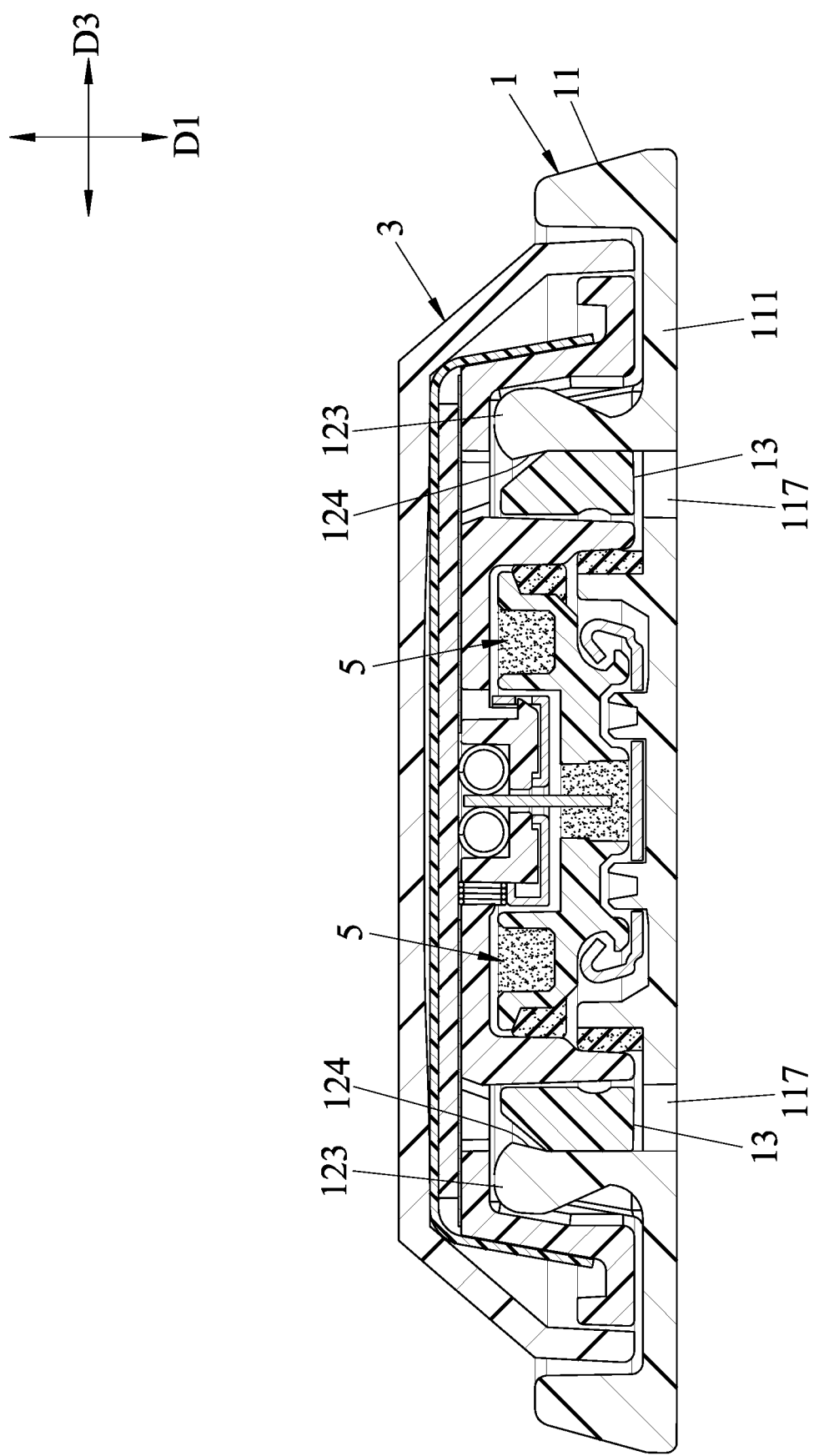
FIG. 27 is a view similar to FIG. 25, illustrating a plurality of ejection members being pushed upwardly.
Figure 28:
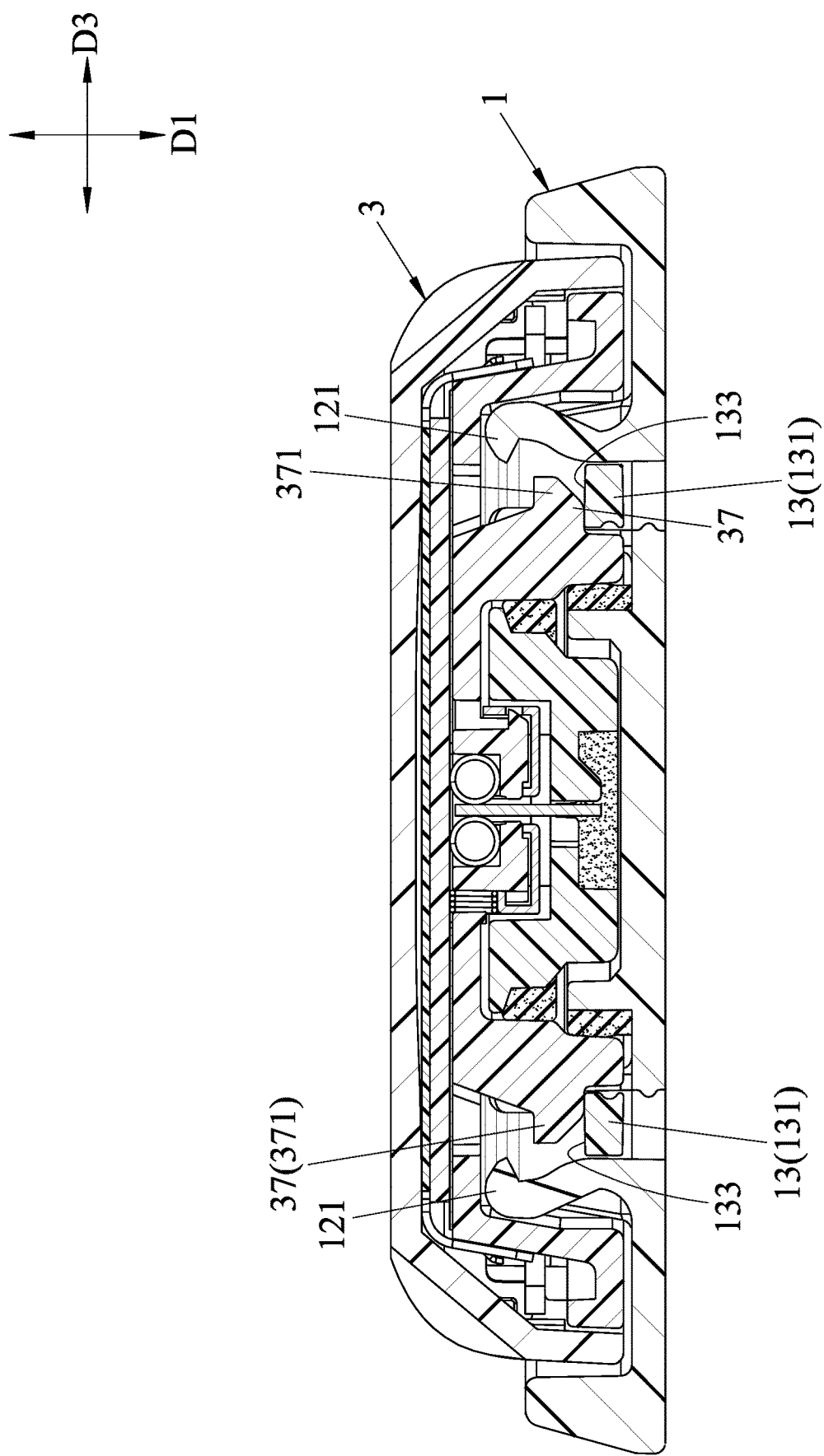
FIG. 28 is a view similar to FIG. 24, illustrating a plurality of ejection members being pushed upwardly.

To disassemble the biosensor 2 from the base 1, the ejection members 13 are pushed upwardly relative to the base body 11 in the direction of the first axis (D1) to move toward the location where the first and second coupling structures 12, 37 are coupled to each other, such that the against surfaces 136 of the ejection members 13 respectively push the slanted surfaces 123 of the first coupling structures 12 (see FIGS. 25 and 27). Pushed by the ejection members 13, for each of the first coupling structures 12, the toggling section 122 drives the first coupling portion 121 to rotate with respect to the base portion 120 in a direction away from corresponding ones of the second coupling portions 371 to thereby separate the first and second coupling portions 121, 371 (see FIGS. 24 and 28). At the same time, the top surfaces 133 of the positioning portions 131 of the ejection members 13 push bottom ends of the second coupling structures 37 (see FIG. 28) to push the transmitter 3 away from the base 1, so that the transmitter 3 is permitted to be separated from the existing pair of the base 1 and the biosensor 2 to be reused with the new sets of the base 1 and the biosensor 2.

In the second embodiment, by mounting the ejection members 13 respectively to the openings 117 of the base body 11, the user may reliably apply the external force to push the first coupling structures 12 through the openings 117 in the direction of the first axis (D1), thereby not requiring an external tool like the disassembly member 7 of the first embodiment. Also, since the top surfaces 133 of the positioning portions 131 of the ejection members 13 correspond in position to the second coupling portions 371 of the second coupling structures 37, the ejection members 13 also facilitate separation of the transmitter 3 from the base 1. In addition, since the bottom surfaces 134 of the ejection members 13 are substantially flush with the bottom surface 116 of the base body 11, the skin surface of the host would not be left with an indentation mark due to prolonged exposure to the opening 117 of the base body 11. In other embodiments, the toggling section 122 of the first coupling structure 12 and the protruded portion 132 of the ejection member 13 may be omitted, and the ejection member 13 is still permitted to be pushed by the external force to uncouple the first and second coupling structures 12, 37 by moving toward the location where the first and second coupling structures 12, 37 are coupled to each other.

Figure 29:
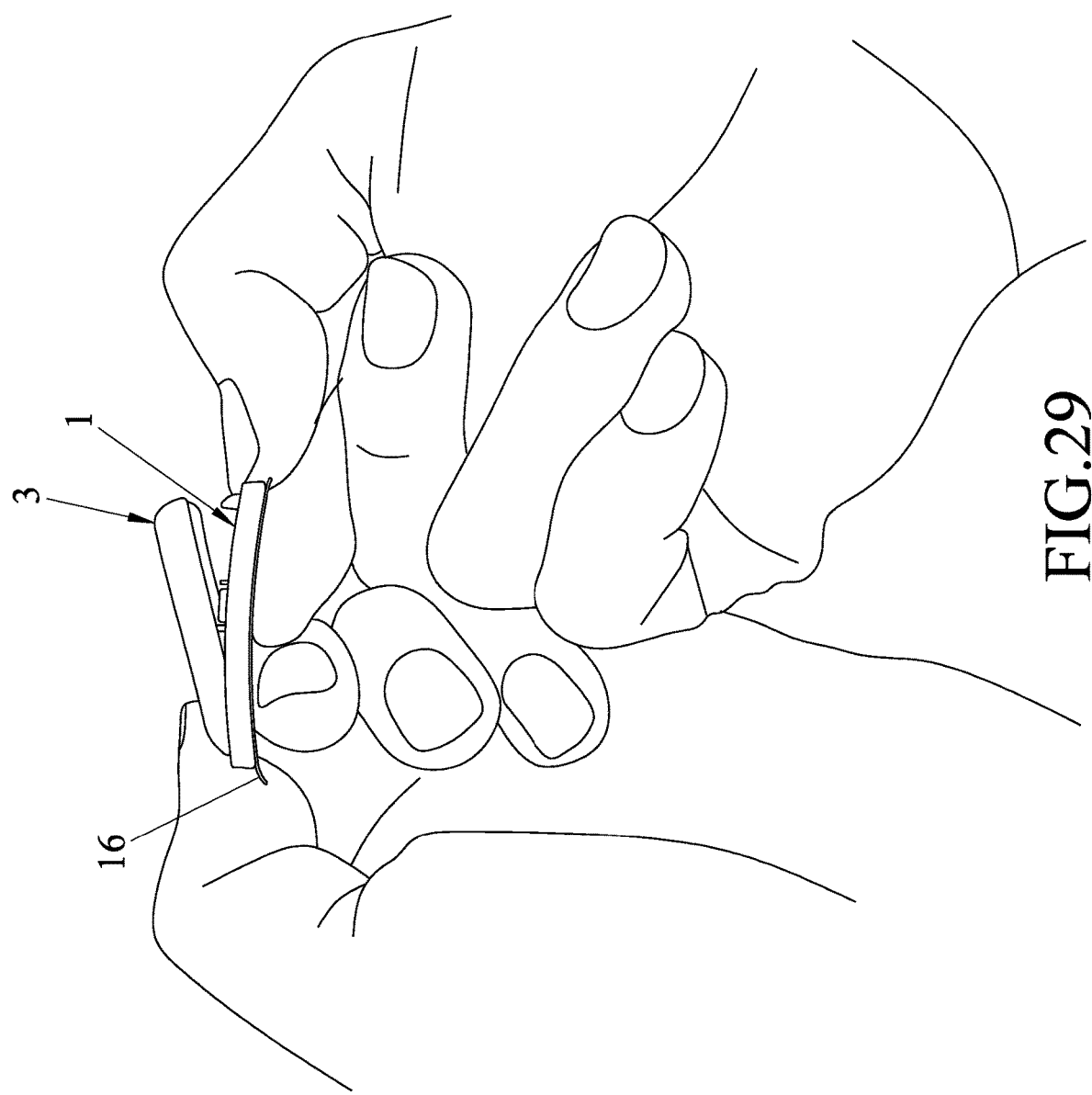
FIGS. 29 and 30 are perspective views of a third embodiment of the physiological signal monitoring device, illustrating the base and the transmitter being disengaged from each other.
Figure 30:
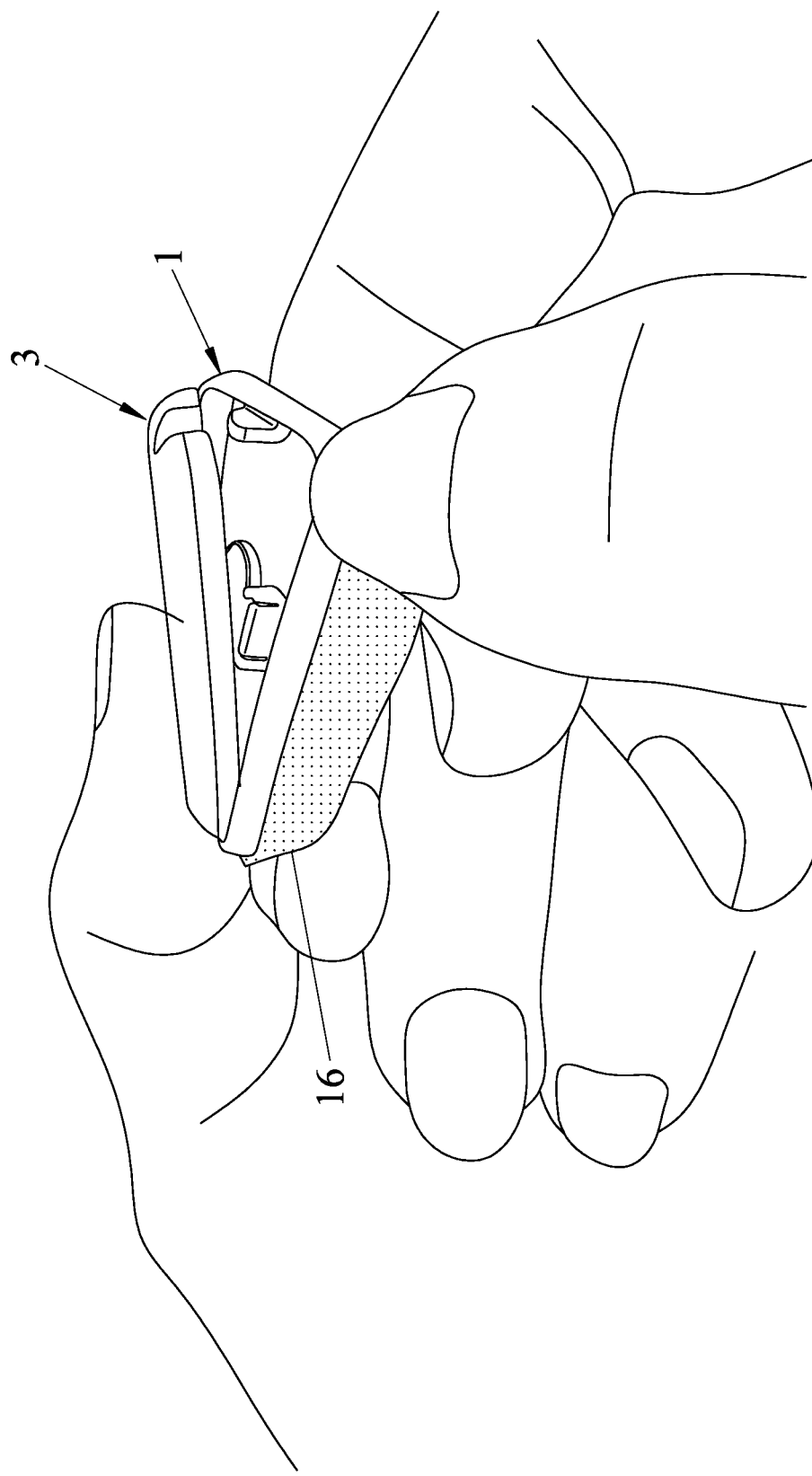
Figure 31:
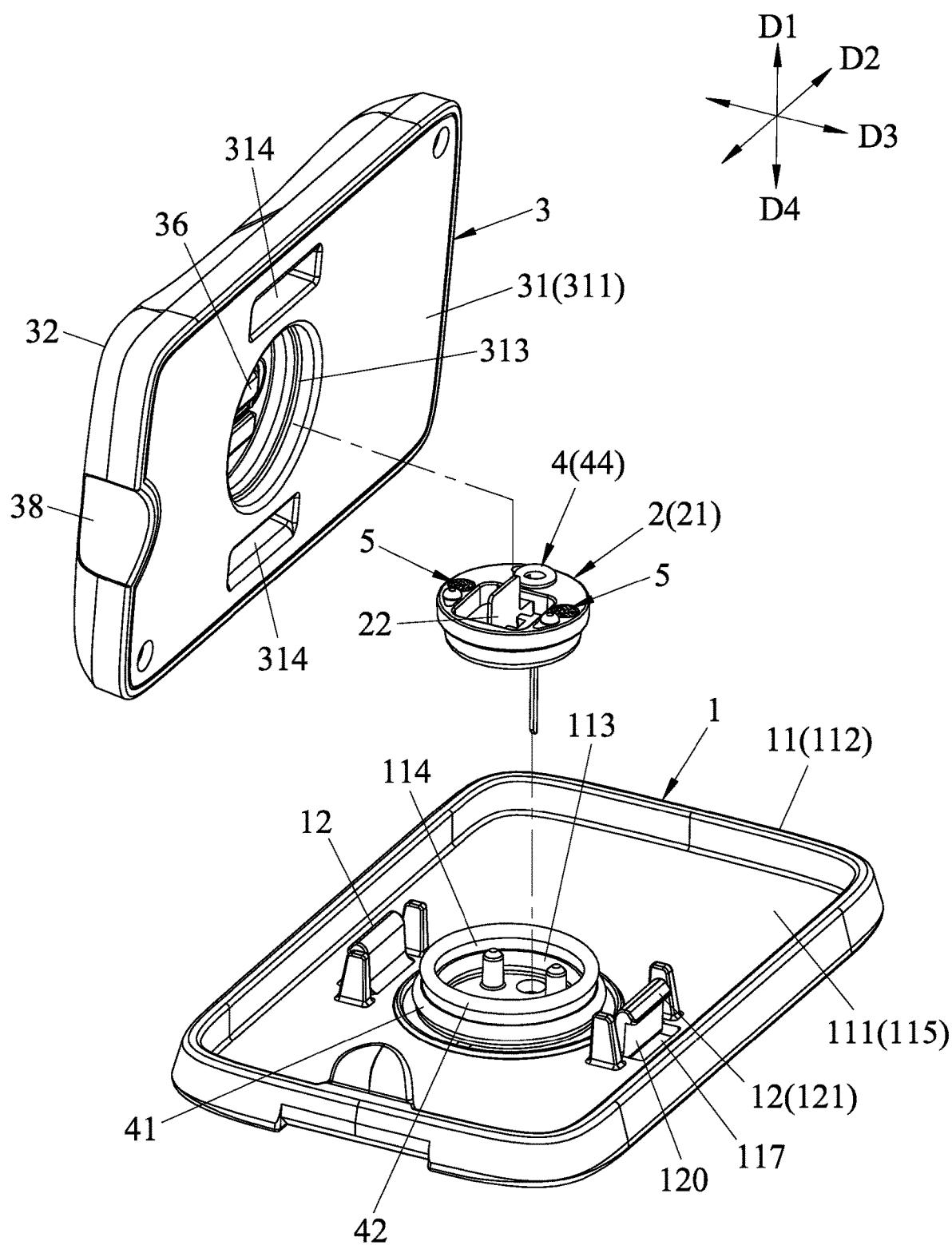
FIG. 31 is an exploded perspective view of a fourth embodiment of the physiological signal monitoring device.
Figure 32:
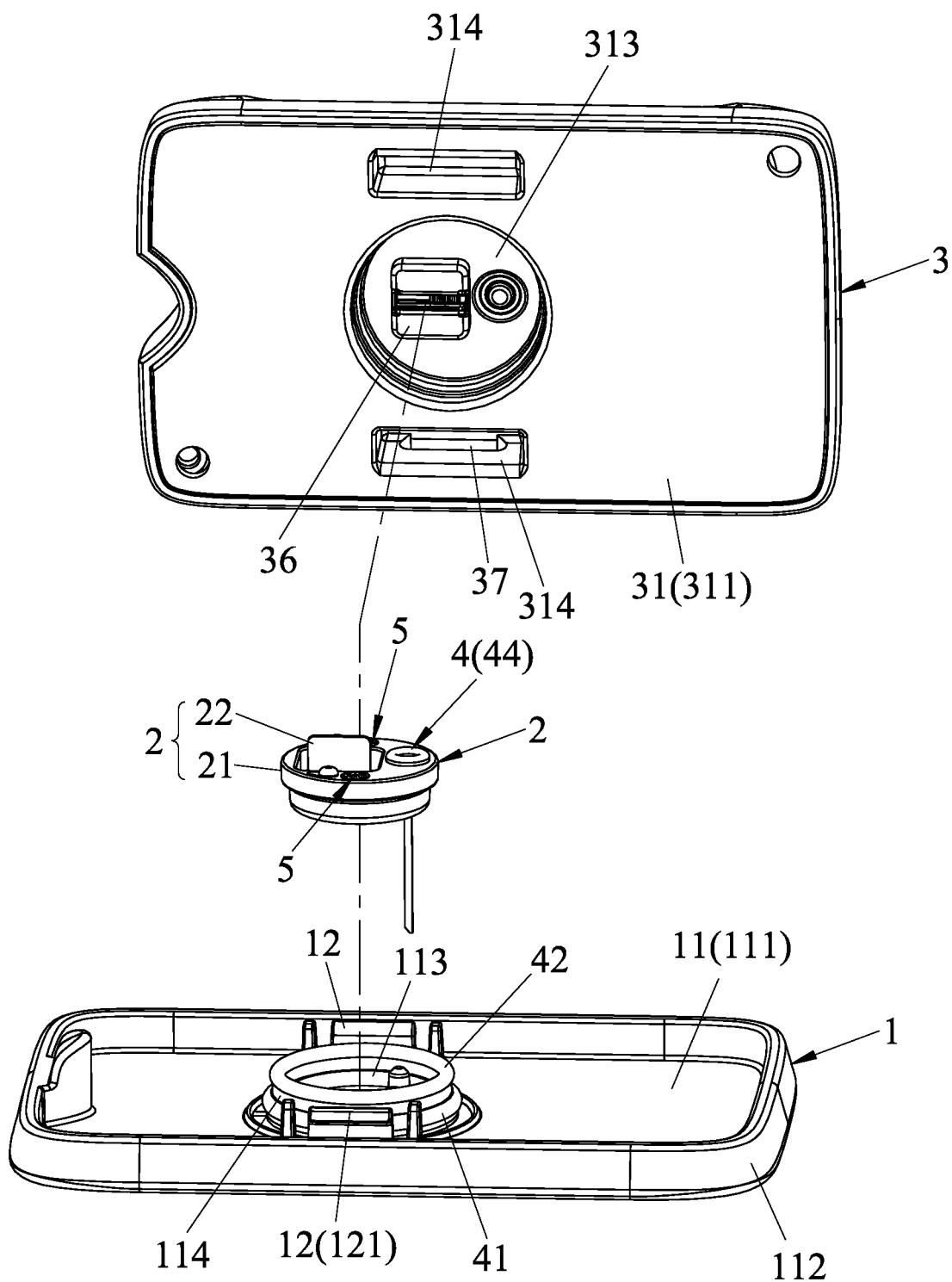
FIG. 32 is another exploded perspective view of the fourth embodiment.

Referring to FIGS. 29 and 30, a third embodiment of the physiological signal monitoring device is similar to that of the first embodiment, with differences as follows.

The base body 11 of the base 1 is flexible, such that, by applying an external force to bend the base body 11 on a periphery of the base body 11, e.g., a side thereof (see FIG. 29) or on a corner thereof (see FIG. 30), the first and second coupling structures 12, 37 are permitted to be uncoupled and the transmitter 3 is then permitted to be separated from the base 1 by the flexibility of said base body (11).

Specifically, in this disclosure, the "flexible" property of the base body 11 means that the base body is flexible in a way to be even more fittingly attached to the skin surface, which improves comfortability for the host, while provides stable support for the biosensor 2 and the transmitter 3. Furthermore, rather than separating the transmitter 3 from the base body 11 by applying an external force through the opening 117, the external force may be applied to the side of the base body 11 instead to deform the base body 11 and then separate the first and second coupling structures 12, 37 in this embodiment. That is, the transmitter 3 can be detached from the base 1 without having to detach the physiological signal monitoring device from the skin surface of the host first. As such, the opening 117 of the base 1 may be omitted in a modification of the third embodiment. In other embodiments, however, both the flexible base body 11 and the openings 117 may be present.

Referring back to FIG. 4, the flexibility of the abovementioned base body 11 may be contributed by the material chosen, by reducing a thickness (t1) of the bottom plate 111 of the base body 11, and/or by reducing a height (h1) of the surrounding wall 112 of the base body 11. Specifically, in terms of materials, the base body 11 is made of one of polymer material (such as plastics, rubbers or silica gels), metallic material and a mixture of polymer material and metallic material. In terms of dimensions, the thickness (t1) of the bottom plate 111 of the base body 11 depends primarily on the material used and typically ranges from 0.05 to 1 mm, and the height (h1) of at least a portion of the surrounding wall 112 measured from the top surface 115 of the bottom plate 111 is no more than 3 mm to thereby ensure the flexibility of the base body 11. For example, the thickness (t1) is able to be 0.05 mm at minimum if the base body 11 is injection molded with a metallic material, and the thickness (t1) is able to be 0.3 mm at minimum if the base body 11 is injection molded with a plastic material. In this embodiment, the base body 11 is made of polycarbonate material with the bottom plate 111 having the thickness (t1) of 0.6 mm and the surrounding wall 112 having the height (h1) of 2.4 mm.

Referring to FIGS. 31 to 34, a fourth embodiment of the physiological signal monitoring device is similar to that of the first embodiment, with differences as follows.

Instead of extending away from the periphery of the base body 11, the first coupling portions 121 of the first coupling structures 12 of the base 1 in the fourth embodiment extend toward the periphery of the base body 11. The openings 117 of the base body 11 are correspondingly adjusted to respectively correspond in position to the first coupling portions 121, so that the first coupling portions 121 still respectively extend toward the openings 117. The first coupling portions 121 also remain to be hook-shaped. In addition, referring specifically to FIG. 32, the second coupling structures 37 of the transmitter 3 are configured as grooves respectively formed in groove walls of the second grooves 314 of the bottom casing 31. When the transmitter 3 is covered to the base body 11 of the base 1, at least portions of the first coupling structures 12 are engaged with the second coupling structures 37.

In comparison to the first embodiment, the first coupling structures 12 of the fourth embodiment face toward the periphery of the base body 11 to provide extra space in the base body 11 for other components such as sealing members. In addition, as the base body 11 and the first coupling structures 12 are injection molded as a single piece, changing the coupling direction of the first coupling structures 12 also improves concentricity of internal components during the injection molding process. Furthermore, since the first coupling structures 12 are retained in position by a side wall of the bottom casing 31 of the transmitter when the first coupling structures 12 are respectively engaged with the second coupling structures 37, the coupling stability between the first and second coupling structures 37 are further improved.

Figure 35:
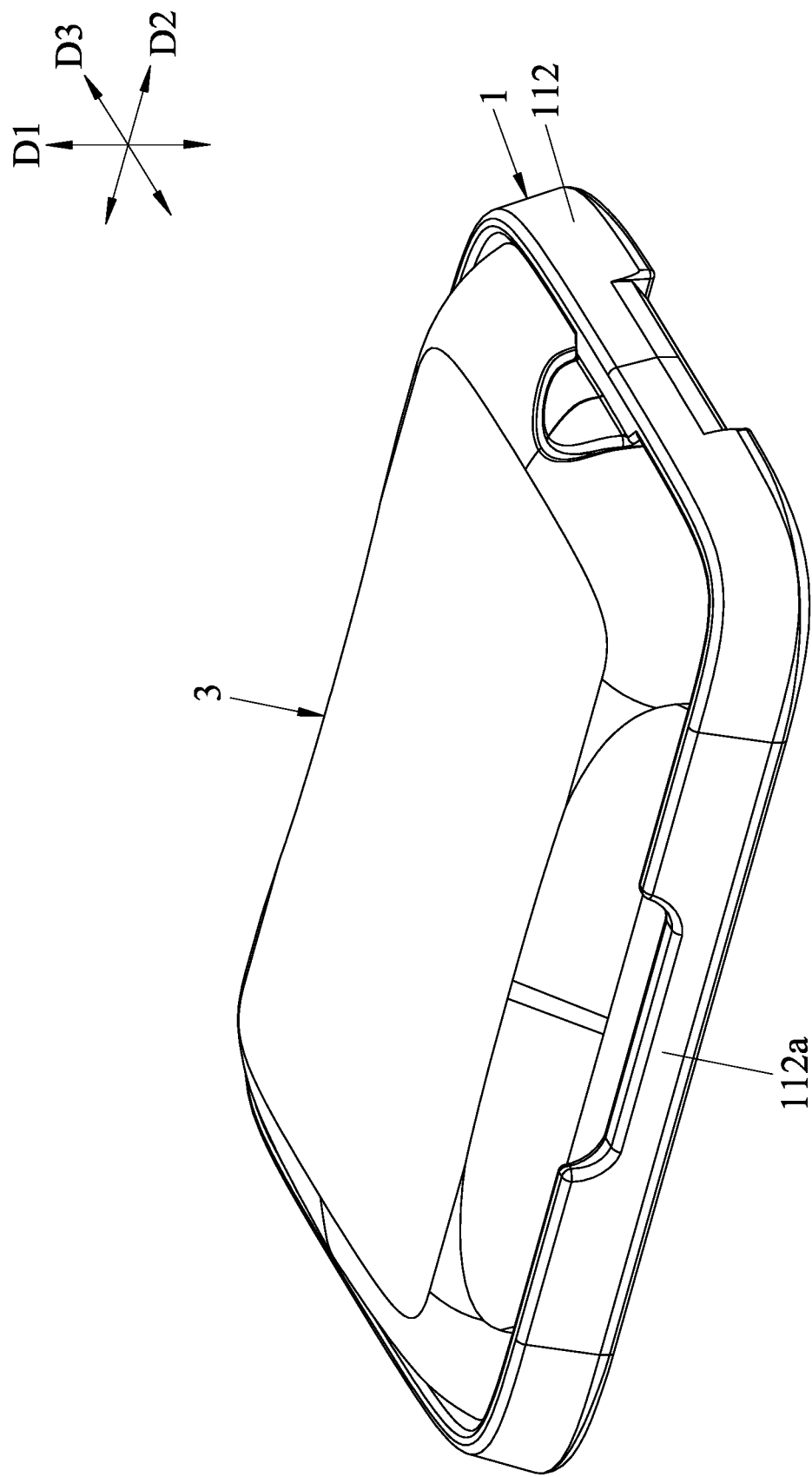
FIG. 35 is a perspective view of a fifth embodiment of the physiological signal monitoring device.
Figure 36:
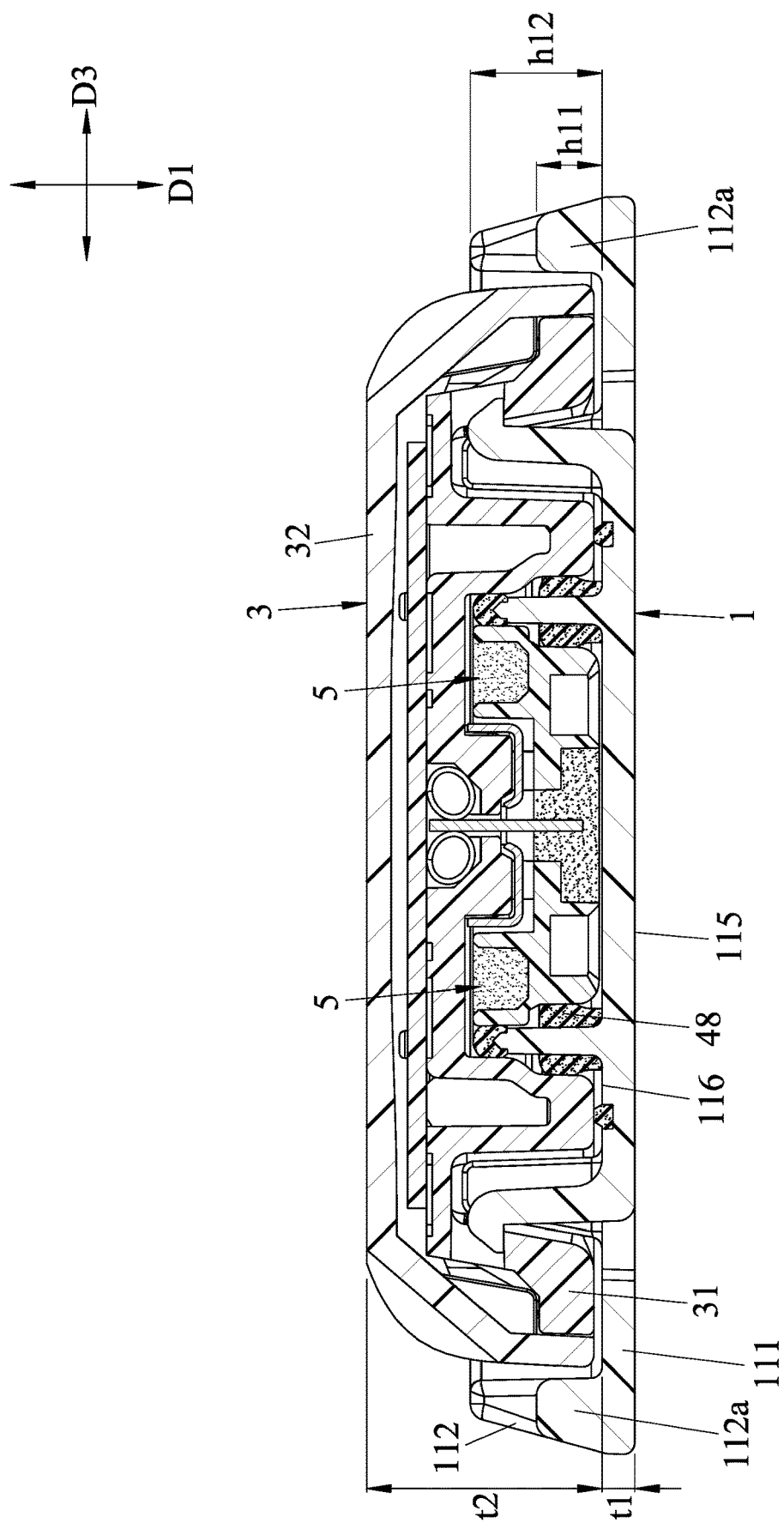
FIG. 36 is a sectional view of the fifth embodiment that is similar to FIG. 4.

Referring to FIGS. 35 and 36, a fifth embodiment of the physiological signal monitoring device is similar to that of the fourth embodiment, with differences as follows.

The height of the surrounding wall 112 of the base body 11 that is measured from the top surface 115 of the bottom plate 11 is not uniform, so that the base body 11 may be flexible to offer the same benefit of the third embodiment. Specifically, the surrounding wall 112 has a first height (h12) and a second height (h11). The first height (h12) is no more than a thickness (t2) of the transmitter 3, and the second height (h11) is larger than or equal to 0 mm but not larger than the first height (h12). Preferably, the second height (h11) ranges from 0 to 3 mm. In this embodiment, the first height (h12) is 4.9 mm, and the second height (h11) is 2.4 mm. Or, a ratio between the second and first heights (h11, h12) is no more than 0.5.

To be even more specific, the surrounding wall 112 of this embodiment has two short portions 112a respectively disposed at two longer sides thereof. Every portion of the short portions 112a has substantially the same height equivalent to the second height (h11). In addition, a length of the short portions 112a extending in the direction of the second axis (D2) is at least wide enough to be used as a pivot for bending the base body 11. The first and second coupling structures 12, 37 are uncoupled from each other when an external force is applied on the periphery of the base body 11 to bend the bottom plate (111) by the flexibility of the surrounding wall 112.

Figure 37:
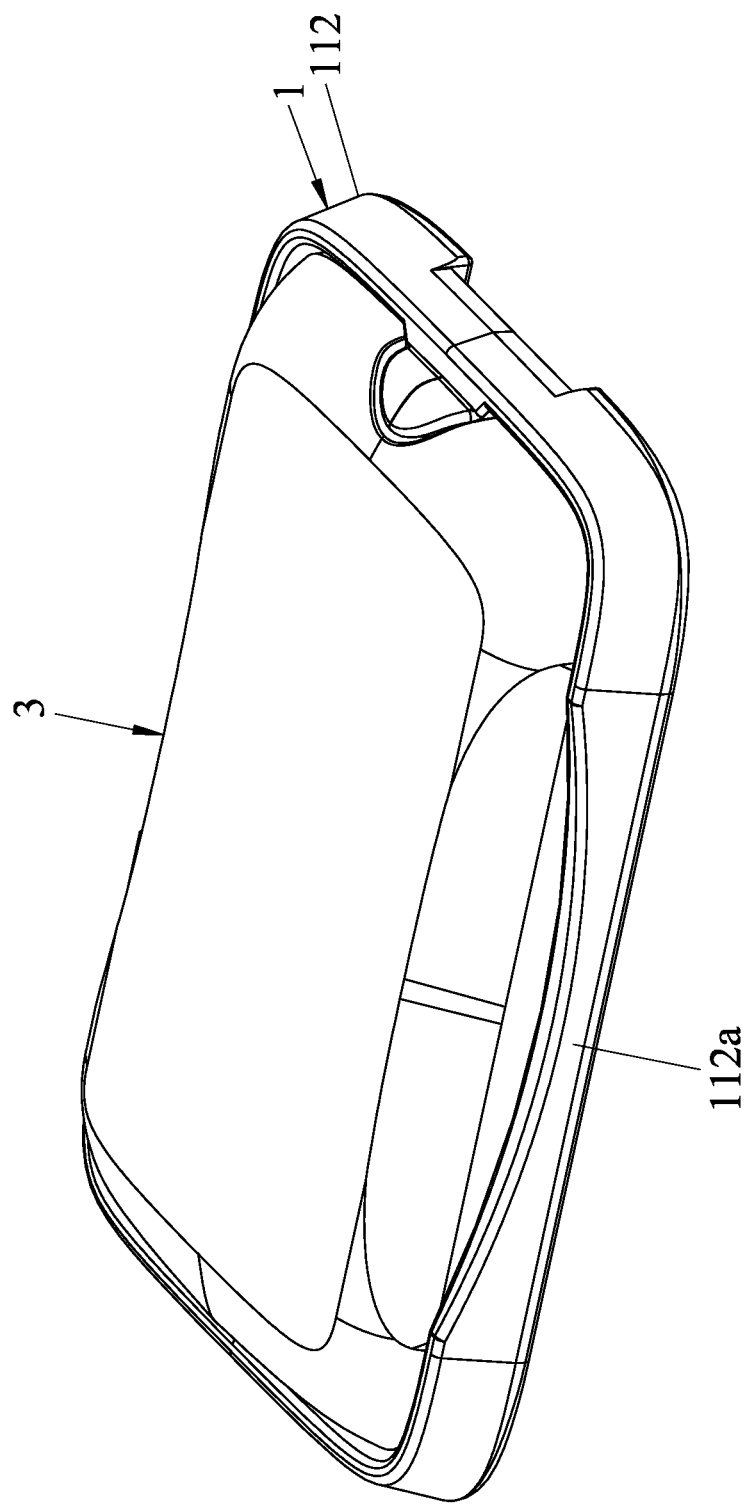
FIG. 37 is a perspective view of a modification of the fifth embodiment.
Figure 38:
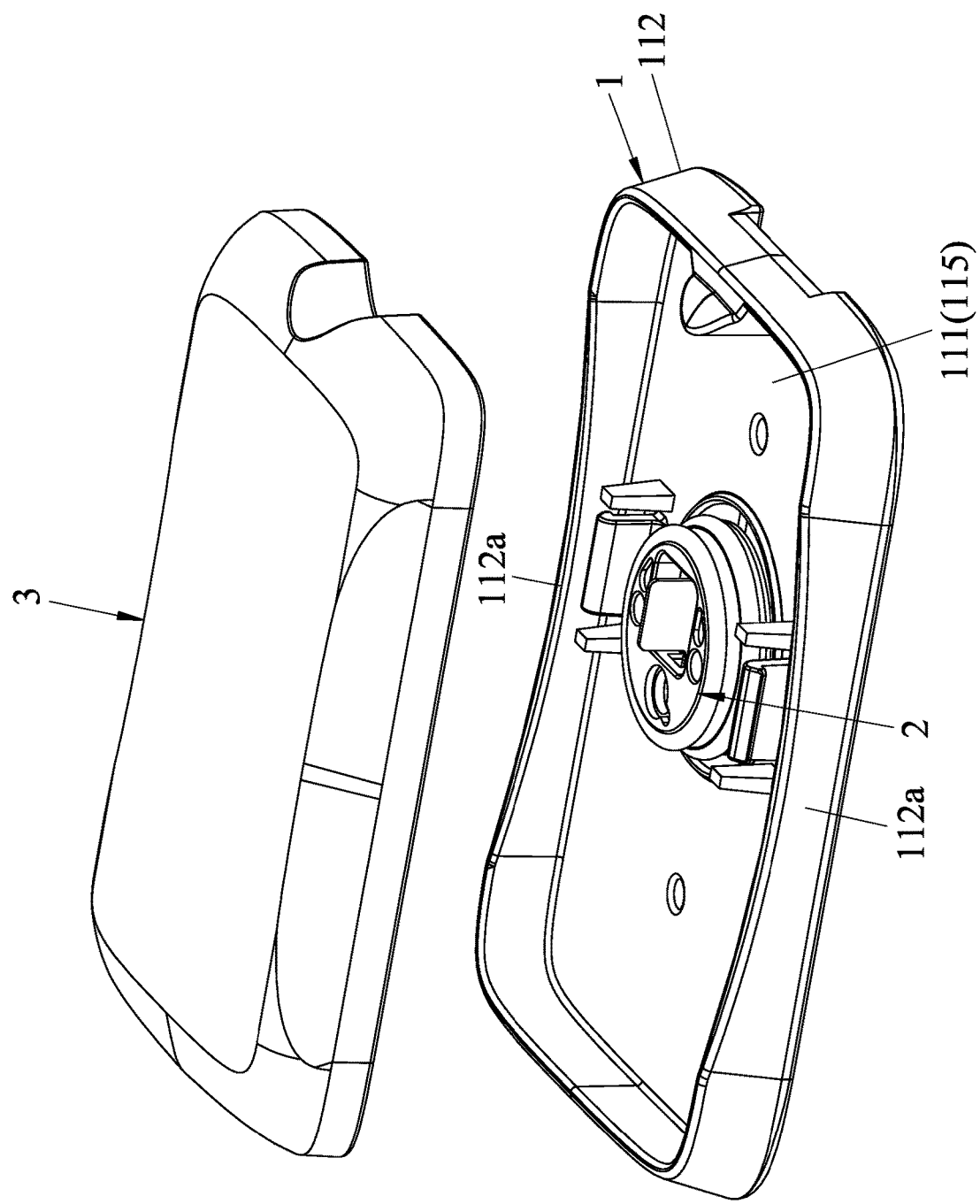
FIG. 38 is an exploded perspective view of the modification of the fifth embodiment.
Figure 39:
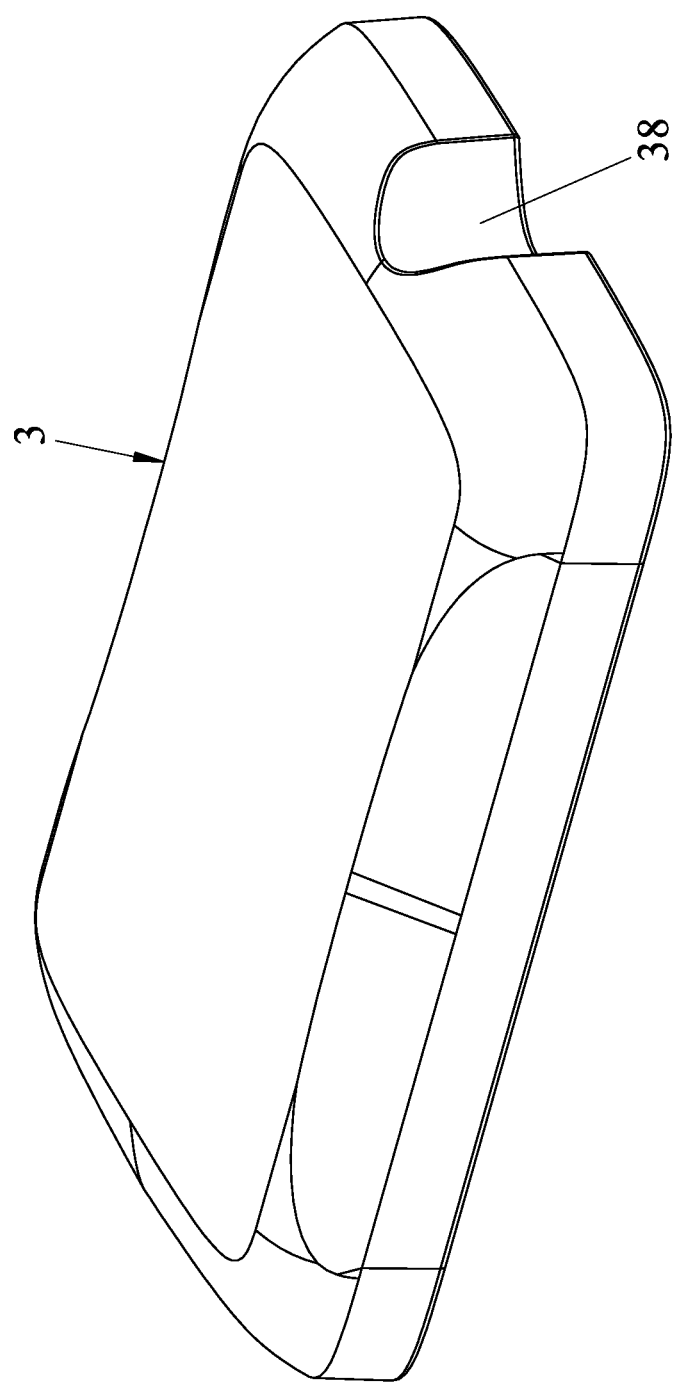
FIG. 39 is a perspective view of a sixth embodiment of the physiological signal monitoring device.

Referring to FIGS. 37 and 38, in a modification of the fifth embodiment, top edges of the short portions 112a are arc-shaped such that only centers of the short portions 112a have heights equivalent to the second height (h11), and not every portion of the short portions 112a have the same height. It should be noted that the first height (h12) of the surrounding wall 112 has to be high enough to prevent falling of the transmitter 3 from the base body 11 due to outside impact, and the second height (h11) is designated to be within the abovementioned range dependent on the materials used to enable bending of the base body 11 to separate the transmitter 3 therefrom without jeopardizing the stability of the whole device.

Referring to FIGS. 39 to 42, a sixth embodiment of the physiological signal monitoring device is similar to that of the fourth embodiment, with differences as follows.

Figure 40:
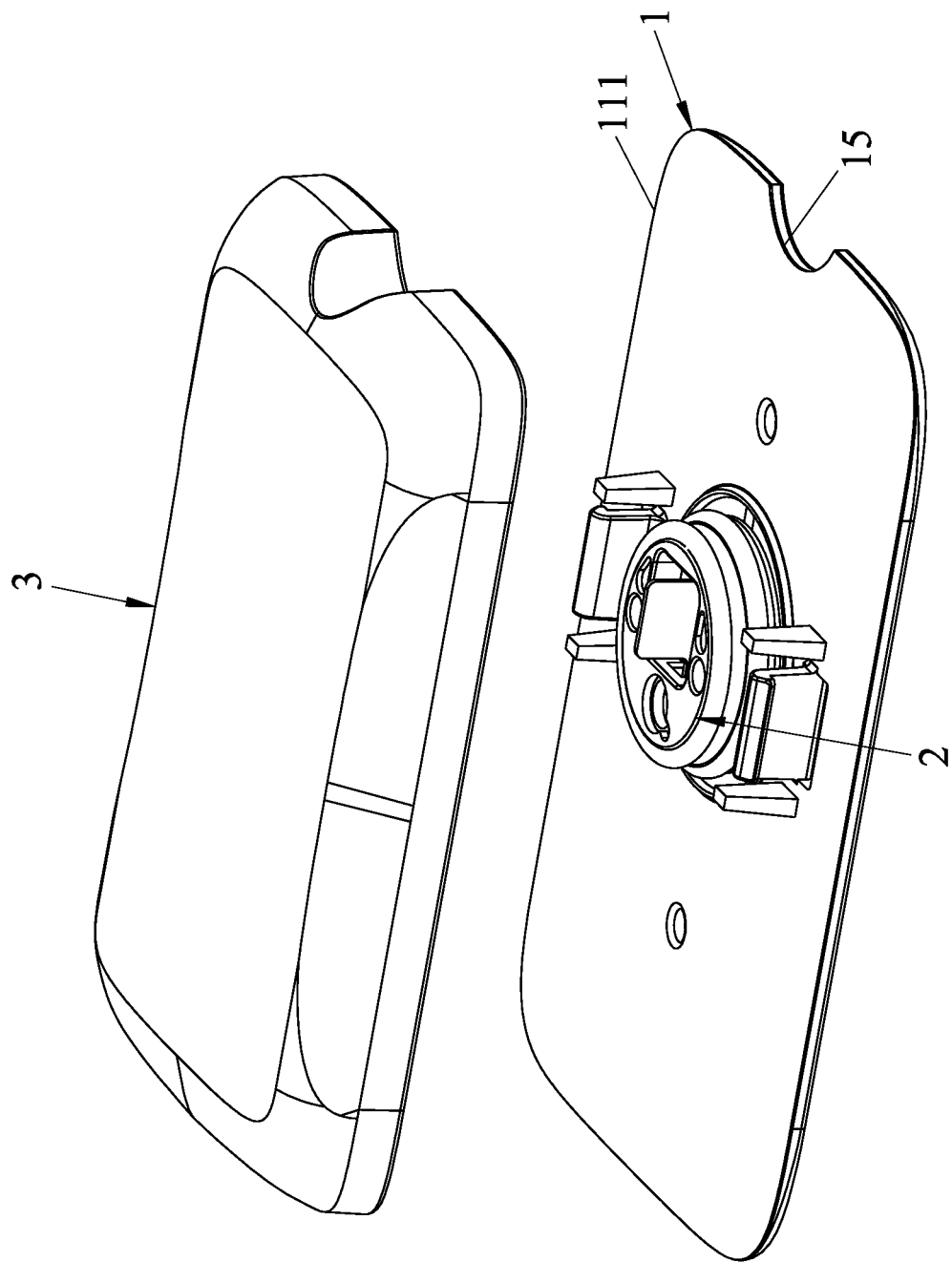
FIG. 40 is an exploded perspective view of the sixth embodiment.
Figure 41:
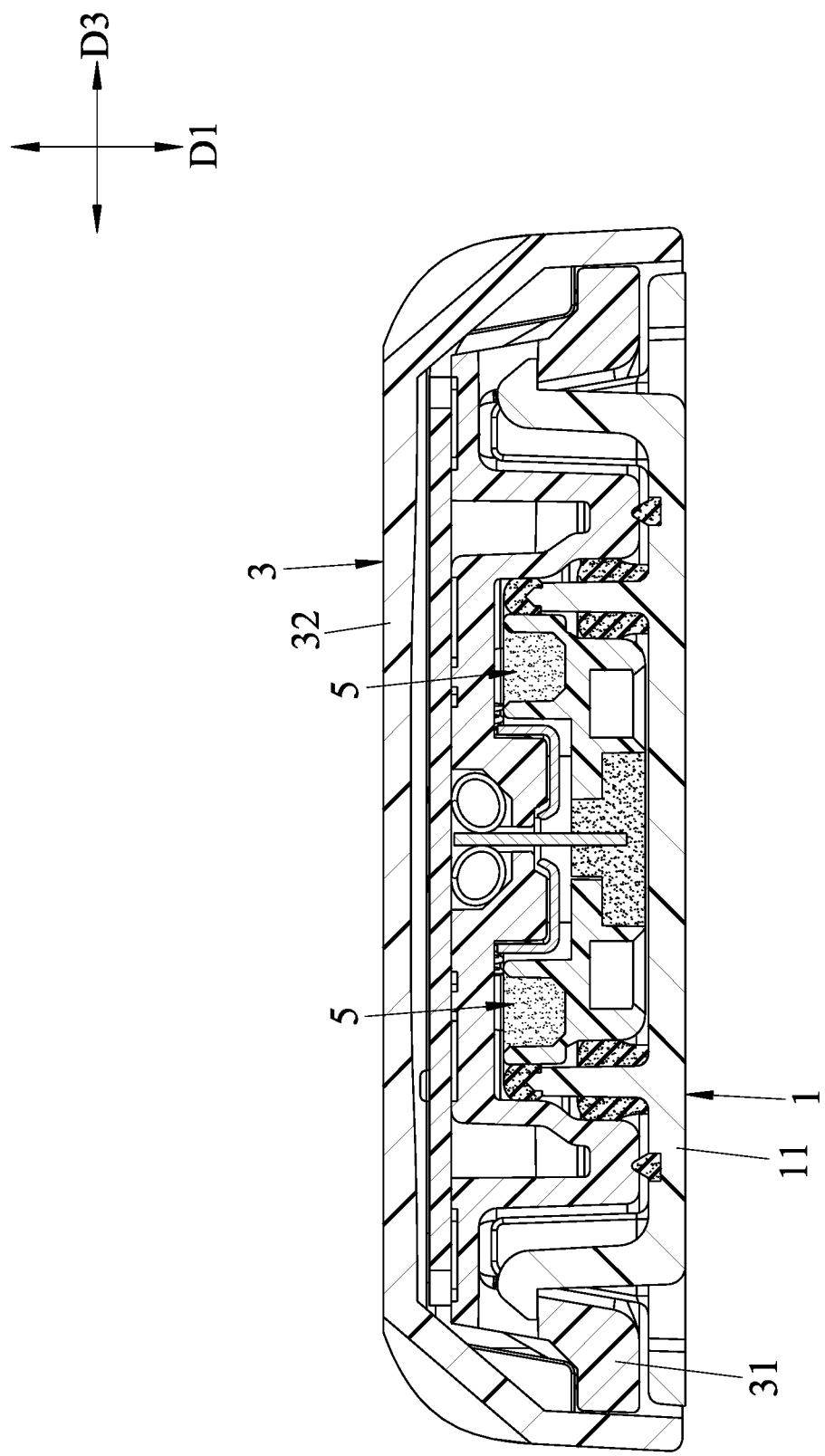
FIG. 41 is a sectional view of the sixth embodiment that is similar to FIG. 4.
Figure 42:
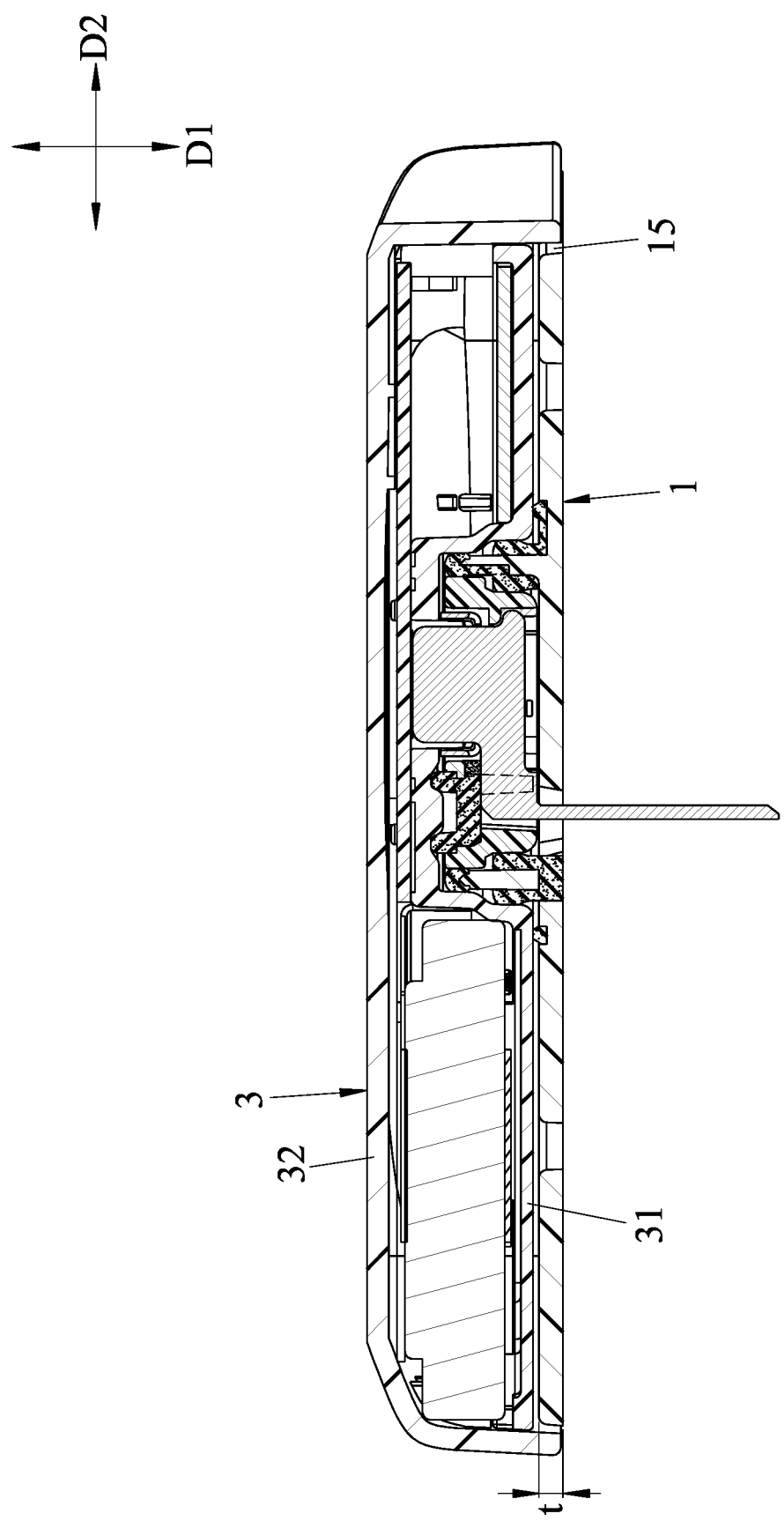
FIG. 42 is a sectional view of the sixth embodiment that is similar to FIG. 3.

Referring specifically to FIG. 40, the surrounding wall 112 of the base body 11 is omitted, and the top casing 32 of the transmitter 3 extends downwardly to surround a periphery of the bottom plate 111 of the base body 11. In addition, as shown in FIG. 40, the first aligning structure 15 of the base 1 is configured as a concaved portion on the periphery of the bottom plate 111.

Figure 43:
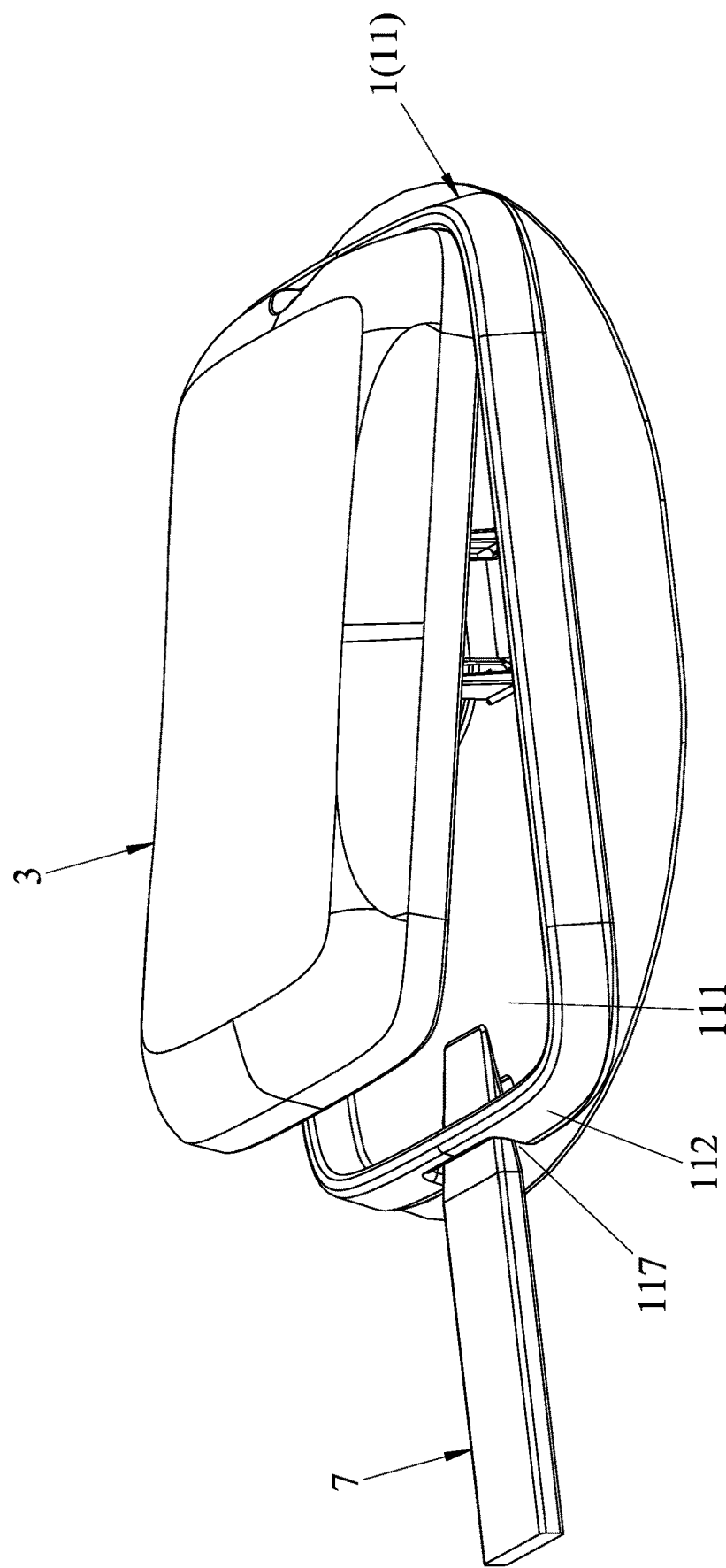
FIG. 43 is a perspective view of a seventh embodiment of the physiological signal monitoring device, illustrating the base and the transmitter being disengaged from each other via a disassembly member.

Referring to FIG. 43, a seventh embodiment of the physiological signal monitoring device is similar to that of the first embodiment, with differences as follows.

Figure 44:
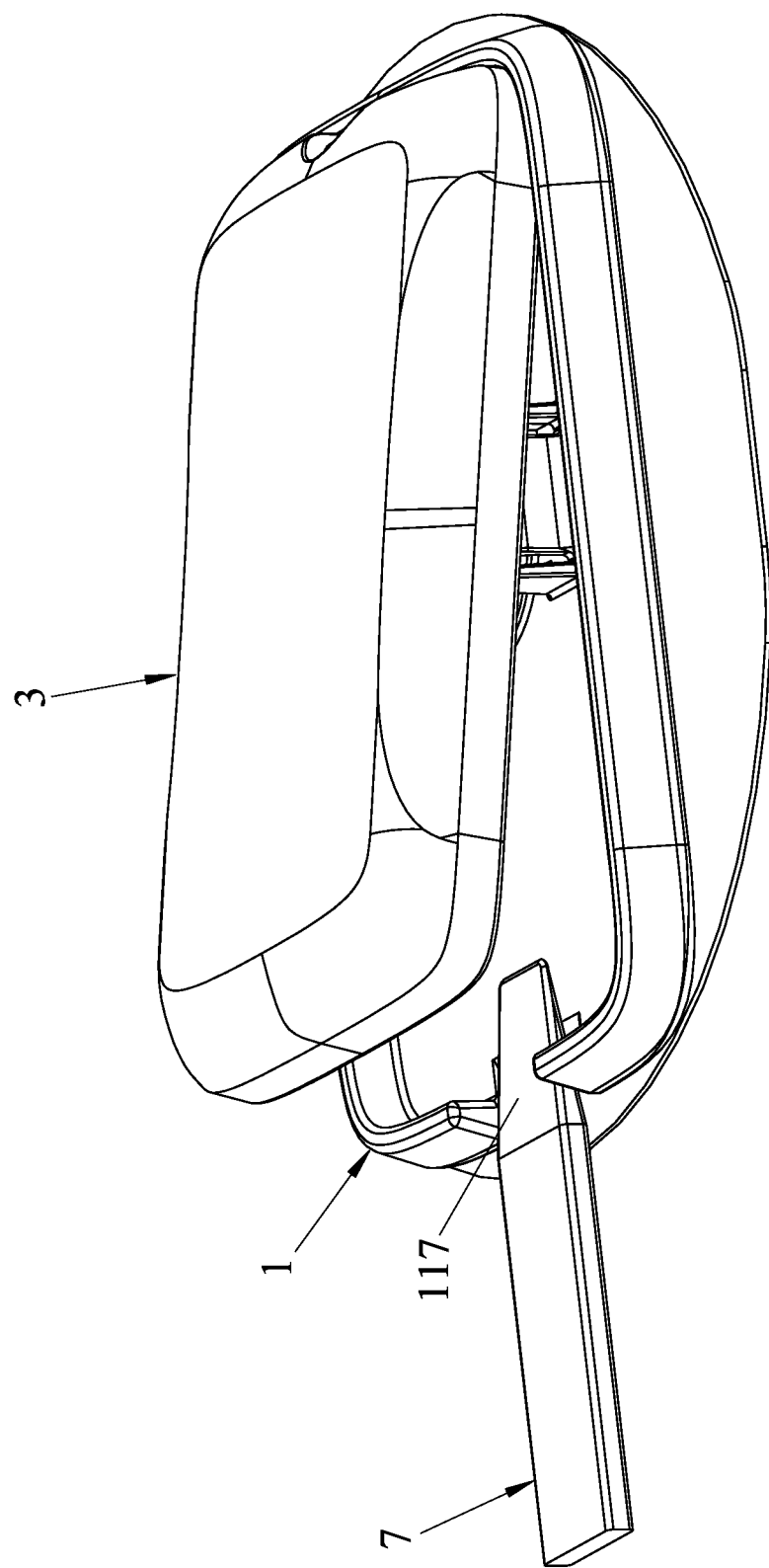
FIG. 44 is a perspective view of a modification of the seventh embodiment, illustrating the base and the transmitter being disengaged from each other via the disassembly member.
Figure 45:
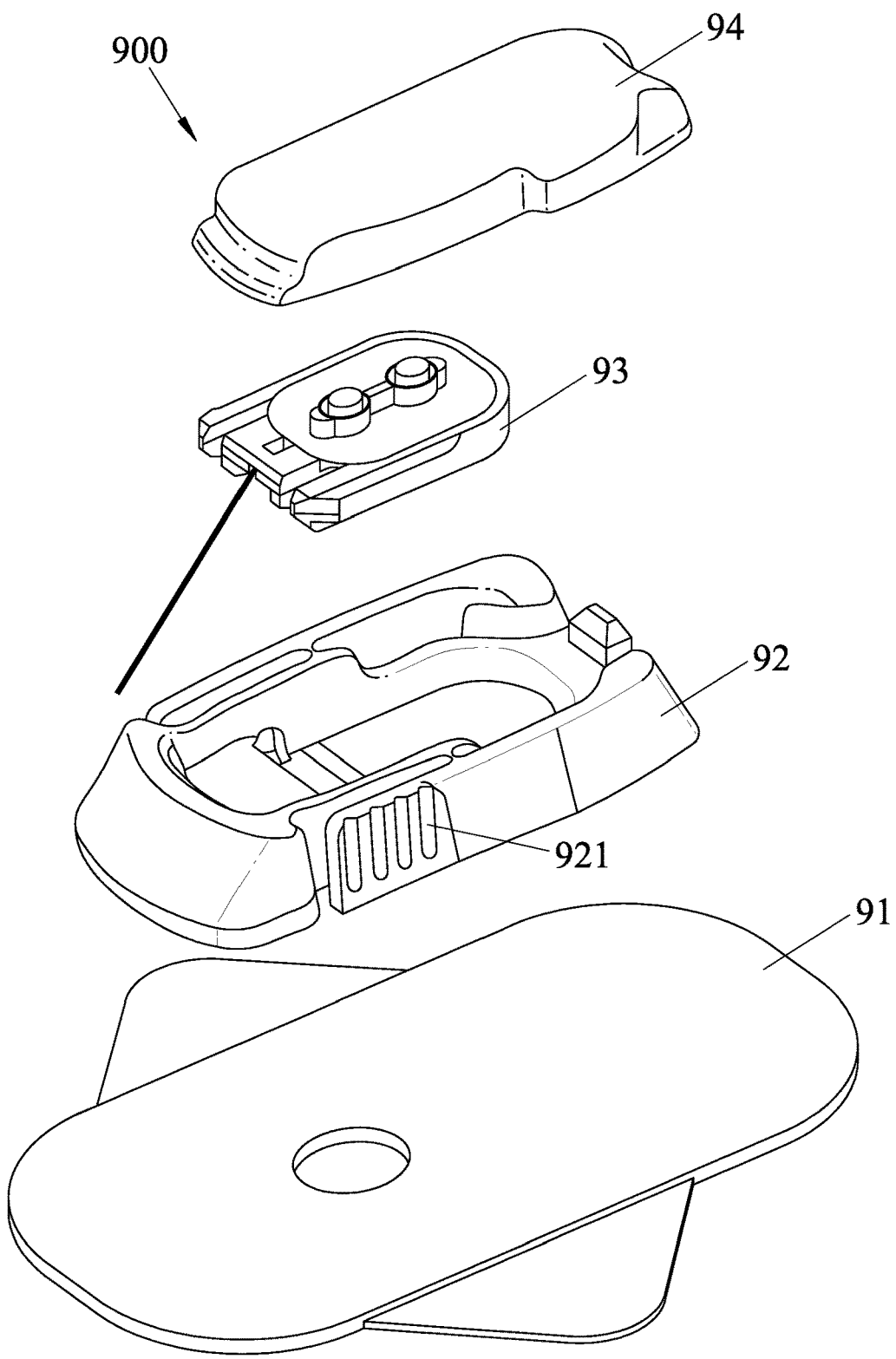
FIG. 45 is an exploded perspective view of a conventional sensing device.

In this embodiment, the number of opening 117 of the base body 11 is one. The opening 117 is formed in the surrounding wall 112 and is communicated to an external environment and a space between the bottom plate 111 of the base body 11 and the bottom casing 31 of the transmitter 3. The user is permitted to separate the transmitter 3 from the base 1 without detaching the physiological signal monitoring device from the skin surface of the host. In this embodiment, the opening 117 is disposed between a junction between the bottom plate 111 and the surrounding wall 112. To remove the transmitter 3 from the base 1, the user may use a disassembly member 7 to pass through the opening 117 into the space between the bottom casing 31 and the bottom plate 111 to push the transmitter 3 away from the base 1, so that the first and second coupling structures 12, 37 are able to be separated from each other. The opening 117 may bear a different shape in a modification of this embodiment, such as extending from a top end of the surrounding wall 112 to a bottom end thereof as shown in FIG. 44, without affecting the performance of the disassembly member 7 in separating the transmitter 3 from the base 1.

Overall, the physiological signal monitoring device of this disclosure utilizes the first and second coupling structures 12, 37 to facilitate replacements of the base 1 and the biosensor 2, so that the transmitter 3 may be reused with new sets of the base 1 and the biosensor 2 for future use. Since the first and second coupling structures 12, 37 are disposed to be distal from the periphery cooperatively defined by the base 1 and the transmitter 3 when the first and second coupling structures 12, 37 are coupled to each other, the periphery does not need to have any disassembly member meant for disassembling the transmitter 3 from the base 1, thereby permitting the physiological signal monitoring device to have a simpler and more compact, portable design.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A physiological signal monitoring device comprising:
   a base (1) that includes
      a base body (11) that is flexible and that has a bottom plate (111) adapted to be mounted to a skin surface of a host, and
      at least one first coupling structure (12) that is disposed on a top surface (115) of said bottom plate (111);
   a biosensor (2) that is mounted to said base (1), and that is adapted to measure at least one analytical substance of the host and to send a physiological signal corresponding to the analytical substance; and
   a transmitter (3) that is removably mounted to said base body (11), that is connected to said biosensor (2), and that is for receiving and transmitting the physiological signal, said transmitter (3) including
      a bottom casing (31) facing said top surface (115) of said bottom plate (111) of said base body (11), and
      at least one second coupling structure (37) disposed on said bottom casing (31) and corresponding in position to said at least one first coupling structure (12) of said base (1);
   wherein, said first and second coupling structures (12, 37) are coupled to each other when said transmitter (3) is mounted to said base body (11) of said base (1), and are uncoupled from each other when an external force is applied on a periphery of said base body (11) to bend said bottom plate (111) by the flexibility of said base body (11);
   wherein, said first and second coupling structures (12, 37) are disposed to be distally away from a periphery cooperatively defined by said base (1) and said transmitter (3) when said first and second coupling structures (12, 37) are coupled to each other; and
   wherein said first and second coupling structures (12, 37) are disposed distal to a whole periphery of said physiological signal monitoring device when said first and second coupling structures (12, 37) are coupled to each other.

2. The physiological signal monitoring device as claimed in claim 1, wherein said base body (11) is made of a polymer material, a metallic material or a mixture of the polymer material and the metallic material.

3. The physiological signal monitoring device as claimed in claim 1, wherein a thickness (t1) of said bottom plate (111) of said base (1) is ranged from 0.05 millimeters to 1 millimeter.

4. The physiological signal monitoring device as claimed in claim 1, wherein:
   said base body (11) of said base (1) further includes a surrounding wall (112) that extends upwardly from a periphery of said bottom plate (111), and that has a first height (h12) and a second height (h11) that are both measured from said top surface (115) of said bottom plate (111); and
   the first height (h12) is no more than a thickness (t2) of said transmitter (3), and the second height (h11) is larger than or equal to 0 millimeter but not larger than the first height (h12).

5. The physiological signal monitoring device as claimed in claim 1, wherein said first coupling structure (12) of said base (1) protrudes from said top surface (115) of said bottom plate (111) of said base body (11), and has
   a base portion (120) that is connected to said top surface (115) of said bottom plate (111), and
   a first coupling portion (121) that is connected to an end of said base portion (120) distal from said top surface (115), extends along a direction toward or away from the periphery of said base body, and is capable of being removably coupled to said second coupling structure (37).

6. The physiological signal monitoring device as claimed in claim 1, wherein:
   said second coupling structure (37) of said transmitter (3) is configured as a groove formed on said bottom casing (31); and
   when said transmitter (3) is mounted to said base body (11) of said base (1), at least a portion of said first coupling structure (12) is engaged into said second coupling structure (37).

7. The physiological signal monitoring device as claimed in claim 1, wherein said base body (11) further has at least one opening (117) through which an external force is adapted to be applied so as to disengage said second coupling structure (37) from said first coupling structure (12), thereby separating said transmitter (3) from said base (1).

8. The physiological signal monitoring device as claimed in claim 7, wherein said opening (117) extends through said bottom plate (111), and is in proximity to said first coupling structure (12).

9. The physiological signal monitoring device as claimed in claim 1, wherein said base body (11) has long edges and short edges, and wherein the external force is applied on one of said short edges of said base body (11) or on a corner of said base body (11).

10. The physiological signal monitoring device as claimed in claim 1, wherein said base (1) further includes a first aligning structure (15) that is disposed at a side of said base body (11), and said transmitter (3) further includes a second aligning structure (38) that is disposed at a side thereof and fits with said first aligning structure (15).

11. The physiological signal monitoring device as claimed in claim 1, further comprising a desiccant (5) that is mounted in an airtight space (100) cooperatively defined by said base (1) and said transmitter (3), said airtight space (100) being formed between said bottom plate (111) of said base (1) and said bottom casing (31) of said transmitter (3).

12. A physiological signal monitoring device comprising:
   a base (1) that includes a base body (11) having a bottom plate (111) that is adapted to be mounted to a skin surface of a host, and a surrounding wall (112) that extends upwardly from a periphery of said bottom plate (111), the height of said surrounding wall (112) of said base body (11) measured from a top surface (115) of said bottom plate (11) being not uniform so that said base body (11) is flexible, and at least one first coupling structure (12) disposed on said top surface (115) of said bottom plate (111);

biosensor (2) that is mounted to said base (1), and that is adapted to measure at least one analytical substance of the host and to send a physiological signal corresponding to the analytical substance; and a transmitter (3) that is removably mounted to said base body (11), that is coupled to said biosensor (2), and that is for receiving and transmitting the physiological signal, said transmitter (3) including a bottom casing (31) facing said top surface (115) of said bottom plate (11 1) of said base body (11), and at least one second coupling structure (37) disposed on said bottom casing (31) and corresponding in position to said at least one first coupling structure (12) of said base (1);

wherein, said first and second coupling structures (12, 37) are coupled to each other when said transmitter (3) is mounted to said base body (11) of said base (1), and are uncoupled from each other when an external force is applied on a periphery of said base body (11) to bend said bottom plate (111) by the flexibility of said surrounding wall (112);

wherein, said first and second coupling structures (12, 37) are disposed to be distally away from a periphery cooperatively defined by said base (1) and said transmitter (3) when said first and second coupling structures (12, 37) are coupled to each other; and wherein said first and second coupling structures (12, 37) are disposed distal to a whole periphery of said physiological signal monitoring device when said first and second coupling structures (12, 37) are coupled to each other.

13. The physiological signal monitoring device as claimed in claim 12, wherein a thickness (t1) of said bottom plate (111) of said base (1) is ranged from 0.05 millimeters to 1 millimeter.

14. The physiological signal monitoring device as claimed in claim 12, wherein said surrounding wall (112) has a first height (h12) and a second height (h11) that are both measured from said top surface (115) of said bottom plate (111); and the first height (h12) is no more than a thickness (t2) of said transmitter (3), and the second height (h11) is larger than or equal to 0 millimeter but not larger than the first height (h12).

15. The physiological signal monitoring device as claimed in claim 14, wherein a top edge of said surrounding wall (112) distal from said bottom plate (111) is arc-shaped.

16. The physiological signal monitoring device as claimed in claim 12, wherein said base body (11) has long edges and short edges, and wherein the external force is applied on one of said short edges of said base body (11) or on a corner of said base body (11).

17. A physiological signal monitoring device comprising:
a base (1) that includes
a base body (11) that is flexible and that has a bottom plate (111) adapted to be mounted to a skin surface of a host, and a surrounding wall (112) extending upwardly from a periphery of said bottom plate (111), and at least one first coupling structure (12) that is disposed on a top surface (115) of said bottom plate (111);

a biosensor (2) that k mounted to said base (1), and that is adapted to measure at least one analytical substance of the host and to send a physiological signal corresponding to the analytical substance; and a transmitter (3) that is removably mounted to said base body (11), that is connected to said biosensor (2), and that is for receiving and transmitting the physiological signal, said transmitter (3) including a bottom casing (31) facing said top surface (115) of said bottom plate (111) of said base body (11), and at least one second coupling structure (37) disposed on said bottom casing (31) and corresponding in position to said at least one first coupling structure (12) of said base (1), wherein said first and second coupling structures (12, 37) are coupled to each other when said transmitter (3) is mounted to said base body (11) of said base (1), and are uncoupled from each other when an external force is applied on a periphery of said base body (11) to bend said bottom plate (111) by virtue of the flexibility of said base body (11);

wherein, when said transmitter (3) is mounted to said base body (11) of said base (1), said transmitter (3) k surrounded by said surrounding wall (112), an outer perimeter of said transmitter (3) being smaller than or equal to an inner perimeter of said surrounding wall (112);

wherein said first and second coupling structures (12, 37) are disposed to be distally away from a periphery cooperatively defined by said base (1) and said transmitter (3) when said first and second coupling structures (12, 37) are coupled to each other; and wherein said first and second coupling structures (12, 37) are disposed distal to a whole periphery of said physiological signal monitoring device when said first and second coupling structures (12, 37) are coupled to each other.

* * * * *